(12) United States Patent
Scanlan et al.

(10) Patent No.: US 6,440,663 B1
(45) Date of Patent: Aug. 27, 2002

(54) RENAL CANCER ASSOCIATED ANTIGENS AND USES THEREFOR

(75) Inventors: Matthew J. Scanlan; Elisabeth Stockert; Yao-Tseng Chen; Lloyd J. Old, all of New York, NY (US); Elke Jager; Alex Knuth, both of Frankfurt AM Main (DE)

(73) Assignees: Ludwig Institute for Cancer Research; The New York Hospital-Cornell Medical Center, both of New York, NY (US)

( * ) Notice: Subject to any disclaimer, the term of this patent is extended or adjusted under 35 U.S.C. 154(b) by 0 days.

(21) Appl. No.: 09/166,350

(22) Filed: Oct. 5, 1998

(51) Int. Cl.$^7$ .......................... C12Q 1/68; C12P 19/34; A61K 38/00; C07H 21/02
(52) U.S. Cl. ...................... 435/6; 435/91.1; 435/91.2; 530/300; 536/23.1
(58) Field of Search .................. 435/6, 91.1, 91.2; 536/23.1; 530/300

(56) References Cited

U.S. PATENT DOCUMENTS 5,665,874 A * 9/1997 Kuhajda et al. ............ 536/24.3
5,698,396 A   12/1997 Pfreundschuh ................ 435/6

OTHER PUBLICATIONS

Kiyokawa et al., "Overexpression of ERK, an EPH Family Receptor Protein Tyrosine Kinase, in Various Human Tumors," 1994, vol. 64, pp. 3645–3650.*

Sahin et al. *Proc. Natl. Acad. Sci USA* 92:11810–11813 (1995).
Thomson et al., *Proc. Natl. Acad. Sci. USA* 92:5845–5849 (1995).
Gilbert et al., *Nature Biotechnol.* 15:1280–1284 (1997).
Coulie, *Stem Cells* 13:393–403 (1995).
Thomson et al., *J. Immunol.* 157(2):822–826 (1996).
Tam et al., *J. Exp. Med.* 171(1):299–306 (1990).

* cited by examiner

*Primary Examiner*—Kenneth R. Horlick
*Assistant Examiner*—Young Kim
(74) *Attorney, Agent, or Firm*—Wolf, Greenfield & Sacks, P.C.

(57) ABSTRACT

Cancer associated antigens have been identified by autologous antibody screening of libraries of nucleic acids expressed in renal cancer cells using antisera from cancer patients. The invention relates to nucleic acids and encoded polypeptides which are cancer associated antigens expressed in patients afflicted with renal cancer. The invention provides, inter alia, isolated nucleic acid molecules, expression vectors containing those molecules and host cells transfected with those molecules. The invention also provides isolated proteins and peptides, antibodies to those proteins and peptides and cytotoxic T lymphocytes which recognize the proteins and peptides. Fragments of the foregoing including functional fragments and variants also are provided. Kits containing the foregoing molecules additionally are provided. The molecules provided by the invention can be used in the diagnosis, monitoring, research, or treatment of conditions characterized by the expression of one or more cancer associated antigens.

12 Claims, No Drawings

SEQUENCE LISTING

<160> NUMBER OF SEQ ID NOS: 35

<210> SEQ ID NO 1
<211> LENGTH: 4422

-continued

```
<212> TYPE: DNA
<213> ORGANISM: Homo sapiens
<220> FEATURE:
<221> NAME/KEY: unsure
<222> LOCATION: 512..512
<223> OTHER INFORMATION: n = a, c, g or t
<220> FEATURE:
<221> NAME/KEY: unsure
<222> LOCATION: 1477..1477
<223> OTHER INFORMATION: n = a, c, g or t
<220> FEATURE:
<221> NAME/KEY: unsure
<222> LOCATION: 2217..2217
<223> OTHER INFORMATION: n = a, c, g or t
<220> FEATURE:
<221> NAME/KEY: unsure
<222> LOCATION: 4125..4125
<223> OTHER INFORMATION: n = a, c, g or t
<220> FEATURE:
<221> NAME/KEY: unsure
<222> LOCATION: 4153..4153
<223> OTHER INFORMATION: n = a, c, g or t

<400> SEQUENCE: 1
gattattctg gaggaagatg accttcattt tatggttatg tgtgtgtgtc tgtgtgtctt      60
tggaaaaata tatataattt tttcaaatag gaagccaaca tatcaagtga tgaattaaag     120
tatgctgcag aatatatatt ctaaaactac aaaaaagtca ctgaatatca aaatgataca     180
gcttatacat atagttactg tgacaagtga cagactgcta gttcagaatt caaaaatcct     240
ttcctagttt gtgagataat gggctaaatt ccttctgcct gccactgggg caaagcaaat     300
tgctttagtt tttgatgaga gttcttagaa gtttgttggt attccttcat ccacagcatc     360
cattgttgaa ataaccattt tcagttgtga tgccttaact aagaagccaa ttgttagcct     420
gaaatgcaat cttggtagcc agtttcaatg aagctagaga ttagtcagaa aaagttagct     480
gttgggcttt agaaagggat tttgagtcct gncatttcta cttgggagca ttttggagca     540
gattaagctt tcagtataaa aacaagtggc tacctgatgg aaacttttct taccctttata    600
gggaaactga gcacaagctg aatgatattg tctgctgcaa aaaaaaacaa acaaaaaaaa     660
aacaaaacaa aaaacaaaaa aaaaaaaaaa aaaacctcgt gccgaattcg gcacgagggg     720
aagccccgtg cacccccgc cctccggccg ccgccgcccc gctggccctg cagccgtcgc     780
cgctgcctcg ggctacagcc ccgggctcgg cggtcccggc tggggaagga gggcggcgag     840
cgcgtccgga gccgcggag atggcggag ggcactgcgg cagcttcccc gcggcggcgg      900
ccggcagcgg cgagatcgtc caactgaacg taggggggac cagatttagt acctcaagac     960
aaactcttat gtggattcca gattcttttt tttccagttt gctgagtggg agaatttcaa    1020
cacttcgaga tgaaactggt gctatattta ttgatagaga tccagcagca tttgcaccca    1080
tttaaatttt tcttcggaca aaagaactag acttaagggg agtgagtatt aatgttctca    1140
ggcatgaagc agaattttac gggatcactc cattagtaag aaggcttctc ttatgtgaag    1200
aattggagcg ttcctcttgt ggcagtgtcc tttttcatgg ttacttgccc ccaccaggta    1260
ttcctagtcg taaataaac aacacagtca gatctgctga ttctaggaat ggtctaaatt     1320
ctacagaagg tgaagcccgg ggaaatggta cacagcctgt tctctctgga acgggagaag    1380
aaactgttag ctaggatttt cctgtggatc cacgaaaggt gctaatagta gctggccatc    1440
acaactggat tgtagctgca tatgcccatt ttgctgngtg gtacagaatc aaagaatctt    1500
caggatggca gcaagtgttt acgagcccat atttggattg gactatcgaa cgagtagctt    1560
taaatgcaaa ggtggttgga gggccacatg gagacaaaga caaatggtt gctgttgcct     1620
```

-continued

```
cagagagtag catcatcttg tggagtgttc aggatggggg aagtggaagt gaaattggag    1680
tgttcagcct gggtgttcct gtagatgctc tcttctttat tggtaaccag ttggtggcca    1740
cgagtcatac agggaaagtg ggagtgtgga atgctgtcac tcagcactgg caggttcaag    1800
atgttgttcc tataactagt tatgacactg ctggatcatt ccttctgctt ggatgtaaca    1860
atggatcaat atattacata gatatgcaga agttcccctt gcgaatgaaa gataatgatc    1920
ttcttgtaac tgaactgtat catgatcctt caaatgatgc tattactgct ctgagtgttt    1980
acctcacacc caaaacaagt gtcagtggta actggatcga gatcgcctat ggtacgagct    2040
ctggagcagt acgagtgatt gtacaacacc cagagacagt tgggtcaggt cctcagcttt    2100
ttcagacttt cacagttcac cgaagtcccg taacaaaaat catgctatca gagaagcatc    2160
ttgtatcagt ctgtgcagat aataatcatg tccggacgtg gacagtaaca cgattcngag    2220
gaatgatctc tactcagcca ggttctactc ctttagcgtc attcaagata ctatccctgg    2280
aggagacaga aagtcatggt agctattcct ctggaaatga cataggacct tttggagagc    2340
gagacgatca acaggtgttt atccagaaag ttgttcccat caccaacaaa ctatttgtaa    2400
gactctcatc gactggaaaa agaatatgtg agatccaggc tgttgactgt actacaatat    2460
cctcatttac agtgagggaa tgtgagggat ccagtaggat gggctcaaga ccaaggcgct    2520
acttgttcac aggccataca aatggcagta ttcaaatgtg ggatctgacc actgctatgg    2580
atatggttaa caaagtgaa gataaggatg taggtggtcc aaccgaagaa gagctactca    2640
aattactcga tcaatgtgat ttgagcacat ctcgctgtgc tactcctaac atcagtccag    2700
caacttccgt agttcagcat agccacttac gagaatcaaa ttctagcctt cagcttcagc    2760
accatgatac cacccatgaa gcagctactt acggttccat gaggccttac agagaaagtc    2820
ctttattagc aagggcaaga aggactgaga gctttcacag ttatagggac ttccagacta    2880
ttaatttgaa cagaaatgta gaaagagctg tccctgaaaa tggtaacttg ggtccaatac    2940
aagctgaagt gaaaggggca acaggggaat gtaatatatc tgagagaaag tctcctggag    3000
tagaaataaa aagtttgaga gaattggata gtggattgga agtgcataaa atagctgaag    3060
gtttttcaga atccaagaaa aggtcatcag aagatgaaaa tgaaaataaa atagagttta    3120
ggaagaaagg aggatttgaa gggggaggat tccttggaag aaagaaagtt ccctatctgg    3180
catcatcacc aagtacttcc gatggaggaa ctgactcacc tggtactgcg tccccatctc    3240
ctacaaagac tactccatct cctcggcata aaaaaagtga ttcttcaggt caggagtaca    3300
gcttgtgaaa actcaccaaa atgaatagtt gtttcggtta catttagatg aaagttaaac    3360
tttactgaat tcagtacat tagtttttac actaaaactt tacaagataa aattggactt    3420
catttagtat cttttaaca gaattacttg gaataatgag atacaataat catatctctt    3480
ttgacatttt ggaaattttt ttaattttac aagtacattt aacagatcat ttataaagca    3540
ggagtccatt ttaacactta ccgactttt ttggtttgga aacatattac cacgtcttaa    3600
taggatggtg cccatatagg tgagcatccc tttagatcat gggaaccagc agactgcatt    3660
cctaatcttc attatgcctg agacttgtct tacaatgtta cctttaagtg aatcacataa    3720
ttgtctttgg aacttggtct cccaacactt attgtgattg caaagtgttt accagatatt    3780
tgatgaggtg ctatgtttgt gaaaaacata tcatgtaatt caaaaacact attgatattg    3840
aataccagat accactatgt agtaagtctt ttaggatgat tttaatttag tcgtgcgtca    3900
ttttctgatt ctcatcattg ggagatctta aatcttagca agcattagca atattaaatg    3960
ccaaaattcc attgaaactt tcaagttgga gcaattgtct gtgtttgaaa agatgaaata    4020
```

```
aaaataataa tcaagggcaa agctttgagt gcccagaagg gaaagctgta ccagttgcta    4080
acctgtcttg tttcaggagc caccatgttt tttttttcagt gttancaaca atcatgataa    4140
ttaaattaaa acnctagttt gttcacttgt aggactgcag ttctgaattt tgggttaaag    4200
gttttggctg ctgtaagaat gtgaatttga atgtattttg aattgtaaga gcaaaagaac    4260 gttttttgtac aattttttttt catttaattg gaatgatctt caggtttcta caaatagggt    4320
aattgtaaat ttaaagcatt agcatttatt ggtgaataat gtatatatcc ccattccaag    4380 aaaataagt gagtgaagtt gaaataaaat ctttaaaatt ta                         4422

<210> SEQ ID NO 2
<211> LENGTH: 502
<212> TYPE: DNA
<213> ORGANISM: Homo sapiens

<400> SEQUENCE: 2
gctagcttcg gcgcggatcc ctgggcgtcc gtacgtcgga gtccttcgtc ctccagggtc      60
cctgttcttt gcgccagcgg gaaccactat ctctgcactc ctgggttttt gttacatggc     120
tgctttcctc aaaatgagtg ttagtgtcaa tttcttcaga cctttcacca ggttttttggt    180 gccatttacc cttcatagga agagaaataa cttaacaatt ttgcagagat acatgtcttc     240
caaaatacca gctgttactt atcctaaaaa tgagagtaca cgcccttctg aagagctaga     300
gttggataag tggaaaacta ccatgaaatc tagtgtgcaa gaagaatgtg tttcaacaat     360
ctcaagcagt aaggatgaag atcctctagc tgccaccaga gagttcattg agatgtggag     420
attgcttggc agagaagtac cagaacacat cactgaagaa gagctcaaaa cccttatgga     480
atgtgtttct aacacagcaa aa                                              502

<210> SEQ ID NO 3
<211> LENGTH: 1948
<212> TYPE: DNA
<213> ORGANISM: Homo sapiens

<400> SEQUENCE: 3
ccatgtgagg gaggggcccg ctcctgcttg gtgacagagt cagcacgcgg tggcctgcag       60
ttcctccagc agtgtgaccg ggaggatctg gtggaattgg ctctgcctca gctggctcag     120
gttgtgaccg tgtatgagtt tcttctgatg aaggttgaaa aagatcatct agcaaagcct     180 ttttttcccag ctatatataa ggaatttgaa gagttgcata aaatggttaa gaaaatgtgc    240
caagattacc tcagtagttc tggtctgtgt tcccaggaga ccctggaaat aaacaatgat     300
aaggttgctg agtcattagg aatcacagaa ttcctacgga agaaagaaat acacccagac     360
aaccttggac ccaagcacct cagccgagac atggatgggg agcagctaga gggagctagc     420
agcgagaaga gggaacgtga ggctgcggag gagggactgg cctcagtgaa aagggcccaga    480 agagaagccc tgtccaacga taccactgaa tctcttgctg ccaacagcag aggccgggag     540
aagcccaggc ccttgcatgc tttgcccgct ggttttttccc ctccagtaaa tgtgactgtc     600 tctcccccgtt ctgaagaaag ccatacaacg acggtttctg gtggcaatgg gagcgtgttc    660
caggcgggcc cgcagcttca ggcactggct aacttagaag ccaggagggg gtctataggt     720
gctgctctct catcccggga tgtcagtggg ctgcctgttt atgctcagtc aggagagcct     780
aggaggctga cccaggcaca ggtggcagcg tttcctggag agaatgcttt ggaacactct     840
tcagaccagg acacctggga cagcctgagg agcccgggtt tctgcagccc tttgtcatct     900
```

-continued

```
ggtggtggag cagagtccct gccgcctggg gggcctggac atgcagaggc aggacacctc    960
ggcaaggttt gtgacttcca cctgaaccac cagcagccca gccccaccag cgtcctgcct   1020
acagaggtgg cagcccctcc gcttgagaaa attttgtctg tggatagcgt ggcagtggac   1080
tgtgcctaca ggactgtgcc caagccaggg cctcagcctg cccacatgg atcactattg    1140 actgaagggt gtctcagaag cctttcgggg acttgaacc ggttcccctg tgggatggag    1200
gtgcactctg gccagagaga actggagagc gtggttgctg tcggcgaagc catggctttg   1260
aaatttccaa tgggagccat gagttactgt ctcaggaca gaagcagatt tttattcaga    1320
cttccgatgg gcttatcttg tcccctccag gtacaatagt gtctcaggag gaggacattg   1380
tcacagtgac tgatgcagag gggcgtgcct gcggatgggc ccgctagaag gagttcctct   1440
agaagctgtg gagtcggtcg tcaccgcgag agccctcaca gtgaagtgga gtcagatcct   1500
agattcgtct gattttatcc agagaaggtc tatggcaagc aatgtatatt tttctaatgt   1560
gaatattgca cagatgaacc ttttatttat aaagaataat gtctttctgc cctgctgtct   1620
acatttttct atggagcttg tcataataat agcagatatt acctgatcag gaatccctgt   1680
ggcgcgtctg acgctcatga gttttcatg atggtgatga gtagcactgc actgtcacct   1740
gatgattggc cctgctccgt ttcccttctc tcctgggaga tatgctgctt ttccaccaga   1800
cttgctccat actagaagct tcttttgggt tcaattaaaa agaaaataag ctagtcattc   1860
tgggcagcat tttattgata gaagggggaa aaagtcattt ctacttgcat gattttttaa   1920
attaaattaa attaaattaa tttaaaaaa                                     1948
```

<210> SEQ ID NO 4
<211> LENGTH: 1486
<212> TYPE: DNA
<213> ORGANISM: Homo sapiens
<220> FEATURE:
<221> NAME/KEY: unsure
<222> LOCATION: 1478..1478
<223> OTHER INFORMATION: n = a, c, g or t
<220> FEATURE:
<221> NAME/KEY: unsure
<222> LOCATION: 1479..1479
<223> OTHER INFORMATION: n = a, c, g or t
<220> FEATURE:
<221> NAME/KEY: unsure
<222> LOCATION: 1486..1486
<223> OTHER INFORMATION: n = a, c, g or t

<400> SEQUENCE: 4

```
ccgcggcggc gtccggggtc tccagtaggg ctgacgctcc ggtgctcgca caatcccccg     60
cctcggctgg caacgggcgt ccctccactc ccgagtccc cggcagccgc cgccacccca    120
gcgcgccccg atctggcccc ctgccccgcg aagatggctg ccgtacgccg ggcccgcagt    180
tattgccgct gcctggtgcg cttctccgac cgagaactct gctaagctcc gctgcagaga    240
caggcaggag tagacacccg acacccagc accccctcctc cgggggggcgg tgcagagggg    300 gcacggagag cccctcgagc gcagcaggcc gccccgccag catggcagaa gctgaggaag    360
attgtcattc tgatactgtc agagcagatg atgatgaaga aaatgaaagt cctgctgaaa    420
cagatctgca ggcacaactc cagatgttcc gagctcagtg gatgtttgaa cttgctccag    480
gtgtaagctc tagcaattta gaaatcgac cttgcagagc agcaagaggc tctctccaga    540
aaacatcggc agataccaaa ggaaaacaag aacaggcaaa agaagaaaag gctcgagaac    600
tcttcctaaa agcagtagaa gaagaacaaa atggagctct ctatgaagcc atcaagtttt    660
atcgtagggc tatgcaactt gtacctgata tagagttcaa gattacttat acccggtctc    720
```

-continued

```
cagatggtga tggcgttgga acagctaca ttgaagataa tgatgatgac agcaaaatgg    780
cagatctctt gtcctacttc cagcagcaac tcacatttca ggagtctgtg cttaaactgt    840
gtcagcctga gcttgagagc agtcagattc acatatcagt gctgccaatg gaggtcctga    900
tgtacatctt ccgatgggtg gtgtctagta acttggacct cagatcattg gagcagttgt    960
cgctggtgtg cagaggattc tacatctgtg ccagagaccc tgaaatatgg cgtctggcct   1020
gcttgaaagt ttggggcaga agctgtatta aacttgttcc gtacacgtcc tggagagaga   1080
tgttttaga acgcctcgt gttcggtttg atggcgtgta tatcagtaaa accacatata    1140
ttcgtcaagg ggaacagtct cttgatggtt tctatagagc ctggcaccaa gtggaatatt   1200
acaggtacat aagattcttt cctgatggcc atgtgatgat gttgacaacc cctgaagagc   1260
ctcagtccat tgttccacgt ttaagaacta gggaatacca ggactgatgc caattctact   1320
gggtcactat cgcttggcac aagacacaga ccatcgacc caaagtattt tgctgtaata    1380
actaagaaaa aaggaagaa aaccacttg gactataaat acccgatatt tcgtcgggg     1440
tccctgtacc aaagaagccg aatcagaagt tttcatgnng gggctn               1486
```

<210> SEQ ID NO 5
<211> LENGTH: 774
<212> TYPE: DNA
<213> ORGANISM: Homo sapiens

<400> SEQUENCE: 5

```
tgcgccaccc caccccaccc cacccccgcc atgcaacggg attgaagggt cctgccggtg     60
ggaccctgtc cggcccagtg ccactgcccc ccgaggctgc tagacgtagg tgttaggcat    120
gtcccaccca cccgccgcct cccacggcac ctcggggaca ccagagctgc cgacttggag    180
actcctggtc tgtgaagagc cggtggtgcc cgtgcccgca ggaactgggc tgggcctcgt    240
gcgcccgtgg ggtctgcgct tggtctttct gtgcttggat ttgcatattt attgcattgc    300
tggtagagac ccccaggcct gtccaccctg ccaagactcc tcaggcagcg tgtgggtccc    360
gcactctgcc cccatttccc cgatgtcccc tgcgggcgcg ggcagccacc caagcctgct    420
ggctgcggcc ccctctcggc caggcattgg ctcagcccgc tgagtggggg gtcgtgggcc    480
agtccccgag gagctgggcc cctgcacagg cacacagggc ccggccacac ccagcggccc    540
cccgcacagc cacccgtggg gtgctgccct tatgcccggc gccgggcacc aactccatgt    600
ttggtgtttg tctgtgtttg ttttcaaga aatgattcaa attgctgctt ggattttgaa    660
atttactgta actgtcagtg tacacgtctg gaccccgttt catttttaca ccaatttggt    720
aaaaatgctg ctctcagcct cccacaatta accgcatgt gatctccaaa aaaa          774
```

<210> SEQ ID NO 6
<211> LENGTH: 2936
<212> TYPE: DNA
<213> ORGANISM: Homo sapiens

<400> SEQUENCE: 6

```
cgtaacccctt agtcccaatg cctccgtaag cggagttgag tgggtgcctg tggttggagc     60
tgtggaggtg tccccggtgg cgagcgcggc cagaactgcg gtcacttaag ttttccgtgt    120
gcgggttgca aggagcgtgc gtgcgtctgg tatagggagg acacctctgg attgaggatc    180
ttatgaccta ctttagagga aggtataatt tggcttcctg agattctgcc ttagcaagaa    240
aggagtggga ataccccttg gaaagaaaac taaaacagta agaaagccaa aacttatttt    300
```

-continued

```
tacatggttg tcagcacatt taccgatatg gacacttttc ccaataattt tcctcctggt    360
ggagacagtg gattgacagg ttctcagtcg gagttccaga aaatgttaat tgatgaaagg    420
ttacgatgtg agcatcataa agctaattat cagacactga aggctgaaca cacaaggttg    480
cagaatgaac atgtaaagtt acaaaatgaa ctcaagcacc tgtttaatga aaagcaaact    540
cagcaggaaa aacttcagct cctgcttgaa gaactaagag gagaattagt agagaaaact    600
aaagatttag aagaaatgaa actgcagata ttaactccca aaaattggaa ttgctaagag    660
cccaaataca acaagaatta gaaactccaa tgagagaacg ttttaggaat ctagatgaag    720
aggtagaaaa gtatagagct gtatataata agcttcgcta tgaacataca tttctcaagt    780
cagaatttga acaccagaag gaagagtatg cacgtatttt agatgaagga aaataaaat     840 atgaatcaga gattgcaaga ctggaggaag ataaagaaga actacgtaac cagctgctta    900
atgttgatct cacaaaagac agcaaacgag tggaacaact tgctcgagaa aaagtctatt    960
tgtgtcaaaa attaaaaggt ttagaggctg aagtagcgga attaaaggct gaaaaggaga   1020
attctgaggc tcaggtggaa aatgcccaaa gaatacaggt gcggcagttg gctgagatgc   1080
aggctacagt cagatccctg ggggctgaaa aacaatcagc taatttacgg gcagaacgct   1140
tggaaaaaga gctacaatca agcagtgaac aaaataccct tttaattaat aaattgcata   1200
aagctgaacg agaaataaat acattgtcca gtaaagtaaa agaacttaaa cattcaaaca   1260
aactggaaat aacagacatc aaactggaga cagcaagagc taagagtgag ctagaaagag   1320
aaaggaataa gcttcaaagt gaactggatg gattacagtc agacaatgaa attctcaaag   1380
cagctgttga acatcacaaa gtgctcttag tagaaaagga tcgtgaatta atacgtaaag   1440
tacaagctgc caaagaagaa ggttatcaaa aacttgtggt attacaagat gaaaagttag   1500
aactcgagaa cagattagca gatttggaga aaatgaaagt ggaacatgat gtctggaggc   1560
aatctgaaaa ggatcagtat gaagagaaat tgcgggcttc acagatggca gaagagatca   1620
ccaggaagga gcttcagagt gttaggttaa aacttcagca acaaattgtg actattgaaa   1680
atgcagagaa ggaaaaaaat gaaaattctg acctaaaaca gcaaatcagt agtttgcaga   1740
tccaagtgac ttcacttgca cagtcagaga atgacttgct gaattcaaac caaatgctga   1800
aggaaatggt ggagagatta aaacaagaat gccgaaattt tagaagccaa gctgaaaaag   1860
cgcaactaga agctgaaaag acattggaag agaaacagat acagtggttg aagaaaaagc   1920
ataagcttca tgaccgtatc acagacagag aagaaaagta caatcaagct aaggagaaac   1980
tgcagcgagc tgcaattgcc cagaaaaaga gaaaatctct tcatgaaaac aaattgaaaa   2040
gactacaaga gaaagtagaa gtcttggagg caaagaaaga agaattggaa acagaaatca   2100
ggtcttaaat agacaaaatg ttcctttgaa gactatacaa ggcttcaaaa aagactaaaa   2160
gatatacaga gaagacataa tgaatttcga agtctaattt tggttcctaa catgcctcca   2220
acagcatcta tcaatcctgt tagctttcag tcatcagcca tggttccaag catggaacta   2280
ccatttcctc ctcatatgca ggaggaacaa catcaaaggg aactctctct acttcgcaaa   2340
agactagaag aactggaaac aacacaaaga aaacaactag aggaacttgg atcttccgga   2400
gaatgatgtt cttggagaac aggcagatca aaagaggtga agttggtgac tcagtaaaac   2460
ttgacatttt aacctgtggc atttagatac ttttttactgt ttgccaaaac acttgaatgt   2520
gcctcaagaa aagtaccta ctacatgctg tattgtatga ctgtcaggat tttaagatta    2580
tacaagtgaa gcattaaaag agaaattctc agagatattt agaatatttg acaatggttt   2640
gagaatgtaa aacaaaaagg aactagttag agtcaagttt taaaatttt actttgttga    2700
```

| | |
|---|---|
| atttttttttt ttggcatttt gagtgaaata taactatcat taattctctc ttcatctttg | 2760 |
| agatgcttgg ccataacagg gtccatacac atcttctggt ttactatata caaaaactgt | 2820 |
| agttgaaaaa agatgacaat ttaaaagtca gcctaaagaa tgtaaaggta tctatataca | 2880 |
| aaaggctacc ttttctaaaa tctgtgtgca cataattaaa gagcttaatt tttaaa | 2936 |

<210> SEQ ID NO 7
<211> LENGTH: 1387
<212> TYPE: DNA
<213> ORGANISM: Homo sapiens

<400> SEQUENCE: 7

| | |
|---|---|
| aaaggctaca tcattaacac tagaaggagg acgattaaaa cgaactccac agctgattca | 60 |
| tggaagagac tatgaaatgg tcccagaacc tgtgtggaga gcactttatc actggtatgg | 120 |
| agcaaacctg gccttaccta gaccagttat caagaacagc aagacagaca tcccagagct | 180 |
| ggaattattt ccccgctatc ttctcttcct gagacagcag cctgccactc ggacacagca | 240 |
| gtctaacatc tgggtgaata tgggaaatgt accttctccg aatgcacctt taaagcgggt | 300 |
| attagcctat acaggctgtt ttagtcgaat gcagaccatc aaggaaattc acgaatatct | 360 |
| atctcaaagg ctgcgcatta agaggaagaa tatgcgcctg tggctataca acagtgagaa | 420 |
| ctaccttact cttctggatg atgaggatca taaattggaa tatttgaaaa tccaggatga | 480 |
| acaacacctg gtaattgaag ttcgcaacaa agatatgagt tggcctgagg agatgtctttt | 540 |
| tatagcaaat agtagtaaaa tagatagaca caaggttccc acagaaaagg gagccacagg | 600 |
| tctaagcaat ctgggaaaca catgcttcat gaactcaagc atccagtgtg ttagtaacac | 660 |
| acagccactg acacagtatt ttatctcagg gagacatctt tatgaactca acaggacaaa | 720 |
| tcccattggt atgaagggc atatggctaa atgctatggt gatttagtgc aggaactttg | 780 |
| gagtggaact cagaagaatg ttgccccatt aaagcttcgg tggaccatag caaaatatgc | 840 |
| tcccaggttt aatgggtttc agcaacagga ctcccaagaa cttctggctt ttctcttgga | 900 |
| tggtcttcat gaagatctta atcgagtcca tgaaaagcca tatgtggaac tgaaggacag | 960 |
| tgatgggcga ccagactggg aagtagctgc agaggcctgg gacaaccatc taagaagaaa | 1020 |
| tagatcaatt gttgtggatt tgttccatgg gcagctaaga tctcaagtaa aatgcaagac | 1080 |
| atgtgggcat ataagtgtcc gatttgaccc tttcaatttt ttgtctttgc cactaccaat | 1140 |
| ggacagttat atgcacttag aaataacagt gattaagtta gatggtacta cccctgtacg | 1200 |
| gtatggacta agactgaata tggatgaaaa gtacacaggt ttaaaaaaac agctgagtga | 1260 |
| tctctgtgga cttaattcag aacaaatcct tctagcagaa gtacatggtt ccaacataaa | 1320 |
| gaactttcct caggacaacc caaaaagtac cgaacttctc agtgaagtgg gattttttgg | 1380 |
| tgtgcca | 1387 |

<210> SEQ ID NO 8
<211> LENGTH: 749
<212> TYPE: DNA
<213> ORGANISM: Homo sapiens
<220> FEATURE:
<221> NAME/KEY: unsure
<222> LOCATION: 745..745
<223> OTHER INFORMATION: n = a, c, g or t

<400> SEQUENCE: 8

| | |
|---|---|
| gcccaacatg gctggagcgc ggcggaggtg agccggccgc ccgcccgcag acgccccagc | 60 |

-continued

```
ctactgcgcc cgagtcccgc ggccccagtg gcgcctcagc tctgcggtgc cgaggcccaa      120
cggctcgatc gctgcccgcc gccagcatgt tgggcgcccc ggacgagagc tccgtgcggg      180
tggctgtcag aataagacca cagcttgcca aagagaagat tgaaggatgc catatttgta      240
catctgtcac accaggagag cctcaggtct cctagggaa agataaggct tttacttttg       300
actatgtatt tgacattgac tcccagcaag agcagatcta cattcaatgt atagaaaaac      360
taattgaagg ttgctttgaa ggatacaatg ctacagtttt tgcttatgga caaactggag      420
ctggtaaaac atacacaatg gaacaggat ttgatgttaa cattgttgag gaagaactgg       480
gtattatttc tcgagctgtt aaacaccttt ttaagagtat tgaagaaaaa aaacacatag      540
caattaaaaa tgggcttcct gctccagatt ttaaagtgaa tgcccaattc ttagagctct      600
ataatgaaga ggtccttgac ttatttgata ccactcgtga tattgatgca aaaagtaaaa      660
aatcaaatat aagaattcat gaagattcaa ctggagggaa tttatactgt gggcgtttcc      720
aacacgtact gtgaatacag aatcnagag                                       749
```

<210> SEQ ID NO 9
<211> LENGTH: 686
<212> TYPE: DNA
<213> ORGANISM: Homo sapiens
<220> FEATURE:
<221> NAME/KEY: unsure
<222> LOCATION: 43..43
<223> OTHER INFORMATION: n = a, c, g or t
<220> FEATURE:
<221> NAME/KEY: unsure
<222> LOCATION: 64..64
<223> OTHER INFORMATION: n = a, c, g or t
<220> FEATURE:
<221> NAME/KEY: unsure
<222> LOCATION: 284..284
<223> OTHER INFORMATION: n = a, c, g or t
<220> FEATURE:
<221> NAME/KEY: unsure
<222> LOCATION: 404..404
<223> OTHER INFORMATION: n = a, c, g or t
<220> FEATURE:
<221> NAME/KEY: unsure
<222> LOCATION: 624..624
<223> OTHER INFORMATION: n = a, c, g or t

<400> SEQUENCE: 9

```
tggaaattat agacctagca aaaaaagatt tagagaaggt tgnaaagaaa agaaaagagg      60
aagnaaaaaa gtgtggctgg taaagaggat aatacagaca ctgaccaaga gaagaaagaa      120
gaaaagggtg tttcggaaag agaaacccaa tgaattagaa gtggaagaaa gtcaagaagt      180
gagtgatcat gaggatgaag aagaggagga ggaggaggag gaagatgaca ttgatggggg      240
tgaaagttct gatgaatcag attctgaatc agatgaaaaa gccnattatc aagcagactt      300
ggcaaacatt acttgtgaaa ttgcaattaa gcaaagctg attgatgaac tagaaaacag       360
ccagaaaaga ctgcagactc tgaaaaagca gtatgaagag aagntaatga tgctgcaaca      420
taaaattcgg gatactcagc ttgaaagaga ccaggtgctt caaaacttag gctcggtaga      480
atcttactca gaagaaaaag caaaaaaagt taggtctgaa tatgaaaaga actccaagc       540 catgaacaaa gaactgcaga gacttcaagc agctcaaaaa gaacatgcaa ggttgcttaa      600
aaatcagtct cagtatgaaa agcnattgaa gaaattgcag caggatgtga tggaaatgaa      660
aaaaacaaag gttcgcctaa tgaaaaa                                         686
```

<210> SEQ ID NO 10
<211> LENGTH: 833

<212> TYPE: DNA
<213> ORGANISM: Homo sapiens

<400> SEQUENCE: 10

```
gttcttctgt cgccggcttc agcagcccgc gcccgggcag gaatagaaga tgaacaaacc    60
cataacacca tcaacatatg tgcgctgcct caatgttgga ctaattagga agctgtcaga   120
ttttattgat cctcaagaag gatggaagaa gttagctgta gctattaaaa aaccatctgg   180
tgatgataga tacaatcagt ttcacataag gagatttgaa gcattacttc aaactggaaa   240
aagtcccact tctgaattac tgtttgactg gggcaccaca aattgcacag ttggtgatct   300
tgtggatctt tgatccaaa tgaattttt tgctcctgcg agtcttttgc tcccagatgc   360
tgttcccaaa actgctaata cactaccttc taaagaagct ataacagttc agcaaaaaca   420
gatgcctttc tgtgacaaag acaggacatt gatgacacct gtgcagaatc ttgaacaaag   480
ctatatgcca cctgactcct caagtccaga aaataaaagt ttagaagtta gtgatacacg   540
ttttcacagt ttttcatttt atgaattgaa gaatgtcaca ataactttg atgaacgacc   600
catttctgtt ggtggtaata aaatgggaga gggaggattt ggagttgtat ataaagggct   660
acgtaaataa cacaactgtg gcagtgaaag aagcttgcag caatggttga cattactact   720
gaaggaactg aaaccagcag tttgatccaa gaaaataaaa gtaatgggca aaagtggtca   780
accatggaaa aactttagta ggaacctact tgggttttct caagtggatg gga           833
```

<210> SEQ ID NO 11
<211> LENGTH: 799
<212> TYPE: DNA
<213> ORGANISM: Homo sapiens
<220> FEATURE:
<221> NAME/KEY: unsure
<222> LOCATION: 16..16
<223> OTHER INFORMATION: n = a, c, g or t
<220> FEATURE:
<221> NAME/KEY: unsure
<222> LOCATION: 117..117
<223> OTHER INFORMATION: n = a, c, g or t
<220> FEATURE:
<221> NAME/KEY: unsure
<222> LOCATION: 337..337
<223> OTHER INFORMATION: n = a, c, g or t
<220> FEATURE:
<221> NAME/KEY: unsure
<222> LOCATION: 606..606
<223> OTHER INFORMATION: n = a, c, g or t
<220> FEATURE:
<221> NAME/KEY: unsure
<222> LOCATION: 798..798
<223> OTHER INFORMATION: n = a, c, g or t

<400> SEQUENCE: 11

```
taaaaatatc cccttngatg atacctgcca ataatgatat gtcccattat tagattatgt    60
tacatgccaa agtttaaagg aatttgggca gatccagtta aggttcctta aacaacntca   120
ctttgagact gttgaaaggg cctgacctaa tccagtgaa ccccttgcaa gaagaattct   180
ccttgtaagc cttgaagaag tatgtgagag ggccacattg gctaaaacct aaaggtggcc   240
tctaggagat gagacctacc ttccagttgt cagcaagcag gaaaaaaaaa ttgggacctc   300
agttgcaacc acaaggaact gaattctgcc aaaaatntga gtcagcttag aagagtactc   360
caagcttcag atgataacca cagcctgggc tgacacctgg atttagcttt gcatgatcct   420
cagtatgaga atctatctgt tctgtgctgg acttctaata tatagaactg tgagataatg   480
ggtcacattg gctggatgtg gtggctcata cctgtaaatc ccagcacttt gggaggccga   540
```

```
ggcaggcaga tcacctgagg tcaagagttc aagaccggcc tggccaacat ggtgaaaccc    600
cgtctntact aaaaatacaa aaattagacg agcgtggtgg tggacacctg tagtcccagc    660
tgcttgggag gctgaggcag gagactagct ggaaccaggg aggtagaggt tgcagtgagc    720
tgagatcgtg ccactgcact ccagcctggg tgacagagtg agactccatc ataaataaat    780
aaataaataa atgggtcnc                                                 799
```

<210> SEQ ID NO 12
<211> LENGTH: 812
<212> TYPE: PRT
<213> ORGANISM: Homo sapiens

<400> SEQUENCE: 12

```
Met Ala Gly Gly His Cys Gly Ser Phe Pro Ala Ala Ala Gly Ser
 1               5                  10                  15

Gly Glu Ile Val Gln Leu Asn Val Gly Gly Thr Arg Phe Ser Thr Ser
            20                  25                  30

Arg Gln Thr Leu Met Trp Ile Pro Asp Ser Phe Phe Ser Ser Leu Leu
        35                  40                  45

Ser Gly Arg Ile Ser Thr Leu Arg Asp Glu Thr Gly Ala Ile Phe Ile
    50                  55                  60

Asp Arg Asp Pro Ala Ala Phe Ala Pro Ile Leu Asn Phe Leu Arg Thr
65                  70                  75                  80

Lys Glu Leu Asp Leu Arg Gly Val Ser Ile Asn Val Leu Arg His Glu
                85                  90                  95

Ala Glu Phe Tyr Gly Ile Thr Pro Leu Val Arg Arg Leu Leu Leu Cys
            100                 105                 110

Glu Glu Leu Glu Arg Ser Ser Cys Gly Ser Val Leu Phe His Gly Tyr
        115                 120                 125

Leu Pro Pro Pro Gly Ile Pro Ser Arg Lys Ile Asn Asn Thr Val Arg
    130                 135                 140

Ser Ala Asp Ser Arg Asn Gly Leu Asn Ser Thr Glu Gly Glu Ala Arg
145                 150                 155                 160

Gly Asn Gly Thr Gln Pro Val Leu Ser Gly Thr Gly Glu Glu Thr Val
                165                 170                 175

Arg Leu Gly Phe Pro Val Asp Pro Arg Lys Val Leu Ile Val Ala Gly
            180                 185                 190

His His Asn Trp Ile Val Ala Ala Tyr Ala His Phe Ala Tyr Arg Ile
        195                 200                 205

Lys Glu Ser Ser Gly Trp Gln Gln Val Phe Thr Ser Pro Tyr Leu Asp
    210                 215                 220

Trp Thr Ile Glu Arg Val Ala Leu Asn Ala Lys Val Val Gly Gly Pro
225                 230                 235                 240

His Gly Asp Lys Asp Lys Met Val Ala Val Ser Glu Ser Ser Ile
                245                 250                 255

Ile Leu Trp Ser Val Gln Asp Gly Gly Ser Ser Glu Ile Gly Val
            260                 265                 270

Phe Ser Leu Gly Val Pro Val Asp Ala Leu Phe Phe Ile Gly Asn Gln
        275                 280                 285

Leu Val Ala Thr Ser His Thr Gly Lys Val Gly Val Trp Asn Ala Val
    290                 295                 300

Thr Gln His Trp Gln Val Gln Asp Val Val Pro Ile Thr Ser Tyr Asp
305                 310                 315                 320

Thr Ala Gly Ser Phe Leu Leu Leu Gly Cys Asn Asn Gly Ser Ile Tyr
```

-continued

```
                    325                 330                 335
Tyr Ile Asp Met Gln Lys Phe Pro Leu Arg Met Lys Asp Asn Asp Leu
                340                 345                 350
Leu Val Thr Glu Leu Tyr His Asp Pro Ser Asn Asp Ala Ile Thr Ala
            355                 360                 365
Leu Ser Val Tyr Leu Thr Pro Lys Thr Ser Val Ser Gly Asn Trp Ile
        370                 375                 380
Glu Ile Ala Tyr Gly Thr Ser Ser Gly Ala Val Arg Val Ile Val Gln
385                 390                 395                 400
His Pro Glu Thr Val Gly Ser Gly Pro Gln Leu Phe Gln Thr Phe Thr
                405                 410                 415
Val His Arg Ser Pro Val Thr Lys Ile Met Leu Ser Glu Lys His Leu
                420                 425                 430
Val Ser Val Cys Ala Asp Asn Asn His Val Arg Thr Trp Thr Val Thr
            435                 440                 445
Arg Phe Gly Met Ile Ser Thr Gln Pro Gly Ser Thr Pro Leu Ala Ser
        450                 455                 460
Phe Lys Ile Leu Ser Leu Glu Glu Thr Glu Ser His Gly Ser Tyr Ser
465                 470                 475                 480
Ser Gly Asn Asp Ile Gly Pro Phe Gly Glu Arg Asp Asp Gln Gln Val
                485                 490                 495
Phe Ile Gln Lys Val Pro Ile Thr Asn Lys Leu Phe Val Arg Leu
                500                 505                 510
Ser Ser Thr Gly Lys Arg Ile Cys Glu Ile Gln Ala Val Asp Cys Thr
            515                 520                 525
Thr Ile Ser Ser Phe Thr Val Arg Glu Cys Glu Gly Ser Ser Arg Met
        530                 535                 540
Gly Ser Arg Pro Arg Arg Tyr Leu Phe Thr Gly His Thr Asn Gly Ser
545                 550                 555                 560
Ile Gln Met Trp Asp Leu Thr Thr Ala Met Asp Met Val Asn Lys Ser
                565                 570                 575
Glu Asp Lys Asp Val Gly Gly Pro Thr Glu Glu Leu Leu Lys Leu
                580                 585                 590
Leu Asp Gln Cys Asp Leu Ser Thr Ser Arg Cys Ala Thr Pro Asn Ile
            595                 600                 605
Ser Pro Ala Thr Ser Val Val Gln His Ser His Leu Arg Glu Ser Asn
        610                 615                 620
Ser Ser Leu Gln Leu Gln His His Asp Thr Thr His Glu Ala Ala Thr
625                 630                 635                 640
Tyr Gly Ser Met Arg Pro Tyr Arg Glu Ser Pro Leu Leu Ala Arg Ala
                645                 650                 655
Arg Arg Thr Glu Ser Phe His Ser Tyr Arg Asp Phe Gln Thr Ile Asn
                660                 665                 670
Leu Asn Arg Asn Val Glu Arg Ala Val Pro Glu Asn Gly Asn Leu Gly
            675                 680                 685
Pro Ile Gln Ala Glu Val Lys Gly Ala Thr Gly Glu Cys Asn Ile Ser
        690                 695                 700
Glu Arg Lys Ser Pro Gly Val Glu Ile Lys Ser Leu Arg Glu Leu Asp
705                 710                 715                 720
Ser Gly Leu Glu Val His Lys Ile Ala Glu Gly Phe Ser Glu Ser Lys
                725                 730                 735
Lys Arg Ser Ser Glu Asp Glu Asn Glu Asn Lys Ile Glu Phe Arg Lys
                740                 745                 750
```

-continued

Lys Gly Gly Phe Glu Gly Gly Phe Leu Gly Arg Lys Lys Val Pro
            755                 760                 765

Tyr Leu Ala Ser Ser Pro Ser Thr Ser Asp Gly Thr Asp Ser Pro
        770                 775                 780

Gly Thr Ala Ser Pro Ser Pro Thr Lys Thr Thr Pro Ser Pro Arg His
785                 790                 795                 800

Lys Lys Ser Asp Ser Ser Gly Gln Glu Tyr Ser Leu
                805                 810

<210> SEQ ID NO 13
<211> LENGTH: 167
<212> TYPE: PRT
<213> ORGANISM: Homo sapiens

<400> SEQUENCE: 13

Leu Ala Ser Ala Arg Ile Pro Gly Arg Pro Tyr Val Gly Val Leu Arg
1               5                   10                  15

Pro Pro Gly Ser Leu Phe Phe Ala Pro Ala Gly Thr Thr Ile Ser Ala
            20                  25                  30

Leu Leu Gly Phe Cys Tyr Met Ala Ala Phe Leu Lys Met Ser Val Ser
        35                  40                  45

Val Asn Phe Phe Arg Pro Phe Thr Arg Phe Leu Val Pro Phe Thr Leu
    50                  55                  60

His Arg Lys Arg Asn Asn Leu Thr Ile Leu Gln Arg Tyr Met Ser Ser
65                  70                  75                  80

Lys Ile Pro Ala Val Thr Tyr Pro Lys Asn Glu Ser Thr Arg Pro Ser
                85                  90                  95

Glu Glu Leu Glu Leu Asp Lys Trp Lys Thr Thr Met Lys Ser Ser Val
            100                 105                 110

Gln Glu Glu Cys Val Ser Thr Ile Ser Ser Ser Lys Asp Glu Asp Pro
        115                 120                 125

Leu Ala Ala Thr Arg Glu Phe Ile Glu Met Trp Arg Leu Leu Gly Arg
    130                 135                 140

Glu Val Pro Glu His Ile Thr Glu Glu Glu Leu Lys Thr Leu Met Glu
145                 150                 155                 160

Cys Val Ser Asn Thr Ala Lys
                165

<210> SEQ ID NO 14
<211> LENGTH: 452
<212> TYPE: PRT
<213> ORGANISM: Homo sapiens

<400> SEQUENCE: 14

Pro Cys Glu Gly Gly Ala Arg Ser Cys Leu Val Thr Glu Ser Ala Arg
1               5                   10                  15

Gly Gly Leu Gln Phe Leu Gln Gln Cys Asp Arg Glu Asp Leu Val Glu
            20                  25                  30

Leu Ala Leu Pro Gln Leu Ala Gln Val Val Thr Val Tyr Glu Phe Leu
        35                  40                  45

Leu Met Lys Val Glu Lys Asp His Leu Ala Lys Pro Phe Phe Pro Ala
    50                  55                  60

Ile Tyr Lys Glu Phe Glu Glu Leu His Lys Met Val Lys Lys Met Cys
65                  70                  75                  80

Gln Asp Tyr Leu Ser Ser Ser Gly Leu Cys Ser Gln Glu Thr Leu Glu
                85                  90                  95

Ile Asn Asn Asp Lys Val Ala Glu Ser Leu Gly Ile Thr Glu Phe Leu
            100                 105                 110

Arg Lys Lys Glu Ile His Pro Asp Asn Leu Gly Pro Lys His Leu Ser
        115                 120                 125

Arg Asp Met Asp Gly Glu Gln Leu Glu Gly Ala Ser Ser Glu Lys Arg
    130                 135                 140

Glu Arg Glu Ala Ala Glu Gly Leu Ala Ser Val Lys Arg Pro Arg
145                 150                 155                 160

Arg Glu Ala Leu Ser Asn Asp Thr Thr Glu Ser Leu Ala Ala Asn Ser
                165                 170                 175

Arg Gly Arg Glu Lys Pro Arg Pro Leu His Ala Leu Pro Ala Gly Phe
            180                 185                 190

Ser Pro Pro Val Asn Val Thr Val Ser Pro Arg Ser Glu Glu Ser His
        195                 200                 205

Thr Thr Thr Val Ser Gly Gly Asn Gly Ser Val Phe Gln Ala Gly Pro
    210                 215                 220

Gln Leu Gln Ala Leu Ala Asn Leu Glu Ala Arg Arg Gly Ser Ile Gly
225                 230                 235                 240

Ala Ala Leu Ser Ser Arg Asp Val Ser Gly Leu Pro Val Tyr Ala Gln
                245                 250                 255

Ser Gly Glu Pro Arg Arg Leu Thr Gln Ala Gln Val Ala Ala Phe Pro
            260                 265                 270

Gly Glu Asn Ala Leu Glu His Ser Ser Asp Gln Asp Thr Trp Asp Ser
        275                 280                 285

Leu Arg Ser Pro Gly Phe Cys Ser Pro Leu Ser Ser Gly Gly Gly Ala
    290                 295                 300

Glu Ser Leu Pro Pro Gly Gly Pro Gly His Ala Glu Ala Gly His Leu
305                 310                 315                 320

Gly Lys Val Cys Asp Phe His Leu Asn His Gln Pro Ser Pro Thr
                325                 330                 335

Ser Val Leu Pro Thr Glu Val Ala Ala Pro Pro Leu Glu Lys Ile Leu
            340                 345                 350

Ser Val Asp Ser Val Ala Val Asp Cys Ala Tyr Arg Thr Val Pro Lys
        355                 360                 365

Pro Gly Pro Gln Pro Gly Pro His Gly Ser Leu Leu Thr Glu Gly Cys
    370                 375                 380

Leu Arg Ser Leu Ser Gly Asp Leu Asn Arg Phe Pro Cys Gly Met Glu
385                 390                 395                 400

Val His Ser Gly Gln Arg Glu Leu Glu Ser Val Val Ala Val Gly Glu
                405                 410                 415

Ala Met Ala Leu Lys Phe Pro Met Gly Ala Met Ser Tyr Cys Leu Arg
            420                 425                 430

Asp Arg Ser Arg Phe Leu Phe Arg Leu Pro Met Gly Leu Ser Cys Pro
        435                 440                 445

Leu Gln Val Gln
    450

<210> SEQ ID NO 15
<211> LENGTH: 321
<212> TYPE: PRT
<213> ORGANISM: Homo sapiens

<400> SEQUENCE: 15

Met Ala Glu Ala Glu Glu Asp Cys His Ser Asp Thr Val Arg Ala Asp

```
  1               5                  10                 15
Asp Asp Glu Glu Asn Glu Ser Pro Ala Glu Thr Asp Leu Gln Ala Gln
                    20                 25                 30

Leu Gln Met Phe Arg Ala Gln Trp Met Phe Glu Leu Ala Pro Gly Val
            35                 40                 45

Ser Ser Ser Asn Leu Glu Asn Arg Pro Cys Arg Ala Ala Arg Gly Ser
        50                 55                 60

Leu Gln Lys Thr Ser Ala Asp Thr Lys Gly Lys Gln Glu Gln Ala Lys
 65                 70                 75                 80

Glu Glu Lys Ala Arg Glu Leu Phe Leu Lys Ala Val Glu Glu Glu Gln
                85                 90                 95

Asn Gly Ala Leu Tyr Glu Ala Ile Lys Phe Tyr Arg Arg Ala Met Gln
            100                105                110

Leu Val Pro Asp Ile Glu Phe Lys Ile Thr Tyr Thr Arg Ser Pro Asp
        115                120                125

Gly Asp Gly Val Gly Asn Ser Tyr Ile Glu Asp Asn Asp Asp Asp Ser
130                135                140

Lys Met Ala Asp Leu Leu Ser Tyr Phe Gln Gln Gln Leu Thr Phe Gln
145                150                155                160

Glu Ser Val Leu Lys Leu Cys Gln Pro Glu Leu Glu Ser Ser Gln Ile
                165                170                175

His Ile Ser Val Leu Pro Met Glu Val Leu Met Tyr Ile Phe Arg Trp
            180                185                190

Val Val Ser Ser Asp Leu Asp Leu Arg Ser Leu Glu Gln Leu Ser Leu
        195                200                205

Val Cys Arg Gly Phe Tyr Ile Cys Ala Arg Asp Pro Glu Ile Trp Arg
210                215                220

Leu Ala Cys Leu Lys Val Trp Gly Arg Ser Cys Ile Lys Leu Val Pro
225                230                235                240

Tyr Thr Ser Trp Arg Glu Met Phe Leu Glu Arg Pro Arg Val Arg Phe
                245                250                255

Asp Gly Val Tyr Ile Ser Lys Thr Thr Tyr Ile Arg Gln Gly Glu Gln
            260                265                270

Ser Leu Asp Gly Phe Tyr Arg Ala Trp His Gln Val Glu Tyr Tyr Arg
        275                280                285

Tyr Ile Arg Phe Phe Pro Asp Gly His Val Met Met Leu Thr Thr Pro
        290                295                300

Glu Glu Pro Gln Ser Ile Val Pro Arg Leu Arg Thr Arg Glu Tyr Gln
305                310                315                320

Asp

<210> SEQ ID NO 16
<211> LENGTH: 172
<212> TYPE: PRT
<213> ORGANISM: Homo sapiens

<400> SEQUENCE: 16

Ala Cys Pro Thr His Pro Pro Pro Thr Ala Pro Arg Gly His Gln
 1               5                  10                 15

Ser Cys Arg Leu Gly Asp Ser Trp Ser Val Lys Ser Arg Trp Cys Pro
                20                 25                 30

Cys Pro Gln Glu Leu Gly Trp Ala Ser Cys Ala Arg Gly Val Cys Ala
            35                 40                 45

Trp Ser Phe Cys Ala Trp Ile Cys Ile Phe Ile Ala Leu Leu Val Glu
```

```
                50                  55                  60
Thr Pro Arg Pro Val His Pro Ala Lys Thr Pro Gln Ala Ala Cys Gly
 65                  70                  75                  80

Ser Arg Thr Leu Pro Pro Phe Pro Arg Cys Pro Leu Arg Ala Arg Ala
                 85                  90                  95

Ala Thr Gln Ala Cys Trp Leu Arg Pro Pro Leu Gly Gln Ala Leu Ala
            100                 105                 110

Gln Pro Ala Glu Trp Gly Val Val Gly Gln Ser Pro Arg Ser Trp Ala
            115                 120                 125

Pro Ala Gln Ala His Arg Ala Arg Pro His Pro Ala Ala Pro Arg Thr
130                 135                 140

Ala Thr Arg Gly Val Leu Pro Leu Cys Pro Ala Pro Gly Thr Asn Ser
145                 150                 155                 160

Met Phe Gly Val Cys Leu Cys Leu Phe Phe Lys Lys
                165                 170

<210> SEQ ID NO 17
<211> LENGTH: 472
<212> TYPE: PRT
<213> ORGANISM: Homo sapiens

<400> SEQUENCE: 17

Met Arg Glu Arg Phe Arg Asn Leu Asp Glu Val Glu Lys Tyr Arg
 1               5                  10                  15

Ala Val Tyr Asn Lys Leu Arg Tyr Glu His Thr Phe Leu Lys Ser Glu
                 20                  25                  30

Phe Glu His Gln Lys Glu Glu Tyr Ala Arg Ile Leu Asp Glu Gly Lys
             35                  40                  45

Ile Lys Tyr Glu Ser Glu Ile Ala Arg Leu Glu Glu Asp Lys Glu Glu
 50                  55                  60

Leu Arg Asn Gln Leu Leu Asn Val Asp Leu Thr Lys Asp Ser Lys Arg
 65                  70                  75                  80

Val Glu Gln Leu Ala Arg Glu Lys Val Tyr Leu Cys Gln Lys Leu Lys
                 85                  90                  95

Gly Leu Glu Ala Glu Val Ala Glu Leu Lys Ala Glu Lys Glu Asn Ser
            100                 105                 110

Glu Ala Gln Val Glu Asn Ala Gln Arg Ile Gln Val Arg Gln Leu Ala
            115                 120                 125

Glu Met Gln Ala Thr Val Arg Ser Leu Gly Ala Glu Lys Gln Ser Ala
            130                 135                 140

Asn Leu Arg Ala Glu Arg Leu Glu Lys Glu Leu Gln Ser Ser Ser Glu
145                 150                 155                 160

Gln Asn Thr Phe Leu Ile Asn Lys Leu His Lys Ala Glu Arg Glu Ile
                165                 170                 175

Asn Thr Leu Ser Ser Lys Val Lys Glu Leu Lys His Ser Asn Lys Leu
                180                 185                 190

Glu Ile Thr Asp Ile Lys Leu Glu Thr Ala Arg Ala Lys Ser Glu Leu
            195                 200                 205

Glu Arg Glu Arg Asn Lys Leu Gln Ser Glu Leu Asp Gly Leu Gln Ser
210                 215                 220

Asp Asn Glu Ile Leu Lys Ala Ala Val Glu His His Lys Val Leu Leu
225                 230                 235                 240

Val Glu Lys Asp Arg Glu Leu Ile Arg Lys Val Gln Ala Ala Lys Glu
                245                 250                 255
```

-continued

```
Glu Gly Tyr Gln Lys Leu Val Val Leu Gln Asp Glu Lys Leu Glu Leu
            260                 265                 270

Glu Asn Arg Leu Ala Asp Leu Glu Lys Met Lys Val Glu His Asp Val
            275                 280                 285

Trp Arg Gln Ser Glu Lys Asp Gln Tyr Glu Glu Lys Leu Arg Ala Ser
            290                 295                 300

Gln Met Ala Glu Glu Ile Thr Arg Lys Glu Leu Gln Ser Val Arg Leu
305                 310                 315                 320

Lys Leu Gln Gln Gln Ile Val Thr Ile Glu Asn Ala Glu Lys Glu Lys
                    325                 330                 335

Asn Glu Asn Ser Asp Leu Lys Gln Gln Ile Ser Ser Leu Gln Ile Gln
                340                 345                 350

Val Thr Ser Leu Ala Gln Ser Glu Asn Asp Leu Leu Asn Ser Asn Gln
            355                 360                 365

Met Leu Lys Glu Met Val Glu Arg Leu Lys Gln Glu Cys Arg Asn Phe
            370                 375                 380

Arg Ser Gln Ala Glu Lys Ala Gln Leu Glu Ala Glu Lys Thr Leu Glu
385                 390                 395                 400

Glu Lys Gln Ile Gln Trp Leu Glu Glu Lys His Lys Leu His Asp Arg
                    405                 410                 415

Ile Thr Asp Arg Glu Glu Lys Tyr Asn Gln Ala Lys Glu Lys Leu Gln
                420                 425                 430

Arg Ala Ala Ile Ala Gln Lys Lys Arg Lys Ser Leu His Glu Asn Lys
            435                 440                 445

Leu Lys Arg Leu Gln Glu Lys Val Glu Val Leu Glu Ala Lys Lys Glu
            450                 455                 460

Glu Leu Glu Thr Glu Ile Arg Ser
465                 470

<210> SEQ ID NO 18
<211> LENGTH: 462
<212> TYPE: PRT
<213> ORGANISM: Homo sapiens

<400> SEQUENCE: 18

Lys Ala Thr Ser Leu Thr Leu Glu Gly Gly Arg Leu Lys Arg Thr Pro
1               5                   10                  15

Gln Leu Ile His Gly Arg Asp Tyr Glu Met Val Pro Glu Pro Val Trp
                20                  25                  30

Arg Ala Leu Tyr His Trp Tyr Gly Ala Asn Leu Ala Leu Pro Arg Pro
            35                  40                  45

Val Ile Lys Asn Ser Lys Thr Asp Ile Pro Glu Leu Glu Leu Phe Pro
    50                  55                  60

Arg Tyr Leu Leu Phe Leu Arg Gln Gln Pro Ala Thr Arg Thr Gln Gln
65              70                  75                  80

Ser Asn Ile Trp Val Asn Met Gly Asn Val Pro Ser Pro Asn Ala Pro
                85                  90                  95

Leu Lys Arg Val Leu Ala Tyr Thr Gly Cys Phe Ser Arg Met Gln Thr
            100                 105                 110

Ile Lys Glu Ile His Glu Tyr Leu Ser Gln Arg Leu Arg Ile Lys Glu
        115                 120                 125

Glu Asp Met Arg Leu Trp Leu Tyr Asn Ser Glu Asn Tyr Leu Thr Leu
    130                 135                 140

Leu Asp Asp Glu Asp His Lys Leu Glu Tyr Leu Lys Ile Gln Asp Glu
145                 150                 155                 160
```

```
Gln His Leu Val Ile Glu Val Arg Asn Lys Asp Met Ser Trp Pro Glu
                165                 170                 175

Glu Met Ser Phe Ile Ala Asn Ser Ser Lys Ile Asp Arg His Lys Val
            180                 185                 190

Pro Thr Glu Lys Gly Ala Thr Gly Leu Ser Asn Leu Gly Asn Thr Cys
        195                 200                 205

Phe Met Asn Ser Ser Ile Gln Cys Val Ser Asn Thr Gln Pro Leu Thr
    210                 215                 220

Gln Tyr Phe Ile Ser Gly Arg His Leu Tyr Glu Leu Asn Arg Thr Asn
225                 230                 235                 240

Pro Ile Gly Met Lys Gly His Met Ala Lys Cys Tyr Gly Asp Leu Val
                245                 250                 255

Gln Glu Leu Trp Ser Gly Thr Gln Lys Asn Val Ala Pro Leu Lys Leu
            260                 265                 270

Arg Trp Thr Ile Ala Lys Tyr Ala Pro Arg Phe Asn Gly Phe Gln Gln
        275                 280                 285

Gln Asp Ser Gln Glu Leu Leu Ala Phe Leu Leu Asp Gly Leu His Glu
    290                 295                 300

Asp Leu Asn Arg Val His Glu Lys Pro Tyr Val Glu Leu Lys Asp Ser
305                 310                 315                 320

Asp Gly Arg Pro Asp Trp Glu Val Ala Ala Glu Ala Trp Asp Asn His
                325                 330                 335

Leu Arg Arg Asn Arg Ser Ile Val Val Asp Leu Phe His Gly Gln Leu
            340                 345                 350

Arg Ser Gln Val Lys Cys Lys Thr Cys Gly His Ile Ser Val Arg Phe
        355                 360                 365

Asp Pro Phe Asn Phe Leu Ser Leu Pro Leu Pro Met Asp Ser Tyr Met
    370                 375                 380

His Leu Glu Ile Thr Val Ile Lys Leu Asp Gly Thr Thr Pro Val Arg
385                 390                 395                 400

Tyr Gly Leu Arg Leu Asn Met Asp Glu Lys Tyr Thr Gly Leu Lys Lys
                405                 410                 415

Gln Leu Ser Asp Leu Cys Gly Leu Asn Ser Glu Gln Ile Leu Leu Ala
            420                 425                 430

Glu Val His Gly Ser Asn Ile Lys Asn Phe Pro Gln Asp Asn Pro Lys
        435                 440                 445

Ser Thr Glu Leu Leu Ser Glu Val Gly Phe Phe Gly Val Pro
    450                 455                 460

<210> SEQ ID NO 19
<211> LENGTH: 243
<212> TYPE: PRT
<213> ORGANISM: Homo sapiens

<400> SEQUENCE: 19

Pro Thr Trp Leu Glu Arg Gly Gly Glu Pro Ala Ala Arg Pro Gln
1               5                   10                  15

Thr Pro Gln Pro Thr Ala Pro Glu Ser Arg Gly Pro Ser Gly Ala Ser
            20                  25                  30

Ala Leu Arg Cys Arg Gly Pro Thr Ala Arg Ser Leu Pro Ala Ala Ser
        35                  40                  45

Met Leu Gly Ala Pro Asp Glu Ser Ser Val Arg Val Ala Val Arg Ile
    50                  55                  60

Arg Pro Gln Leu Ala Lys Glu Lys Ile Glu Gly Cys His Ile Cys Thr
```

-continued

```
            65                  70                  75                  80
Ser Val Thr Pro Gly Glu Pro Gln Val Phe Leu Gly Lys Asp Lys Ala
                85                  90                  95

Phe Thr Phe Asp Tyr Val Phe Asp Ile Asp Ser Gln Gln Glu Gln Ile
               100                 105                 110

Tyr Ile Gln Cys Ile Glu Lys Leu Ile Glu Gly Cys Phe Glu Gly Tyr
               115                 120                 125

Asn Ala Thr Val Phe Ala Tyr Gly Gln Thr Gly Ala Gly Lys Thr Tyr
       130                 135                 140

Thr Met Gly Thr Gly Phe Asp Val Asn Ile Val Glu Glu Leu Gly
145                 150                 155                 160

Ile Ile Ser Arg Ala Val Lys His Leu Phe Lys Ser Ile Glu Lys
               165                 170                 175

Lys His Ile Ala Ile Lys Asn Gly Leu Pro Ala Pro Asp Phe Lys Val
               180                 185                 190

Asn Ala Gln Phe Leu Glu Leu Tyr Asn Glu Glu Val Leu Asp Leu Phe
       195                 200                 205

Asp Thr Thr Arg Asp Ile Asp Ala Lys Ser Lys Ser Asn Ile Arg
       210                 215                 220

Ile His Glu Asp Ser Thr Gly Gly Asn Leu Tyr Cys Gly Arg Phe Gln
225                 230                 235                 240

His Val Leu

<210> SEQ ID NO 20
<211> LENGTH: 223
<212> TYPE: PRT
<213> ORGANISM: Homo sapiens

<400> SEQUENCE: 20

Gly Asn Tyr Arg Pro Ser Lys Lys Arg Phe Arg Glu Gly Lys Glu Lys
  1               5                  10                  15

Lys Arg Gly Lys Lys Val Trp Leu Val Lys Arg Ile Ile Gln Thr Leu
                20                  25                  30

Thr Lys Arg Arg Lys Lys Lys Arg Val Phe Arg Lys Glu Lys Pro Asn
        35                  40                  45

Glu Leu Glu Val Glu Glu Ser Gln Glu Val Ser Asp His Glu Asp Glu
 50                  55                  60

Glu Glu Glu Glu Glu Glu Glu Asp Asp Ile Asp Gly Gly Glu Ser
65                  70                  75                  80

Ser Asp Glu Ser Asp Ser Glu Ser Asp Glu Lys Ala Tyr Gln Ala Asp
                85                  90                  95

Leu Ala Asn Ile Thr Cys Glu Ile Ala Ile Lys Gln Lys Leu Ile Asp
               100                 105                 110

Glu Leu Glu Asn Ser Gln Lys Arg Leu Gln Thr Leu Lys Lys Gln Tyr
               115                 120                 125

Glu Glu Lys Met Met Leu Gln His Lys Ile Arg Asp Thr Gln Leu Glu
       130                 135                 140

Arg Asp Gln Val Leu Gln Asn Leu Gly Ser Val Glu Ser Tyr Ser Glu
145                 150                 155                 160

Glu Lys Ala Lys Lys Val Arg Ser Glu Tyr Glu Lys Lys Leu Gln Ala
               165                 170                 175

Met Asn Lys Glu Leu Gln Arg Leu Gln Ala Ala Gln Lys Glu His Ala
       180                 185                 190

Arg Leu Leu Lys Asn Gln Ser Gln Tyr Glu Lys Leu Lys Lys Leu Gln
```

```
            195                 200                 205
Gln Asp Val Met Glu Met Lys Thr Lys Val Arg Leu Met Lys
    210                 215                 220
```

<210> SEQ ID NO 21
<211> LENGTH: 206
<212> TYPE: PRT
<213> ORGANISM: Homo sapiens

<400> SEQUENCE: 21

```
Met Asn Lys Pro Ile Thr Pro Ser Thr Tyr Val Arg Cys Leu Asn Val
1               5                   10                  15

Gly Leu Ile Arg Lys Leu Ser Asp Phe Ile Asp Pro Gln Glu Gly Trp
            20                  25                  30

Lys Lys Leu Ala Val Ala Ile Lys Lys Pro Ser Gly Asp Asp Arg Tyr
                35                  40                  45

Asn Gln Phe His Ile Arg Arg Phe Glu Ala Leu Leu Gln Thr Gly Lys
            50                  55                  60

Ser Pro Thr Ser Glu Leu Leu Phe Asp Trp Gly Thr Thr Asn Cys Thr
65                  70                  75                  80

Val Gly Asp Leu Val Asp Leu Leu Ile Gln Asn Glu Phe Phe Ala Pro
                85                  90                  95

Ala Ser Leu Leu Leu Pro Asp Ala Val Pro Lys Thr Ala Asn Thr Leu
            100                 105                 110

Pro Ser Lys Glu Ala Ile Thr Val Gln Gln Lys Gln Met Pro Phe Cys
        115                 120                 125

Asp Lys Asp Arg Thr Leu Met Thr Pro Val Gln Asn Leu Glu Gln Ser
    130                 135                 140

Tyr Met Pro Pro Asp Ser Ser Pro Glu Asn Lys Ser Leu Glu Val
145                 150                 155                 160

Ser Asp Thr Arg Phe His Ser Phe Ser Phe Tyr Glu Leu Lys Asn Val
                165                 170                 175

Thr Asn Asn Phe Asp Glu Arg Pro Ile Ser Val Gly Gly Asn Lys Met
            180                 185                 190

Gly Glu Gly Gly Phe Gly Val Val Tyr Lys Gly Leu Arg Lys
        195                 200                 205
```

<210> SEQ ID NO 22
<211> LENGTH: 1260
<212> TYPE: DNA
<213> ORGANISM: Homo sapiens

<400> SEQUENCE: 22

```
cttctccgca cgactgttac agaggtctcc agagccttct ctctcctgtg caaaatggca     60
actcttaagg aaaaactcat tgcaccagtt gcggaagaag aggcaacagt tccaaacaat    120
aagatcactg tagtgggtgt tggacaagtt ggtatggcgt gtgctatcag cattctggga    180
aagtctctgg ctgatgaact tgctcttgtg gatgttttgg aagataagct taaggagaa    240 atgatggatc tgcagcatgg gagcttattt cttcagacac ctaaaattgt ggcagataaa    300
gattattctg tgaccgccaa ttctaagatt gtagtggtaa ctgcaggagt ccgtcagcaa    360
gaaggggaga gtcggctcaa tctggtgcag agaaatgtta atgtcttcaa attcattatt    420
cctcagatcg tcaagtacag tcctgattgc atcataattg tggtttccaa cccagtggac    480
attcttacgt atgttacctg gaaactaagt ggattaccca acaccgcgt gattggaagt    540 ggatgtaatc tggattctgc tagatttcgc taccttatgg ctgaaaaact tggcattcat    600
```

-continued

```
cccagcagct gccatggatg gattttgggg gaacatggcg actcaagtgt ggctgtgtgg      660
agtggtgtga atgtggcagg tgtttctctc caggaattga atccagaaat gggaactgac      720
aatgatagtg aaaattggaa ggaagtgcat aagatggtgg ttgaaagtgc ctatgaagtc      780
atcaagctaa aaggatatac caactgggct attggattaa gtgtggctga tcttattgaa      840
tccatgttga aaaatctatc caggattcat cccgtgtcaa caatggtaaa ggggatgtat      900
ggcattgaga atgaagtctt cctgagcctt ccatgtatcc tcaatgcccg gggattaacc      960
agcgttatca accagaagct aaaggatgat gaggttgctc agctcaagaa aagtgcagat     1020
accctgtggg acatccagaa ggacctaaaa gacctgtgac tagtgagctc taggctgtag     1080
aaatttaaaa actacaatgt gattaactcg agcctttagt tttcatccat gtacatggat     1140
cacagtttgc tttgatcttc ttcaatatgt gaatttgggc tcacagaatc aaagcctatg     1200
cttggtttaa tgcttgcaat ctgagctctt gaacaaataa aattaactat tgtagtgtga     1260
```

<210> SEQ ID NO 23
<211> LENGTH: 3150
<212> TYPE: DNA
<213> ORGANISM: Homo sapiens

<400> SEQUENCE: 23

```
taacacagtt gtgaaaagag atggatgtgg gttccagtcc tagccctgcc tgtgtgcact       60
tatgcagaaa cgctaatgga ctccactaca gcgactgctg agctgggctg atggtgcat      120 cctccatcag ggtgggaaga ggtgagtggc tacgatgaga acatgaacac gatccgcacg      180
taccaggtgt gcaacgtgtt tgagtcaagc cagaacaact ggctacggac caagtttatc      240
cggcgccgtg gcgcccaccg catccacgtg gagatgaagt tttcggtgcg tgactgcagc      300
agcatcccca gcgtgcctgg ctcctgcaag gagaccttca acctctatta ctatgaggct      360
gactttgact cggccaccaa gaccttcccc aactggatgg agaatccatg ggtgaaggtg      420
gataccattg cagccgacga gagcttctcc caggtggacc tgggtgaccg cgtcatgaaa      480
atcaacaccg aggtgcggag cttcggacct gtgtcccgca gcggcttcta cctggccttc      540
caggactatg gcggctgcat gtccctcatc gccgtgcgtg tcttctaccg caagtgcccc      600
cgcatcatcc agaatggcgc catcttccag gaaaccctgt cggggctga gagcacatcg      660 ctggtggctg cccggggcag ctgcatcgcc aatgcggaag aggtggatgt acccatcaag      720
ctctactgta acgggacgg cgagtggctg gtgcccatcg ggcgctgcat gtgcaaagca      780
ggcttcgagg ccgttgagaa tggcaccgtc tgccgaggtt gtccatctgg gactttcaag     840
gccaaccaag gggatgaggc ctgtacccac tgtcccatca acagccggac cacttctgaa      900
ggggccacca actgtgtctg ccgcaatggc tactacagag cagacctgga ccccctggac      960
atgccctgca aaccatccc ctccgcgccc caggctgtga tttccagtgt caatgagacc     1020
tccctcatgc tggagtggac ccctcccgc gactccggag ccgagagga cctcgtctac     1080 aacatcatct gcaagagctg tggctcgggc cggggtgcct gcacccgctg cggggacaat     1140
gtacagtacg caccacgcca gctaggcctg accgagccac gcatttacat cagtgacctg     1200
ctggcccaca cccagtacac cttcgagatc caggctgtga acggcgttac tgaccagagc     1260
cccttctcgc ctcagttcgc ctctgtgaac atcaccacca accaggcagc tccatcggca     1320
gtgtccatca tgcatcaggt gagccgcacc gtggacagca ttaccctgtc gtggtcccag     1380
ccagaccagc ccaatggcgt gatcctggac tatgagctgc agtactatga aagcaggag     1440
```

```
ctcagtgagt acaacgccac agccataaaa agccccacca acacggtcac cgtgcagggc    1500
ctcaaagccg gcgccatcta tgtcttccag gtgcgggcac gcaccgtggc aggctacggg    1560
cgctacagcg gcaagatgta cttccagacc atgacagaag ccgattacca gacaagcatc    1620
caggagaagt tgccactcat catcggctcc tcggccgctg gcctggtctt cctcattgct    1680
gtggttgtca tcgccatcgt gtgtaacaga cgggggtttg agcgtgctga ctcggagtac    1740
acggacaagc tgcaacacta ccagtggcc cacatgaccc caggcatgaa gatctacatc     1800 gatccttca cctacgagga ccccaacgag gcagtgcggg agtttgccaa ggaaattgac    1860
atctcctgtg tcaaaattga gcaggtgatc ggagcagggg agtttggcga ggtctgcagt    1920
ggccacctga agctgccagg caagagagag atctttgtgg ccatcaagac gctcaagtcg    1980
ggctacacgg agaagcagcg ccgggacttc ctgagcgaag cctccatcat gggccagttc    2040
gaccatccca acgtcatcca cctggagggt gtcgtgacca agagcacacc tgtgatgatc    2100
atcaccgagt tcatggagaa tggctccctg gactcctttc tccggcaaaa cgatgggcag    2160
ttcacagtca tccagctggt gggcatgctt cggggcatcg cagctggcat gaagtacctg    2220
gcagacatga actatgttca ccgtgacctg gctgcccgca acatcctcgt caacagcaac    2280
ctggtctgca aggtgtcgga ctttgggctc tcacgctttc tagaggacga tacctcagac    2340
cccacctaca ccagtgccct gggcggaaag atccccatcc gctggacagc cccggaagcc    2400
atccagtacc ggaagttcac ctcggccagt gatgtgtgga gctacggcat tgtcatgtgg    2460
gaggtgatgt cctatgggga gcggccctac tgggacatga ccaaccagga tgtaatcaat    2520
gccattgagc aggactatcg gctgccaccg cccatggact gccagctgc cctgcaccaa    2580 ctcatgctgg actgttggca aggaccgc aaccaccggc caagttcgg ccaaattgtc       2640 aacacgctag acaagatgat ccgcaatccc aacagcctca agccatggc gcccctctcc    2700 tctggcatca acctgccgct gctggaccgc acgatcccg actacaccag ctttaacacg     2760
gtggacgagt ggctgaaggc catcaagatg gggcagtaca aggagagctt cgccaatgcc    2820
ggcttcacct ccttttgacgt cgtgtctcag atgatgatgg aggacattct ccgggttggg    2880
gtcactttgg ctggccacca gaaaaaaatc ctgaacagta ccaggtgat gcgggcgcag     2940 atgaaccaga ttcagtctgt ggaggtttga cattcacctg cctcggctca cctcttcctc    3000
caagccccgc cccctctgcc ccacgtgccg gccctcctgg tgctctatcc actgcagggc    3060
cagccactcg ccaggaggcc acgggcacgg gaagaaccaa gcggtgccag ccacgagacg    3120
tcaccaagaa aacatgcaac tcaaacgacg                                    3150
```

<210> SEQ ID NO 24
<211> LENGTH: 1234
<212> TYPE: DNA
<213> ORGANISM: Homo sapiens

<400> SEQUENCE: 24

```
tagttcaaga caacagagac aaagctaaga tgaggaagtt ctgtacagtt taggaaatag      60
aggctttcaa agataattcg cagtgatgtg aaactggcct cccaagccct gataacaaca     120
tggccaacgc cctggccagc gccacttgcg agcgctgcaa gggcggcttt gcgcccgctg     180
agaagatcgt gaacagtaat ggggagctgt accatgagca gtgtttcgtg tgcgctcagt     240
gcttccagca gttcccagaa ggactcttct atgagtttga aggaagaaag tactgtgaac     300
atgactttca gatgctcttt gccccttgct gtcatcagtg tggtgaattc atcattggcc     360
gagttatcaa agccatgaat aacagctggc atccggagtg cttccgctgt gacctctgcc    420
```

```
aggaagttct ggcagatatc gggtttgtca agaatgctgg gagacacctg tgtcgcccct      480
gtcataatcg tgagaaagcc agaggccttg ggaaatacat ctgccagaaa tgccatgcta      540
tcatcgatga gcagcctctg atattcaaga acgacccta ccatccagac catttcaact      600
gcgccaactg cgggaaggag ctgactgccg atgcacggga gctgaaaggg gagctatact      660
gcctcccatg ccatgataaa atgggggtcc ccatctgtgg tgcttgccga cggcccatcg      720
aagggcgcgt ggtgaacgct atgggcaagc agtggcatgt ggagcatttt gtttgtgcca      780
agtgtgagaa acccttcttt ggacatcgcc attatgagag gaaaggcctg gcatattgtg      840
aaactcacta taaccagcta tttggtgatg tttgcttcca ctgcaatcgt gttatagaag      900
gtgatgtggt ctctgctctt aataaggcct ggtgcgtgaa ctgctttgcc tgttctacct      960
gcaacactaa attaacactc aagaataagt tgtggagtt tgacatgaag ccagtctgta     1020
agaagtgcta tgagatttcc attggagctg aagaaaagac ttaagaaact agctgagacc     1080
ttaggaagga ataagttcc tttattttt cttttctatg caagataaga gattaccaac     1140
attacttgtc ttgatctacc catatttaaa gctatatctc aaagcagttg agagaagagg     1200
acctatatga atggttttat gtcattttt taaa                                 1234

<210> SEQ ID NO 25
<211> LENGTH: 4534
<212> TYPE: DNA
<213> ORGANISM: Homo sapiens

<400> SEQUENCE: 25
gtcacgagcg tcgaagagac aaagccgcgt caggggcccc ggccggggcg ggggagcccg       60
gggcttgttg gtgccccagc ccgcgcggag ggcccttcgg accgcgcgc cgccgctgcc      120 gccgccgccg cctcgcaaca ggtccgggcg gcctcgctct ccgctcccct ccccgcatc      180 cgcgaccctc cggggcacct cagctcggcc ggggccgcag tctggccacc cgcttccatg      240
cggttcgggt ccaagatgat gccgatgttt cttaccgtgt atctcagtaa caatgagcag      300
cacttcacag aagttccagt tactccagaa acaatatgca gagacgtggt ggatctgtgc      360
aaagaacccg cgagagtga ttgccatttg gctgaagtgt ggtgtggctc tgtagagata      420
gagtttcatc atgttggcca ggatggtctc gatctcctga ccttgtgatc cgcctgcctc      480
ggcctcccaa agtgctggat tacaggtgtg agccaccacg atcagcctct agtgtttaaa      540
aaagaacgtc cagttgcgga taatgagcga atgtttgatg ttcttcaacg atttggaagt      600
cagaggaacg aagttcgctt cttccttcgt catgaacgcc ccctggcag ggacattgtg      660 agtggaccaa gatctcagga tccaagttta aaagaaatg gtgtaaaagt tcctggtgaa      720
tatcgaagaa aggagaacgg tgttaatagt cctaggatgg atctgactct tgctgaactt      780
caggaaatgg catctcgcca gcagcaacag attgaagccc agcaacaatt gctggcaact      840
aaggaacagc gcttaaagtt tttgaaacaa caagatcagc gacaacagca acaagttgct      900
gagcaggaga aacttaaaag gctaaaagaa atagctgaga tcaggaagc taagctaaaa      960 aaagtgagag cacttaaagg ccacgtggaa cagaagagac taagcaatgg gaaacttgtg     1020
gaggaaattg aacagatgaa taatttgttc cagcaaaaac agagggagct cgtcctggct     1080
gtgtcaaaag tagaagaact gaccaggcag ctagagatgc tcaagaacgg caggatcgac     1140
agccaccatg acaatcagtc tgcagtggct gagcttgatc gcctctataa ggagctgcag     1200
ctaagaaaca aattgaatca agagcagaat gccaagctac aacaacagag ggagtgtttg     1260
```

-continued

```
aataagcgta attcagaagt ggcagtcatg gataagcgtg ttaatgagct gagggaccgg    1320
ctgtggaaga agaaggcagc tctacagcaa aaagaaaatc taccagtttc atctgatgga    1380
aatcttcccc agcaagccgc gtcagcccca agccgtgtgg ctgcagtagg tccctatatc    1440
cagtcatcta ctatgcctcg gatgccctca aggcctgaat tgctggtgaa gccagccctg    1500
ccggatggtt ccttggtcat tcaggcttca gaggggccga tgaaaataca gacactgccc    1560
aacatgagat ctggggctgc ttcacaaact aaaggctcta aaatccatcc agttggccct    1620
gattggagtc cttcaaatgc agatcttttc ccaagccaag gctctgcttc tgtacctcaa    1680
agcactggga atgctctgga tcaagttgat gatggagagg ttccgctgag ggagaaagag    1740
aagaaagtgc gtccgttctc aatgtttgat gcagtagacc agtccaatgc ccaccttcc     1800 tttggtactc tgaggaagaa ccagagcagt gaagatatct tgcgggatgc tcaggttgca    1860
aataaaaatg tggctaaagt accacctcct gttcctacaa aaccaaaaca gattaatttg    1920
ccttattttg gacaaactaa tcagccacct tcagacatta gccagacgg aagttctcag     1980 cagttgtcaa cagttgttcc gtccatggga actaaaccaa aaccagcagg gcagcagccg    2040
agagtgctgc tatctcccag catacctteg gttggccaag accagaccct ttctccaggt    2100
tctaagcaag aaagtccacc tgctgctgcc gtccggccct ttactcccca gccttccaaa    2160
gacaccttac ttccaccctt cagaaaaccc cagaccgtgg cagcaagttc aatatattcc    2220
atgtatacgc aacagcaggc gccaggaaaa aacttccagc aggctgtgca gagcgcgttg    2280
accaagactc ataccagagg gccacacttt tcaagtgtat atggtaagcc tgtaattgct    2340
gctgcccaga tcaacagca gcacccagag aacatttatt ccaatagcca gggcaagcct     2400
ggcagtccag aacctgaaac agagcctgtt tcttcagttc aggagaacca tgaaaacgaa    2460
agaattcctc ggccactcag cccaactaaa ttactgcctt tcttatctaa tccttaccga    2520
aaccagagtg atgctgacct agaagcctta cgaaagaaac tgtctaacgc accaaggcct    2580
ctaaagaaac gtagttctat tacagagcca gagggtccta atgggccaaa tattcagaag    2640
cttttatatc agaggaccac catagcggcc atggagacca tctctgtccc atcataccca    2700
tccaagtcag cttctgtgac tgccagctca gaaagcccag tagaaatcca gaatccatat    2760
ttacatgtgg agcccgaaaa ggaggtggtc tctctggttc ctgaatcatt gtccccagag    2820
gatgtgggga atgccagtac agagaacagt gacatgccag ctccttctcc aggccttgat    2880
tatgagcctg agggagtccc agacaacagc ccaaatctcc agaataaccc agaagaacca    2940
aatccagagg ctccacatgt gcttgatgtg tacctggagg agtaccctcc atacccaccc    3000
ccaccatacc catctgggga gcctgaaggg cccgagaag actcggtgag catgcgcccg     3060
cctgaaatca ccgggcaggt ctctctgcct cctggtaaaa ggacaaactt gcgtaaaact    3120
ggctcagagc gtatcgctca tggaatgagg gtgaaattca accccctttgc tttactgcta    3180 gattcgtctt tggagggaga atttgacctt gtacagagaa ttatttatga ggttgatgac    3240
ccaagcctgc ccaatgatga aggcatcacg gctcttcaca atgctgtgtg tgcaggccac    3300
acagaaatcg ttaagttcct ggtacagttt ggtgtaaatg taaatgctgc tgatagtgat    3360
ggatggactc cattacattg tgctgcctca tgtaacaacg tccaagtgtg taagtttttg    3420
gtggagtcag gagccgctgt gtttgccatg acctacagtg acatgcagac tgctgcagat    3480
aagtgcgagg aaatggagga aggctacact cagtgctccc aatttcttta tggagttcag    3540
gagaagatgg gcataatgaa taaggagtc atttatgcgc tttgggatta tgaacctcag     3600
aatgatgatg agctgcccat gaaagaagga gactgcatga caatcatcca cagggaagac    3660
```

-continued

```
gaagatgaaa tcgaatggtg gtgggcgcgc cttaatgata aggagggata tgttccacgt    3720
aacttgctgg gactgtaccc aagaattaaa ccaagacaaa ggagcttggc ctgaaacttc    3780
cacacagaat tttagtcaat gaagaattaa tctctgttaa gaagaagtaa tacgattatt    3840
tttggcaaaa atttcacaag acttatttta atgacaatgt agcttgaaag cgatgaagaa    3900
tgtctctaga agagaatgaa ggattgaaga attcaccatt agaggacatt tagcgtgatg    3960
aaataaagca tctacgtcag caggccatac tgtgttgggg caaaggtgtc ccgtgtagca    4020
ctcagataag tatacagcga caatcctgtt ttctacaaga atcctgtcta gtaaatagga    4080
tcatttattg ggcagttggg aaatcagctc tctgtcctgt tgagtgtttt cagcagctgc    4140
tcctaaacca gtcctcctgc cagaaaggac cagtgccgtc acatcgctgt ctctgattgt    4200
ccccggcacc agcaggcctt ggggctcact gaaggctcga aggcactgca caccttgtat    4260
attgtcagtg aagaacgtta gttggttgtc agtgaacaat aactttatta tatgagtttt    4320
tgtagcatct aagaattat acatatgttt gaaatattga aactaagcta cagtaccagt    4380
aattagatgt agaatcttgt ttgtaggctg aattttaatc tgtatttatt gtcttttgta    4440
tctcagaaat tagaaacttg ctacagactt acccgtaata tttgtcaaga tcatagctga    4500 cttaaaaac agttgtaata aacttttga tgct                                  4534
```

<210> SEQ ID NO 26
<211> LENGTH: 4660
<212> TYPE: DNA
<213> ORGANISM: Homo sapiens

<400> SEQUENCE: 26

```
ggggcttaga aattaacagg ttgtttatat aattggcctt aaatgaggtg agagtgaaga      60
gactagagcc atctctggaa aacatcatta tcccattccc cgggaagcta ccctctggaa     120
ctcaagattt gaccatatct gttttgagga ttcattatga acaaagaagt ctcccaggtg     180
tgaagttttt caacatgagt ggcctcgggg acagttcatc cgaccctgct aacccagact     240
cacataagag gaaaggatcg ccatgtgaca cactggcatc aagcacggaa aagaggcgca     300
gggagcaaga aaataaatat ttagaagaac tagctgagtt actgtctgcc aacattagtg     360
acattgacag cttgagtgta aaaccagaca aatgcaagat tttgaagaaa acagtcgatc     420
agatacagct aatgaagaga atggaacaag agaaatcaac aactgatgac gatgtacaga     480
aatcagacat ctcatcaagt agtcaaggag tgatagaaaa ggaatccttg ggaccccttc     540
ttttggaggc tttggatgga tttttctttg ttgtgaactg tgaagggaga attgtatttg     600
tgtcagagaa tgtaaccagc tacttaggtt acaatcagga ggaattaatg aataccagcg     660
tctacagcat actgcacgtg ggggatcatg cagaatttgt gaagaatctg ctaccaaaat     720
cactagtaaa tggagttcct tggcctcaag aggcaacacg acgaaatagc catacccttta    780 actgcaggat gctaattcac cctccagatg agccagggac cgagaaccaa gaagcttgcc    840
agcgttatga agtaatgcag tgtttcactg tgtcacagcc aaaatcaatt caagaggatg    900
gagaagattt ccagtcatgt ctgatttgta ttgcacggcg attacctcgg cctccagcta    960
ttacgggtgt agaatccttt atgaccaagc aagatactac aggtaaaatc atctctattg   1020
atactagttc cctgagagct gctggcagaa ctggttggga agatttagtg aggaagtgca   1080
tttatgcttt tttccaacct cagggcagag aaccatctta tgccagacag ctgttccaag   1140
aagtgatgac tcgtggcact gcctccagcc cctcctatag attcatattg aatgatggga   1200
```

-continued

```
caatgcttag cgcccacacc aagtgtaaac tttgctaccc tcaaagtcca gacatgcaac    1260
ctttcatcat gggaattcat atcatcgaca gggagcacag tgggctttct cctcaagatg    1320
acactaattc tggaatgtca attccccgag taaatccctc ggtcaatcct agtatctctc    1380
cagctcatgg tgtggctcgt tcatccacat tgccaccatc caacagcaac atggtatcca    1440
ccagaataaa ccgccagcag agctcagacc ttcatagcag cagtcatagt aattctagca    1500
acagccaagg aagtttcgga tgctcacccg aagtcagat tgtagccaat gttgccttaa    1560
accaaggaca ggccagttca cagagcagta atccctcttt aaacctcaat aattctccta    1620
tggaaggtac aggaatatcc ctagcacagt tcatgtctcc aaggagacag gttacttctg    1680
gattggcaac aaggcccagg atgccaaaca attcctttcc tcctaatatt tcgacattaa    1740
gctctcccgt tggcatgaca agtagtgcct gtaataataa taaccgatct tattcaaaca    1800
tcccagtaac atctttacag ggtatgaatg aaggacccaa taactccgtt ggcttctctg    1860
ccagttctcc agtcctcagg cagatgagct cacagaattc acctagcaga ttaaatatac    1920
aaccagcaaa agctgagtcc aaagataaca agagagattgc ctcaatttta aatgaaatga    1980
ttcaatctga caacagctct agtgatggca aacctctgga ttcagggctt ctgcataaca    2040
atgacagact ttcagatgga gacagtaaat actctcaaac cagtcacaaa ctagtgcagc    2100
ttttgacaac aactgccgaa cagcagttac ggcatgctga tatagacaca agctgcaaag    2160
atgtcctgtc ttgcacaggc acttccaact ctgcctctgc taactcttca ggaggttctt    2220
gtccctcttc tcatagctca ttgacagaac ggcataaaat tctacaccgg ctcttacagg    2280
agggtagccc ctcagatatc accactttgt ctgtcgagcc tgataaaaag gacagtgcat    2340
ctacttctgt gtcagtgact ggacaggtac aaggaaactc cagtataaaa ctagaactgg    2400
atgcttcaaa gaaaaaagaa tcaaaagacc atcagctcct acgctatctt ttagataaag    2460
atgagaaaga tttaagatca actccaaacc tgagcctgga tgatgtaaag gtgaaagtgg    2520
aaaagaaaga acagatggat ccatgtaata caaacccaac cccaatgacc aaacccactc    2580
ctgaggaaat aaaactggag gcccagagcc agtttacagc tgaccttgac cagtttgatc    2640
agttactgcc cacgctggag aaggcagcac agttgccagg cttatgtgag acagacagga    2700
tggatggtgc ggtcaccagt gtaaccatca aatcggagat cctgccagct tcacttcagt    2760
ccgccactgc cagacccact tccaggctaa atagattacc tgagctggaa ttggaagcaa    2820
ttgataacca atttggacaa ccaggaacag gcgatcagat tccatggaca aataatacag    2880
tgacagctat aaatcagagt aaatcagaag accagtgtat tagctcacaa ttagatgagc    2940
ttctctgtcc acccacaaca gtagaaggga gaaatgatga aaggctctt cttgaacagc    3000 tggtatcctt ccttagtggc aaagatgaaa ctgagctagc tgaactagac agagctctgg    3060
gaattgacaa acttgttcag gggggtggat tagatgtatt atcagagaga tttccaccac    3120
aacaagcaac gccacctttg atcatggaag aaagacccaa cctttattcc cagccttact    3180
cttctccttc tcctactgcc aatctcccta gccctttcca aggcatggtc aggcaaaaac    3240
cttcactggg gacgatgcct gttcaagtaa cacctccccg aggtgctttt tcacctggca    3300
tgggcatgca gcccaggcaa actctaaaca gacctccggc tgcacctaac cagcttcgac    3360
ttcaactaca gcagcgatta cagggacaac agcagttgat acaccaaaat cggcaagcta    3420
tcttaaacca gtttgcagca actgctcctg ttggcatcaa tatgagatca ggcatgcaac    3480
agcaaattac acctcagcca cccctgaatg ctcaaatgtt ggcacaacgt cagcgggaac    3540
tgtacagtca acagcaccga cagaggcagc taatacagca gcaaagagcc atgcttatga    3600
```

```
ggcagcaaag ctttgggaac aacctccctc cctcatctgg actaccagtt caaatgggga      3660
acccccgtct tcctcagggt gctccacagc aattcccctα tccaccaaac tatggtacaa      3720
atccaggaac cccacctgct tctaccagcc cgttttcaca actagcagca aatcctgaag      3780
catccttggc caaccgcaac agcatggtga gcagaggcat gacaggaaac ataggaggac      3840
agtttggcac tggaatcaat cctcagatgc agcagaatgt cttccagtat ccaggagcag      3900
gaatggttcc ccaaggtgag gccaactttg ctccatctct aagccctggg agctccatgg      3960
tgccgatgcc aatccctcct cctcagagtt ctctgctcca gcaaactcca cctgcctccg      4020
ggtatcagtc accagacatg aaggcctggc agcaaggagc gataggaaac aacaatgtgt      4080
tcagtcaagc tgtccagaac cagcccacgc ctgcacagcc aggagtatac aacaacatga      4140
gcatcaccgt ttccatggca ggtggaaata cgaatgttca aacatgaac ccaatgatgg      4200 cccagatgca gatgagctct ttgcagatgc aggaatgaa cactgtgtgc cctgagcaga      4260
taaatgatcc cgcactgaga cacacaggcc tctactgcaa ccagctctca tccactgacc      4320
ttctcaaaac agaagcagat ggaacccagg tgcaacaggt tcaggtgttt gctgacgtcc      4380
agtgtacagt gaatctggta ggcggggacc cttacctgaa ccagcctggt ccactgggaa      4440
ctcaaaagcc cacgtcagga ccacagaccc cccaggccca gcagaagagc ctccttcagc      4500
agctactgac tgaataacca cttttaaagg aatgtgaaat ttaaataata gacatacaga      4560
gatatacaaa tatattatat attttttctga gattttttgat atctcaatct gcagccattc      4620
ttcaggtcgt agcatttgga gcaaaaaaaa aaaaaaaaa                             4660

<210> SEQ ID NO 27
<211> LENGTH: 6773
<212> TYPE: DNA
<213> ORGANISM: Homo sapiens

<400> SEQUENCE: 27
gcggctggtt gcgggccggc ggcgggctgg cggagatgga ggatcttgtt caagatgggg       60
tggcttcacc agctaccccct gggaccggga atctaagaa ttggagaaag aaattgaaga      120
actcagatca aaacctgtta ctgaaggaac tggtgatatt attaaggcat taactgaacg      180
tctggatgct cttcttctgg aaaaagcaga gactgagcaa cagtgtcttt ctctgaaaaa      240
ggaaaatata aaaatgaagc aagaggttga ggattctgta acaaagatgg gagatgcaca      300
taaggagttg gaacaatcac atataaacta tgtgaaagaa attgaaaatt tgaaaaatga      360
gttgatggca gtacgttcca atacagtga agacaaagct aacttacaaa agcagctgga      420
agaagcaatg aatacgcaat tagaacttt c agaacaactt aaatttcaga caactctga       480 agataatgtt aaaaaactac aagaagagat tgagaaaatt aggccaggct tgaggagca       540 aattttatat ctgcaaaagc aattagacgc taccactgat gaaaagaagg aaacagttac      600
tcaactccaa aatatcattg aggctaattc tcagcattac caaaaaaata ttaatagttt      660
gcaggaagag cttttacagt tgaaagctat acaccaagaa gaggtgaaag agttgatgtg      720
ccagattgaa gcatcagcta aggaacatga agcagagata ataagttga cgagctaaa       780 agagaactta gtaaaacaat gtgaggcaag tgaaaagaac atccagaaga aatatgaatg      840
tgagttagaa aatttaagga agccaacctc aaatgcaaac caagacaatc agatatgttc      900
tattctcttg caagaaaata catttgtaga caagtagta aatgaaaaag tcaaacactt      960
agaagatacc ttaaagaac ttgaatctca acacagtatc ttaaagatg aggtaactta      1020
```

-continued

```
tatgaataat cttaagttaa aacttgaaat ggatgctcaa catataaagg atgagttttt      1080
tcatgaacgg gaagacttag agtttaaaat taatgaatta ttactagcta agaagaaca       1140 gggctgtgta attgaaaaat taaaatctga gctagcaggt ttaaataaac agttttgcta      1200
tactgtagaa cagcataaca gagaagtaca gagtcttaag gaacaacatc aaaaagaaat      1260
atcagaacta aatgagacat ttttgtcaga ttcagaaaaa gaaaaattaa cattaatgtt     1320
tgaaatacag ggtcttaagg aacagtgtga aaacctacag caagaaaagc aagaagcaat     1380
tttaaattat gagagtttac gagagattat ggaaattta caaacagaac tgggggaatc      1440
tgctggaaaa ataagtcaag agttcgaatc aatgaagcaa cagcaagcat ctgatgttca     1500
tgaactgcag cagaagctca gaactgcttt tactgaaaaa gatgccttc tcgaaactgt      1560 gaatcgcctc caggagaaa atgaaaagtt actatctcaa caagaattgg taccagaact      1620
tgaaaatacc ataagaacc ttcaagaaaa gaatggagta tacttactta gtctcagtca      1680
aagagatacc atgttaaaag aattagaagg aaagataaat tctcttactg aggaaaaaga    1740
tgattttata aataaactga aaaattccca tgaagaaatg gataatttcc ataagaaatg     1800
tgaaagggaa gaaagattga ttcttgaact tgggaagaaa gtagagcaaa caatccagta    1860
caacagtgaa ctagaacaaa aggtaaatga attaacagga ggactagagg agactttaaa    1920
agaaaaggat caaaatgacc aaaaactaga aaaacttatg gttcaaatga agttctctc      1980 tgaagacaaa gaagtattgt cagctgaagt gaagtctctt tatgaggaaa acaataaact     2040
cagttcagaa aaaaacagt tgagtaggga tttggaggtt ttttgtctc aaaaagaaga       2100 tgttatcctt aaagaacata ttactcaatt agaaaagaaa cttcagttaa tggttgaaga    2160
gcaagataat ttaaataaac tgcttgaaaa tgagcaagtt cagaagttat ttgttaaaac     2220
tcagttgtat ggttttctta agaaatgggg atcagaagtt tcagaagaca gtgaagagaa    2280
agatgttgtt aatgtcctac aggcagtcgg tgaatccttg gcaaaaataa atgaggaaaa    2340
atgcaacctg gcttttcagc gtgatgaaaa agtattagag ttagaaaaag agattaagtg    2400
ccttcaagaa gagagtgtag ttcagtgtga agaacttaag tctttattga gagactatga    2460
gcaagagaaa gttctcttaa ggaaagagtt agaagaaata cagtcagaaa agaggccct     2520 gcagtctgat cttctagaaa tgaagaatgc taatgaaaaa acaaggcttg aaaatcagaa    2580
tcttttaatt caagttgaag aagtatctca acatgtagc aaaagtgaaa tccataatga     2640
aaaagaaaaa tgttttataa aggaacatga aaacctaaag ccactactag aacaaaaaga    2700
attacgagat aggagagcag agttgatact attaaaggat tccttagcaa aatcacccc      2760 tgtaaaaaat gatcctctgt cttcagtaaa agagttggaa gaaaaatag aaaatctgga     2820 aaagaatgc aaagaaaagg aggagaaaat aaataagata aaattagttg ccgtaaaggc     2880
aaagaaagaa ctagattcca gcagaaaaga gacccagact gtgaaggaag aacttgaatc    2940
tcttcgatca gaaaaggacc agttatctgc ttccatgaga gatctcattc aaggagcaga    3000
aagctataag aatctttat tagaatatga aaagcagtca gagcaactgg atgtggaaaa    3060
agaacgtgct aataattttg agcatcgtat tgaagacctt acaagacaat taagaaattc    3120
gactttgcag tgtgaaacaa taattctga taatgaagat ctcctggctc gtattgagac     3180
attacagtct aatgccaaat tattagaagt acagattta gaagtccaga gagccaaagc     3240
aatggtagac aaagaattag aagctgaaaa acttcagaaa gaacagaaga taaggaaca    3300 tgccactact gtaaatgaac ttgaagaact tcaggtacaa cttcaaaagg aaagaaaca    3360 gcttcagaaa accatgcaag aattagagct ggttaaaaag gatgcccaac aaaccacatt    3420
```

```
gatgaatatg gaaatagctg attatgaacg tttgatgaaa gaactaaatc aaaagttaac    3480
taataaaaac aacaagatag aagatttgga gcaagaaata aaaattcaaa aacagaaaca    3540 agaaaccta  caagaagaaa taacttcatt acagtcttca gtacaacaat atgaagaaaa    3600
aaacaccaaa atcaagcaat tgcttgtgaa aaccaaaaag gaactggcag attcaaagca    3660
agcagaaact gatcacttaa tacttcaagc atctttaaaa ggtgagctgg aggcaagcca    3720
gcagcaagta gaagtctata aaatacagct ggctgaaata acatcagaga agcacaaaat    3780
ccacgagcac ctgaaaacct ctgcggaaca gcaccagcgt acgctaagtg cataccagca    3840
gagagtgaca gcactacagg aagagtgccg tgctgccaag gcagaacaag ctactgtaac    3900
ctctgaattc gagagctaca aagtccgagt tcataatgtt ctaaaacaac agaaaaataa    3960
atctatgtct caggctgaaa ctgagggcgc taaacaagaa agggaacatc tggaaatgct    4020
gattgaccag ctaaaaatca aattacaaga tagccaaaat aacttacaga ttaatgtatc    4080
tgaacttcaa acattgcagt ctgaacatga tacactgcta gaaaggcaca acaagatgct    4140
gcaggaaact gtgtccaaag aggcggaact ccgggaaaaa ttgtgttcaa tacagtcaga    4200
gaacatgatg atgaaatctg aacatacaca gactgtgagt cagctaacat cccagaacga    4260
ggtccttcga aatagcttcc gagatcaagt gcgacatttg caggaagaac acagaaagac    4320
agtggagaca ttacagcagc agctctccaa gatggaagca cagctcttcc agcttaagaa    4380
tgaaccgacc acaagaagcc cagtttcctc tcaacaatct ttgaagaacc ttcgagaaag    4440
gagaaacaca gacctcccgc ttctagacat gcacactgta acccgggaag agggagaagg    4500
catggagaca actgatacgg agtctgtgtc ttccgccagc acatacacac agtctttaga    4560
gcagctgctt aactctcccg aaactaaact tgagcctcca ttatggcatg ctgaatttac    4620
caaagaagaa ttggttcaga agctcagttc caccacaaaa agtgcagatc acttaaacgg    4680
cctgcttcgg gaaacagaag caaccaatgc aattcttatg gagcaaatta gcttctcaa     4740 aagtgaaata gaagattgg aaaggaatca agagcgagag aagtctgcag ctaacctgga    4800
atacttgaag aacgtcttgc tgcagttcat tttcttgaaa ccaggtagtg aaagagagag    4860
acttcttcct gttataaata cgatgttgca gctcagccct gaagaaaagg gaaaacttgc    4920
tgcggttgct caaggtgagg aagaaaatgc ttcccgttct tctggatggg catcctatct    4980
tcatagttgg tctggacttc gataggttga tggaaggaat attttatta accaaataga    5040 atctatttac aaaaatggtt cacgtatatt accacaattc ttttgtcaaa aagtgtgtat    5100
atatgtttgc atctacatat atttgtacat ctatatgaca gatgtatttt aaagtttca    5160 tcttgaagta aaagtacaac agcttgaagt gttgatagca ggccacagcc ctctaactca    5220
tgtgatttcc catgcatgct gccagaataa aaccaccagg aatgaattca ctccccactt    5280
ctctggaacc tcaggacccg cccatttctc ggcagtactg tgaattttga agttaaacta    5340
aattttggta ccataccaac tggaatttag gctttaaaaa taatgtttca aggccaggtg    5400
tggtgattca tgcctgaaat cccactactt tgggaggctg aggctggaga attgcttgag    5460
gctagtgagc tgtgactccc actgcactcc agctcgggga acagagcgag accttgtctc    5520
taaaaataat agtaataaaa taaaaataac gttttatgac tatttattgc aaggtcagag    5580
ttacagattg ttataaattg ttgagaaatt tttgtgatta gaatatgaag gaaaagcttt    5640
tgttggtaaa agtgacatgt taaggggcta tgaagtaaat atgctgcagt taattgtgct    5700
aagttaaaat acagtttagt tatttgcttt aaaataaact cttctttttt tctttaaagt    5760
```

-continued

| | |
|---|---|
| atactatctc aaaactcatt atgttgtcag agccctagag ctggctagtg taacactgac | 5820 |
| tatgagtagg tgggcccacc acttgagttg aggtgatttc atggtgtctt tccaggctct | 5880 |
| tgatagggtg tcactgcatg caagccatga atctgttttg agaatcctct ccattttccc | 5940 |
| aaataaaaac ctatcacaac agtgactata tcactcagca ttggatctaa atataaagt | 6000 |
| ggtgctttca gtgttttggg cagatagtgt tccataagct ttccatcaga agggatttta | 6060 |
| gacaccttag aggtccgtgc tacatcgtca cagttcctcc gaataacctt aggtggtagt | 6120 |
| gttacttgcc tttgacacct ctgcatatgt tttaatgact agatccaaac tgtgttgttc | 6180 |
| ttaaatcaaa aattggataa tttgtaatat ttatgtgtta atcacacagt atgctctctg | 6240 |
| aagttctctt aagccttcag tttatactct taatttaatt ttctttctga gctggagaac | 6300 |
| tggctttgca ctttggttac acagaacatt ggtttccaat tcagtttaac tgaaatttgc | 6360 |
| tgctgatatg ttgagtttgt tcttaaaaaa atagctcata tatctcatct ttcctcctgt | 6420 |
| cttagaagaa cagacctaac tagtgaatgt attaatgaaa atgcatctat ttcagagctg | 6480 |
| acatgaagag tttagttttt ttactttata aactgtgaat atgagtatgc cagctgcata | 6540 |
| cgatgtaact aatcatattt aaatatattt cacttctct ttgactttag accttttgaa | 6600 |
| gtctgtataa acttgttttg aaatatagtc tctgcttacg aatgtcataa caaataatt | 6660 |
| ttttgcatga taaaaaatta ctttgattac aaaaggcgta ttctttcatg gtttctgcaa | 6720 |
| tgagaggaag tgtaatgatt attttaatat ttctattaaa tatgtttaac tgt | 6773 |

<210> SEQ ID NO 28
<211> LENGTH: 2619
<212> TYPE: DNA
<213> ORGANISM: Homo sapiens

<400> SEQUENCE: 28

| | |
|---|---|
| atggccacag cttgtaaaag atcaggagaa cctcagtctg acgacattga agctagccga | 60 |
| atgaagcgag cagctgcaaa gcatctaata gaacgctact accaccagtt aactgagggc | 120 |
| tgtggaaatg aagcctgcac gaatgagttt tgtgcttcct gtccaacttt tcttcgtatg | 180 |
| gataataatg cagcagctat taaagccctc gagctttata agattaatgc aaaactctgt | 240 |
| gatcctcatc cctccaagaa aggagcaagc tcagcttacc ttgagaactc gaaaggtgcc | 300 |
| cccaacaact cctgctctga gataaaaatg aacaagaaag gcgctagaat tgattttaaa | 360 |
| gatgtgactt acttaacaga agagaaggta tatgaaattc ttgaattatg tagagaaaga | 420 |
| gaggattatt ccccttttaat ccgtgttatt ggaagagttt tttctagtgc tgaggcattg | 480 |
| gtacagagct tccggaaagt taaacaacac accaaggaag aactgaaatc tcttcaagca | 540 |
| aaagatgaag acaaagatga agatgaaaag gaaaaagctg catgttctgc tgctgctatg | 600 |
| gaagaagact cagaagcatc ttcctcaagg ataggtgata gctcacaggg agacaacaat | 660 |
| ttgcaaaaat taggccctga tgatgtgtct gtggatattg atgccattag aagggtctac | 720 |
| accagattgc tctctaatga aaaaattgaa actgcctttc tcaatgcact tgtatatttg | 780 |
| tcacctaacg tggaatgtga cttgacgtat cacaatgtat actctcgaga tcctaattat | 840 |
| ctgaatttgt tcattatcgg aatggagaat agaaatctcc acagtcctga atatctggaa | 900 |
| atggctttgc cattattttg caaagcgatg agcaagctac cccttgcagc ccaaggaaaa | 960 |
| ctgatcagac tgtggtctaa atacaatgca gaccagattc ggagaatgat ggagacatttt | 1020 |
| cagcaactta ttacttataa agtcataagc aatgaattta cagtcgaaa tctagtgaat | 1080 |
| gatgatgatg ccattgttgc tgcttcgaag tgcttgaaaa tggtttacta tgcaaatgta | 1140 |

```
gtgggagggg aagtggacac aaatcacaat gaagaagatg atgaagagcc catccctgag    1200
tccagcgagc tgacacttca ggaacttttg ggagaagaaa gaagaaacaa gaaaggtcct    1260
cgagtggacc ccctggaaac tgaacttggt gttaaaaccc tggattgtcg aaaaccactt    1320 atccctttg aagagtttat taatgaacca ctgaatgagg ttctagaaat ggataaagat    1380 tatactttt tcaaagtaga aacagagaac aaattctctt ttatgacatg tcccttata    1440 ttgaatgctg tcacaaagaa tttgggatta tattatgaca atagaattcg catgtacagt    1500
gaacgaagaa tcactgttct ctacagctta gttcaaggac agcagttgaa tccatatttg    1560
agactcaaag ttagacgtga ccatatcata gatgatgcac ttgtccggct agagatgatc    1620
gctatggaaa atcctgcaga cttgaagaag cagttgtatg tggaatttga aggagaacaa    1680
ggagttgatg agggaggtgt ttccaaagaa ttttttcagc tggttgtgga ggaaatcttc    1740
aatccagata ttggtatgtt cacatacgat gaatctacaa aattgttttg gtttaatcca    1800 tcttctttg aaactgaggg tcagtttact ctgattggca tagtactggg tctggctatt    1860
tacaataact gtatactgga tgtacatttt cccatggttg tctacaggaa gctaatgggg    1920 aaaaaggaa cttttcgtga cttgggagac tctcacccag ttctatatca gagtttaaaa    1980
gatttattgg agtatgaagg gaatgtggaa gatgacatga tgatcacttt ccagatatca    2040
cagacagatc ttttggtaa cccaatgatg tatgatctaa aggaaatgg tgataaaatt    2100 ccaattacaa atgaaaacag gaaggaattt gtcaatcttt attctgacta cattctcaat    2160
aaatcagtag aaaaacagtt caaggctttt cggagaggtt ttcatatggt gaccaatgaa    2220
tctcccttaa agtacttatt cagaccagaa gaaattgaat tgcttatatg tggaagccgg    2280
aatctagatt tccaagcact agaagaaact acagaatatg acggtggcta taccagggac    2340
tctgttctga ttagggagtt ctgggaaatc gttcattcat ttacagatga acagaaaaga    2400
ctcttcttgc agtttacaac gggcacagac agagcacctg tgggaggact aggaaaatta    2460
aagatgatta tagccaaaaa tggcccagac acagaaaggt tacctacatc tcatacttgc    2520
tttaatgtgc ttttacttcc ggaatactca agcaaagaaa aacttaaaga gagattgttg    2580
aaggccatca cgtatgccaa aggatttggc atgctgtaa                           2619

<210> SEQ ID NO 29
<211> LENGTH: 4263
<212> TYPE: DNA
<213> ORGANISM: Homo sapiens

<400> SEQUENCE: 29
ggccgttccc ctctcctcag cagtagctct atggtttcag ggcggcaacg tgcagcgtcc      60
ttaccttgag cctgtgcagt tgccctcacc ccggaatcca tagtcactgt gacgaggcgg     120
gaggacttgg gcgacaggta gcctcccagt cccacacgct gcgggtccgc gcctggccaa     180
gccacctcga cctgtgaagt tggggcggt acccagcaac tccccctgtg cagccgccgt     240
ttccaagggg tcaggaaccg ctgtgtttgt ttcgtccgcg tagccaggc gggtcgcgga     300 gtactgtgcc tgacccgacg gtggcaagtc tgacgcgtca gccagagacc ggtgcccggt     360
gtaggagtcg cagcctgggc tgtgagcggc tgctgggtag acagacttgc tttctcttac     420
agcatgtcat ttccaaaatg catcgtggtg cttctgcctt aagtcctata ggaagacact     480
gccgccacta gaccggtgct tatggtcgcc actgttattc tgactcaggt cccgtgtcat     540
tgagcatatg tatgaaaatg ccttaggagg gaaccatgga gaagtatgtg agactgcaga     600
```

```
agattggaga aggttcattt ggaaaagctg ttcttgttaa atcgacagag gatggcagac    660
attatgtcat caaggaaatt aacatctcaa gaatgtctga taaagaaagg caagaatcaa    720
ggagagaagt tgctgtattg gcaaacatga agcatccaaa tattgtccaa tataaagaat    780
catttgaaga aaatggctct ctctacatag taatggatta ctgtgaagga ggtgatttgt    840
ttaaacgaat aaatgctcag aaaggcgctc tgtttcaaga agaccagatt ttggactggt    900
ttgtgcagat atgtttggct ctgaagcatg tacatgatag aaaaattctt caccgagaca    960
taaagtcaca gaacatattt ctaaccaaag atgggacagt gcagcttgga gattttggaa   1020
ttgctcgagt tcttaatagt actgtagagc tggctcgaac ttgcataggc actccatact   1080
acttgtcacc tgaaatctgt gaaaacaagc cttataacaa taaagtgac atttgggctt    1140
tgggctgtgt cctttatgag ttgtgtacac ttaaacatgc atttgaagct ggaaacatga   1200
aaaacctggt actgaagata atctccggat cctttcctcc agtgtctcca cattactcct   1260
atgatctccg cagcttgctg tctcagttat ttaaaagaaa tcctagggat agaccatcag   1320
tcaactccat attggagaaa ggttttatag ctaaacgaat cgaaaagttt ctctcccctc   1380
agcttattgc agaagaattt tgtctaaaaa cactttcaaa gtttggacca cagcctctcc   1440
caggtaaaag accagcatca ggacaaggtg tcagttcttt tgtccctgct cagaaaatca   1500
caaagcctgc tgctaaatac ggagtgcctt aacatataa gaagtatgga gataaaaagt    1560
tacttgagaa aaaaccaccc ccaaaacata acaggcccaa tcaaattccc gtgaagaaaa   1620
tgaattctgg agaagaaagg aagaaaatgt ctgaggaagc agcaaaaaaa agaaggttgg   1680
aatttattga gaaagaaaag aagcaaaagg atcagattag gttcctgaag ctgagcaga    1740
tgaagcggca agagaagcag cggttggaga ggataaaatag ggccagggaa caaggatgga   1800
ggaatgtttt aagggctggt ggaagcggtg aagtaaaggc ttccttttt ggcattggag    1860
gggctgtctc tccatcaccg tgttctcctc gaggccagta tgaacattac catgccattt   1920
ttgaccaaat gcagcggcta agagcagaag ataatgaagc aagatggaag ggggaatct    1980
atggtcgatg gctcccagaa aggcaaaaag gacacttagc tgtagagaga gccaaccaag   2040
tggaagaatt cctacagcgt aaacgagaag ctatgcagaa taaagcccga gccgaaggac   2100
acgtggttta tttggcaaga ctgaggcaaa taagactaca aaattttaat gagcgccaac   2160
agattaaagc caaacttcgt ggtgagaata agaagctga tggtaccaaa ggacaagaag    2220
caactgaaga gactgacatg aggctcaaaa agatggagtc acttaaggcg caaacaaatg   2280
cacgtgctgc tgtactaaaa aacagctgg agcgaaaaag aaaggaagct tatgaaagag   2340
aaaagaaagt atgggaagaa catttggtgg cgagggtaaa aagctcagat gttcctctgc   2400
ctttggaact tcttgaaaca ggtggttctc catcaaagca gcaggtgaag cctgtcattt   2460
ctgtgacttc agctttgaaa gaagtgggcc tggatggaag tttaactgat acccaggaag   2520
aagaaatgga aagagtaac agtgctattt caagtaagcg agaaatcctg cgtaggctaa    2580
atgaaaatct taaagctcaa gaggatgaaa aggaaaagca gcatcactca ggttcttgtg   2640
agaccgttgg tcacaaagat gagagagagt atgagacaga aaatgccatt tcctctgatc   2700
gcaagaagtg ggagatggga ggtcagcttg tgattcctct cgatgcagtg acactggata   2760
catccttctc tgcaaccgaa aaacatactg tgggagaggt tattaaatta gattctaatg   2820
gctctccaag aaaagtctgg ggaaaaaacc ctacagattc tgtgctgaag atacttggag   2880
aagctgaatt acagctatag acagaactac tagaaaacac atcttttaaa agtgaggttt   2940
atgctgaaga ggagaactac aaaccttac ttactgaaga agagaatctg cagtgcattt    3000
```

| | |
|---|---|
| caaaagaaat aaatccatca gctactgttg attctactga aacgaaaagt ccaaagttta | 3060 |
| ctgaggtgtc tccacaaatg tcagaaggaa atgtggaaga acctgatgat ttggaaacag | 3120 |
| aagttctaca agagccaagt agcacacaca cagatgggag tttgccacct gttcttaatg | 3180 |
| atgtgtggac tagagagaag gaagcagcta aggaaactga gttggaagat aaggttgctg | 3240 |
| tgcagcagag tgaagtttgt gaagatagaa ttccagggaa cgtggaccaa tcctgtaagg | 3300 |
| atcagagaga tcctgcagta gacgattctc cgcagtctgg ctgtgatgta gagaagtcag | 3360 |
| tacagccaga atcgattttc cagaaagtgg ttcattctaa ggacttgaac ttagttcagg | 3420 |
| cagttcattg ctcaccagaa gaaccaattc caattcgatc tcactctgat tctccaccaa | 3480 |
| aaactaagag caagaattcc ttactgattg gactttcaac tggtctgttt gatgcaaaca | 3540 |
| atccaaagat gctgaggacc tgctcacttc cagatctttc caagctgttc agaaccctaa | 3600 |
| tggacgttcc cactgtgggg gacgttcatc aagacagtct tgaaatcgat gagctggaag | 3660 |
| atgaaccaat taagaaggg ccttctgatt ccgaagacac tgtatttgaa gaaactgaca | 3720 |
| cagatttaca agagcttcag gcctcaatgg agcagctgct tagggagcaa ccaggtgacg | 3780 |
| aatacagtga ggaggaagag tctgttttaa aaagcagcga tgtggagcag acagcaagag | 3840 |
| ggacagatgc cccagacgag gaggacaacc ccagcagcga aagcccctga cgaggaatg | 3900 |
| gcactcagat aatagtgacg ctgagaccac tagtgaatgt gaatatgaca gtgtctttaa | 3960 |
| ccatttagag gaactaagac ttcacttgga gcaagaaatg ggctttgaaa agttcttga | 4020 |
| ggtttatgag aaagtaaagg ctattcatga ggatgaagat gaaaatattg aaatttgttc | 4080 |
| aacaatagtt gagaatattt tgggcaatga gcaccagcat ctctatgcca agattctgca | 4140 |
| tttagtcatg gcagatggag cctatcagga agataatgat gaataatcct caggacattc | 4200 |
| tttaatagtc aactgtaaga acacatttga acttggctca taatacaagc ttcctgggaa | 4260 |
| ata | 4263 |

<210> SEQ ID NO 30
<211> LENGTH: 1756
<212> TYPE: DNA
<213> ORGANISM: Homo sapiens

<400> SEQUENCE: 30

| | |
|---|---|
| tcgggcgcag ccgcgaagat gccgttggaa ctgacgcaga gccgagtgca aagatctgg | 60 |
| gtgcccgtgg accacaggcc ctcgttgccc agatcctgtg ggccaaagct gaccaactcc | 120 |
| cccaccgtca tcgtcatggt gggcctcccc gcccggggca agacctacat ctccaagaag | 180 |
| ctgactcgct acctcaactg gattggcgtc cccacaaaag tgttcaacgt cggggagtat | 240 |
| cgccgggagg ctgtgaagca gtacagctcc tacaacttct ccgccccga caatgaggaa | 300 |
| gccatgaaag tccggaagca atgtgcctta gctgccttga gagatgtcaa aagctacctg | 360 |
| gcgaaagaag ggggacaaat tgcggttttc gatgccacca atactactag agagaggaga | 420 |
| cacatgatcc ttcattttgc caaagaaaat gactttaaag cgttttcat cgagtcggtg | 480 |
| tgcgacgacc ctacagttgt ggcctccaat atcatggaag ttaaaatctc cagcccggat | 540 |
| tacaaagact gcaactcggc agaagccatg gacgacttca tgaagaggat cagttgctat | 600 |
| gaagccagct accagccct cgaccccgac aaaatgcgaca gggacttgtc gctgatcaag | 660 |
| gtgattgacg tgggccggag gttcctggtg aaccgggtgc aggaccacat ccagagccgc | 720 |
| atcgtgtact acctgatgaa catccacgtg cagccgcgta ccatctacct gtgccggcac | 780 |

-continued

```
ggcgagaacg agcacaacct ccagggccgc atcgggggcg actcaggcct gtccagccgg      840
ggcaagaagt tgccagtgc tctgagcaag ttcgtggagg agcagaacct gaaggacctg       900
cgcgtgtgga ccagccagct gaagagcacc atccagacgg ccgaggcgct gcggctgccc      960
tacgagcagt ggaaggcgct caatgagatc gacgcgggcg tctgtgagga gctgacctac     1020
gaggagatca gggacaccta ccctgaggag tatgcgctgc gggagcagga caagtactat    1080
taccgctacc ccaccgggga gtcctaccag gacctggtcc agcgcttgga gccagtgatc    1140
atggagctgg agcggcagga gaatgtgctg gtcatctgcc accaggccgt cctgcgctgc    1200
ctgcttgcct acttcctgga taagagtgca gaggagatgc cctacctgaa atgccctctt    1260
cacaccgtcc tgaaactgac gcctgtcgct tatggctgcc gtgtggaatc catctacctg    1320
aacgtggagt ccgtctgcac acaccgggag aggtcagagg atgcaaagaa gggacctaac    1380
ccgctcatga gacgcaatag tgtcacccccg ctagccagcc ccgaacccac caaaaagcct    1440
cgcatcaaca gctttgagga gcatgtggcc tccacctcgg ccgccctgcc cagctgcctg    1500
cccccggagg tgcccacgca gctgcctgga caaaacatga aaggctcccg gagcagcgct    1560
gactcctcca ggaaacactg aggcagacgt gtcggttcca ttccatttcc atttctgcag    1620
cttagcttgt gtcctgccct ccgcccgagg caaaacgtat cctgaggact tcttccggag    1680
agggtggggt ggagcagcgg gggagccttg gccgaagaga accatgcttg gcaccgtctg    1740 tgtccctcg gccgct                                                     1756

<210> SEQ ID NO 31
<211> LENGTH: 1661
<212> TYPE: DNA
<213> ORGANISM: Homo sapiens

<400> SEQUENCE: 31
tgctgcagcc gctgccgccg attccggatc tcattgccac gcgcccccga cgaccgcccg       60
acgtgcattc ccgattcctt ttggttccaa gtccaatatg caactctaa aggatcagct      120 gatttataat cttctaaagg aagaacagac cccccagaat aagattacag ttgttggggt     180
tggtgctgtt ggcatggcct gtgccatcag tatcttaatg aaggacttgg cagatgaact     240
tgctcttgtt gatgtcatcg aagacaaatt gaagggagag atgatggatc tccaacatgg     300
cagccttttc cttagaacac caaagattgt ctctggcaaa gactataatg taactgcaaa     360
ctccaagctg gtcattatca cggctggggc acgtcagcaa gagggagaaa gccgtcttaa     420
tttggtccag cgtaacgtga acatatttaa attcatcatt cctaatgttg taaaatacag    480
cccgaactgc aagttgctta ttgtttcaaa tccagtggat atcttgacct acgtggcttg     540
gaagataagt ggttttccca aaaccgtgt tattggaagt ggttgcaatc tggattcagc     600
ccgattccgt tacctgatgg gggaaaggct gggagttcac ccattaagct gtcatgggtg     660
ggtccttggg gaacatggag attccagtgt gcctgtatgg agtggaatga atgttgctgg     720
tgtctctctg aagactctgc acccagattt agggactgat aaagataagg aacagtggaa     780
agaggttcac aagcaggtgg ttgagagtgc ttatgaggtg atcaaactca aaggctacac     840
atcctgggct attggactct ctgtagcaga tttggcagag agtataatga agaatcttag     900
gcgggtgcac ccagtttcca ccatgattaa gggtctttac ggaataaagg atgatgtctt     960
ccttagtgtt ccttgcattt tgggacagaa tggaatctca gaccttgtga aggtgactct    1020
gacttctgag gaagaggccc gtttgaagaa gagtgcagat acactttggg ggatccaaaa    1080
ggagctgcaa ttttaaagtc ttctgatgtc atatcatttc actgtctagg ctacaacagg    1140
```

-continued

```
attctaggtg gaggttgtgc atgttgtcct ttttatctga tctgtgatta aagcagtaat    1200
attttaagat ggactgggaa aaacatcaac tcctgaagtt agaaataaga atggtttgta    1260
aaatccacag ctatatcctg atgctggatg gtattaatct tgtgtagtct tcaactggtt    1320
agtgtgaaat agttctgcca cctctgacgc accactgcca atgctgtacg tactgcattt    1380
gccccttgag ccaggtggat gtttaccgtg tgttatataa cttcctggct ccttcactga    1440
acatgcctag tccaacattt tttcccagtg agtcacatcc tgggatccag tgtataaatc    1500
caatatcatg tcttgtgcat aattcttcca aaggatctta ttttgtgaac tatatcagta    1560
gtgtacatta ccataatg taaaaagatc tacatacaaa caatgcaacc aactatccaa    1620
gtgttatacc aactaaaacc cccaataaac cttgaacagt g                         1661

<210> SEQ ID NO 32
<211> LENGTH: 4169
<212> TYPE: DNA
<213> ORGANISM: Homo sapiens

<400> SEQUENCE: 32
ggcggcttcc agtgggcgc gcaaggccgt ggtcctgctt tgtgcctctg acctgctgct       60
gctgctgcta ctgctaccac cgcctgggtc ctgcgcggcc gaaggctcgc ccgggacgcc     120
cgacgagtct acccccacctc cccggaagaa gaagaaggat attcgcgatt acaatgatgc     180
agacatggcg cgtcttctgg agcaatggga aaagatgat gacattgaag aaggagatct     240
tccagagcac aagagacctt cagcacctgt cgacttctca aagatagacc caagcaagcc     300
tgaaagcata ttgaaaatga cgaaaaaagg gaagactctc atgatgtttg tcactgtatc     360
aggaagccct actgagaagg agacagagga aattacgagc ctctggcagg gcagccttt     420
caatgccaac tatgacgtcc agaggttcat tgtgggatca gaccgtgcta tcttcatgct     480
tcgcgatggg agctacgcct gggagatcaa ggacttttg gtcggtcaag acaggtgtgc     540
tgatgtaact ctggagggcc agtgtaccc cggcaaagga ggaggaagca agagaaaaa     600
taaaacaaag caagacaagg gcaaaaaaaa gaaggaagga gatctgaaat ctcggtcttc     660
caaggaagaa aatcgagctg ggaataaaag agaagacctg tgatgggcga gcagtgacgc     720
gctgtggggg gacaggtgga cgtggagagc tctttgccca gctcctgggg tgggagtggt     780
ctcaggcaac tgcacaccgg atgacattct agtgtcttct agaaagggtc tgccacatga     840
ccagtttgtg gtcaaagaat tactgcttaa taggcttcaa gtaagaagac atgttttc      900
taattaatac tggacactga caattcatg tttactataa aatctcctta catgaaatg     960
tgactgtgtt gctttttccc atttacactt ggtgagtcat caactctact gagattccac    1020
tcccctccaa gcacctgctg tgattgggtg gcctgctctg atcagatagc aaattctgat    1080
cagagaagac tttaaaactc ttgacttaat tgagtaaact cttcatgcca tatacatcat    1140
tttcattatg ttaaggtaa aatatgcttt gtgaactcag atgtctgtag ccaggaagcc    1200
agggtgtgta aatccaaaat ctatgcagga aatgcgaga atagaaaata tgtcacttga    1260
aatcctaagt agttttgaat ttctttgact tgaatcttac tcatcagtaa gagaactctt    1320
ggtgtctgtc aggtttatg tggtctgtaa agttagggg tctgttttgt ttccttattt    1380
aggaaagagt actgctggtg tcgagggtt atatgttcca tttaatgtga cagttttaaa    1440
ggatttaagt agggaatcag agtcctttgc agagtgtgac agacgactca ataacctcat    1500
ttgtttctaa acatttttct ttgataaagt gcctaaatct gtgctttcgt atagagtaac    1560
```

```
atgatgtgct actgttgatg tctgattttg ccgttcatgt tagagcctac tgtgaataag    1620
agttagaaca tttatataca gatgtcattt ctaagaacta aaattctttg ggaaaaaccc    1680
tcaattgtga ttttaataaa ttaaaagtag cacattacat ggttagaaaa tgtcagtgtt    1740
aaagaatggt acaaagtgaa aagtgtatcc ctctcttgcc gccggtggta gcttgtccca    1800
gtggaagctg ctgttaacaa tttgtgcccc cacatccccc tccctgccca tccaccaaaa    1860
aaaagtacat ttacttatgt aaatgtactt atggtgatgt atgtttgttt tggcctcaca    1920
gcatctgttt cccettaatt tggtagctgc tcacatttcc ctcgaaagaa ccacaccctc    1980
tgcattctca gttctttgct ttggatggga catttgccct gcagtccccc caccctccag    2040
gccatgccct ctccagggtg aggcctgtgt gatctaccgt actagggtac taggccctga    2100
aagaggcttt tcttgttcct cctgcatctt gaacctggag cgggagctgt tgtaggcccc    2160
gcccttggag aagagaactg tctgacagtg gggagagagc gccacaccct ggtggcataa    2220
acgagtccct gaatcatgcc gtggctgaac caagccctgt ctgtgggctt tttctgttgt    2280
actcagggca gtttgatggg gttactgtcc tgcatagcca taatggccca gtataaagca    2340
gctgttttga tgagataatt gctttaatta agcaaaaggt agcaaagctt tcactccgcc    2400
ctgtaccttc tgtttccact taggagcctt cccatgtcag aatgtgcaga tctgtctcat    2460
tgtttcctgt gcagtgtgcc cccacttcac ccagtagttt ctgtgtgtct gttatgtact    2520
aggtactaca aggtgccagg acggtgtaga tacagcctct gctatcgtaa aactcaatga    2580
ttcggtgggg aagacaaat gtcagtaatg tacaaagtaa aatggcagct gttagaagta    2640
tgaaaggggc agggtagggg gaggtagaat cttccctgac caggttaaga aaaccagagg    2700
ccttctctga gggcaagagg aggagaggag aaatagagta aggcaggcag aggaaacagt    2760
ctgagctaag accctgtggc tagaagtggc agagggagag gcagcaggaa ggccagcggg    2820
gaggctgggc cccagtgcag gcccaggttg gaggagcgta gcacatggag tttggtagga    2880
gtttgggacg ccctggtgga tcttaattgt gatggggtgg gtgtgaaagg cagtccaggt    2940
tgcactggtt gcacaggaga agtgatcaga agaggacccc agcaggtgtg agccgtgagc    3000
tgggaggtgc ttcagtagtg caggccatag ctgaaggtgt cctacatcag cagggtgatg    3060
gtgaggtttg aaccactgtt tcactgcata gtccctgctg atggacactt gagtgttcag    3120
attttttgct ggtatattca gtgctgcagt ggacattttc atacaaaata tttcggtaca    3180
cttttgttta tatctgaaag gtaaattcct agcagtagaa ttattagagc aaacggaatt    3240
taacattttg gtgtgtattg ccaaattgcc ctcccaagtg gtttagtcag cttacccttg    3300
ccaacaatag atctatcctt gccagccttg ggcatcacat ttaccagttt aatagattgt    3360
aaaaccatat cttaattggc taccctgaag ccaccatact ggagaggctg cgtacagtgt    3420
ttcacgtaga gagagggata cccaggaggc ccacctgctc caaccccagc tgcatgagtc    3480
ttcccagccc aggcacagac atgtggataa gatttaaaca tttccagccc cagccttcaa    3540
gcaatcctag ttgacactga ggggagccaa cataagctga gctgagaaac agtctgccca    3600
gtctgcagat tcatgagcaa agaaatgtt gggctgggta cagtggctca cgcctgtaat    3660
cccagtactt tgggaggccg aggtgggtgg atcagttgag gtcaggagtt tgagaccagc    3720
ctggccaaca tggtgaagcc ctgtctctac taaaaattag ccgagtgtgg tggtgcgggc    3780
ctgtaatccc agctactcag gtggctgagg caggagaatg gcttgaaccc gggaggcgga    3840
ggttgcagtg agccaagatc aggccactgc actccagcct ggatgacggg atgagactct    3900
gtctcaaaaa aacgaaacaa aaattttttta agagaaatgt catttgtttt tgttttgag    3960
```

```
acagggtctc actctgttgc cctcactaga gtgcagtagg gatcacggct cactgaagtc    4020
tctacctacc ggctcaattg atcttcccac cacagcctcc caaatagctg ggagaaatgt    4080
cctgttttta atgaatttgt cttccttttt gtcttgtttg ttttaatatc tagtgatcta    4140
ataaatttgg atgatatctt ttgactatc                                     4169
```

<210> SEQ ID NO 33
<211> LENGTH: 859
<212> TYPE: DNA
<213> ORGANISM: Homo sapiens

<400> SEQUENCE: 33

```
catgccatgc agcttaccaa ccatcgagtc tgggactatg ctggagataa ctatgttcat      60
cgactggttg caagtaaaac agatggaaaa atagtacagt atgaatgtga gggggatact     120
tgccaggaag agaaaataga tgccttacag ttagagtatt catatttact aacaagccag     180
ctggaatctc agcgaatcta ctgggaaaac aagatagttc ggatagagaa ggacacagca     240
gaggaaatta acaacatgaa gaccaagttt aagaaacaa ttgagaagtg tgataatcta      300
gagcacaaac taaatgatct cctaaaagaa aagcagtctg tggaaagaaa gtgcactcag     360
ctaaacacaa agtggccaa actcaccaac gagctcaaag aggagcagga atgaacaag       420 tgtttgcgag ccaaccaagt cctcctgcag aacaagctaa agaggagga gagggtgctg      480 aaggagacct gtgaccaaaa agatctgcag atcaccgaga tccaggagca gctgcgtgac     540
gtcatgttct acctggagac acagcagaag atcaaccatc tgcctgccga gacccggcag     600
gaaatccagg aggacagat caacatcgcc atggcctcgg cctcgagccc tgcctcttcg      660
gggggcagtg ggaagttgcc ctccaggaag ggccgcagca gagggggcaa gtgaccttca     720
gagcaacaga catccctgag actgttctcc ctgacactgt gagagtgtgc tgggaccttc     780
agctaaatgt gagggtgggc cctaataagt acaagtgagg acgaaggccg gccttcgtgg     840
ccttagagat ggatgaggc                                                859
```

<210> SEQ ID NO 34
<211> LENGTH: 1070
<212> TYPE: DNA
<213> ORGANISM: Homo sapiens

<400> SEQUENCE: 34

```
gcgattgctg gggctgcagc gctgcctccg agaccgagag tgggtggagc gggtcttcct      60
ggaagggtgc gataaggccg gcgaggtgc ctgggatgct tctcccttc cgcgaggaag       120 agatctaatt gggtagggcg ggtgtagact agcctgccga gccgcccgct ggcacctgca     180
gcctcctggg cgcccgcggg cccggcgaga agttgttaa agggagcgag gtggttgttc      240
ctggggtccg aggcgcgcct ctcacgccct gcccaacaga agccgcagtc ccgtgggtc      300 tggagacgca gtttccttgt taatgacaat aaatccctgc tcccctgcc tcagacatct      360 acgcagcgaa atcgagcctg gccttgaggg tccacaccgc gaggaagatg cgtgcgccca     420
ttccagagcc taagcctgga gacctgattg agattttcg cccctttctac agacactggg    480 ccatctatgt tggcgatgga tatgtggttc atctggcccc tccaagtgag gtcgcaggag     540
ctggtgcagc cagtgtcatg tccgccctga ctgacaaggc catcgtgaag aaggaattgc     600
tgtatgatgt ggccgggagt gacaagtacc aggtcaacaa caaacatgat gacaagtact     660
cgccgctgcc ctgcacgaaa atcatccagc gggcggagga gctggtgggg caggaggtgc     720
```

-continued

```
tctacaagct gaccagtgag aactgcgagc actttgtgaa tgagctgcgc tatggagtcg    780
cccgcagtga ccaggtcaga gatgtcatca tcgctgcaag cgttgcagga atgggcttgg    840
cagccatgag ccttattgga gtcatgttct caagaaacaa gcgacaaaag caataactga    900
aaaagactgt ctgtcagcga tgactttata catcaagggg gtcttgtttt gctagagagt    960
ttggggtttg gtttgtggat ttcattgtga tttataataa ggcttatttt cacagaataa   1020
aataaagcaa aacgagggag gattttattg ggggagtgca gcccaaaaaa              1070
```

<210> SEQ ID NO 35
<211> LENGTH: 460
<212> TYPE: DNA
<213> ORGANISM: Homo sapiens

<400> SEQUENCE: 35

```
cttttcctcc catgtcgcca ccgaggtgcc acgcgtgaga cttctccgcc gcctccgccg     60
cagacgccgc cgcgatgcgc tacgtcgcct cctacctgct ggctgcccta gggggcaact    120
cctcccccag cgccaaggac atcaagaaga tcttggacag cgtgggtatc gaggcggacg    180
acgaccggct caacaaggtt atcagtgagc tgaatggaaa aaacattgaa gacgtcattg    240
cccagggtat tggcaagctt gccagtgtac ctgctggtgg ggctgtagcc gtctctgctg    300
ccccaggctc tgcagcccct gctgctggtt ctgcccctgc tgcagcagag gagaagaaag    360
atgagaagaa ggaggagtct gaagagtcag atgatgacat gggatttggc cttttttgatt    420 aaattcctgc tcccctgcaa ataaagcctt tttacacatc                          460
```

RENAL CANCER ASSOCIATED ANTIGENS AND USES THEREFOR

FIELD OF THE INVENTION

The invention relates to nucleic acids and encoded polypeptides which are cancer associated antigens expressed in patients afflicted with renal cancer. The invention also relates to agents which bind the nucleic acids or polypeptides. The nucleic acid molecules, polypeptides coded for by such molecules and peptides derived therefrom, as well as related antibodies and cytolytic T lymphocytes, are useful, inter alia, in diagnostic and therapeutic contexts.

BACKGROUND OF THE INVENTION

The mechanism by which T cells recognize foreign materials has been implicated in cancer. A number of cytolytic T lymphocyte (CTL) clones directed against autologous melanoma antigens, testicular antigens, and melanocyte differentiation antigens have been described. In many instances, the antigens recognized by these clones have been characterized.

The use of autologous CTLs for identifying tumor antigens requires that the target cells which express the antigens can be cultured in vitro and that stable lines of autologous CTL clones which recognize the antigen-expressing cells can be isolated and propagated. While this approach has worked well for melanoma antigens, other tumor types, such as epithelial cancers including breast and colon cancer, have proved refractory to the approach.

More recently another approach to the problem has been described by Sahin et al. (*Proc. Natl. Acad. Sci. USA* 92:11810–11813, 1995). According to this approach, autologous antisera are used to identify immunogenic protein antigens expressed in cancer cells by screening expression libraries constructed from tumor cell cDNA. Antigen-encoding clones so identified have been found to have elicited an high-titer humoral immune response in the patients from which the antisera were obtained. Such a high-titer IgG response implies helper T cell recognition of the detected antigen. These tumor antigens can then be screened for the presence of MHC/HLA class I and class II motifs and reactivity with CTLs.

Presently there is a need for additional cancer antigens for development of therapeutics and diagnosis applicable to a greater number of cancer patients having various cancers.

SUMMARY OF THE INVENTION

Autologous antibody screening has now been applied to renal cancer using antisera from cancer patients. Numerous cancer associated antigens have been identified. The invention provides, inter alia, isolated nucleic acid molecules, expression vectors containing those molecules and host cells transfected with those molecules. The invention also provides isolated proteins and peptides, antibodies to those proteins and peptides and CTLs which recognize the proteins and peptides. Fragments including functional fragments and variants of the foregoing also are provided. Kits containing the foregoing molecules additionally are provided. The foregoing can be used in the diagnosis, monitoring, research, or treatment of conditions characterized by the expression of one or more cancer associated antigens.

Prior to the present invention, only a handful of cancer associated genes had been identified in the past 20 years. The invention involves the surprising discovery of several genes, some previously known and some previously unknown, which are expressed in individuals who have cancer. These individuals all have serum antibodies against the proteins (or fragments thereof) encoded by these genes. Thus, abnormally expressed genes are recognized by the host's immune system and therefore can form a basis for diagnosis, monitoring and therapy.

The invention involves the use of a single material, a plurality of different materials and even large panels and combinations of materials. For example, a single gene, a single protein encoded by a gene, a single functional fragment thereof, a single antibody thereto, etc. can be used in methods and products of the invention. Likewise, pairs, groups and even panels of these materials and optionally other cancer associated antigen genes and/or gene products can be used for diagnosis, monitoring and therapy. The pairs, groups or panels can involve 2, 3, 4, 5 or more genes, gene products, fragments thereof or agents that recognize such materials. A plurality of such materials are not only useful in monitoring, typing, characterizing and diagnosing cells abnormally expressing such genes, but a plurality of such materials can be used therapeutically. An example of the use of a plurality of such materials for the prevention, delay of onset, amelioration, etc. of cancer cells, which express or will express such genes prophylactically or acutely. Any and all combinations of the genes, gene products, and materials which recognize the genes and gene products can be tested and identified for use according to the invention. It would be far too lengthy to recite all such combinations; those skilled in the art, particularly in view of the teaching contained herein, will readily be able to determine which combinations are most appropriate for which circumstances.

As will be clear from the following discussion, the invention has in vivo and in vitro uses, including for therapeutic, diagnostic, monitoring and research purposes. One aspect of the invention is the ability to fingerprint a cell expressing a number of the genes identified according to the invention by, for example, quantifying the expression of such gene products. Such fingerprints will be characteristic, for example, of the stage of the cancer, the type of the cancer, or even the effect in animal models of a therapy on a cancer. Cells also can be screened to determine whether such cells abnormally express the genes identified according to the invention.

The invention, in one aspect, is a method of diagnosing a disorder characterized by expression of a cancer associated antigen precursor coded for by a nucleic acid molecule. The method involves the steps of contacting a biological sample isolated from a subject with an agent that specifically binds to the nucleic acid molecule, an expression product thereof, or a fragment of an expression product thereof complexed with an MHC, preferably an HLA, molecule, wherein the nucleic acid molecule is a NA Group 1 nucleic acid molecule, and determining the interaction between the agent and the nucleic acid molecule, the expression product or fragment of the expression product as a determination of the disorder.

In one embodiment the agent is selected from the group consisting of (a) a nucleic acid molecule comprising NA Group 1 nucleic acid molecules or a fragment thereof, (b) a nucleic acid molecule comprising NA Group 3 nucleic acid molecules or a fragment thereof, (c) a nucleic acid molecule comprising NA Group 5 nucleic acid molecules or a fragment thereof, (d) an antibody that binds to an expression product, or a fragment thereof, of NA group 1 nucleic acids, (e) an antibody that binds to an expression product, or a fragment thereof, of NA group 3 nucleic acids, (f) an antibody that binds to an expression product, or a fragment thereof, of NA group 5 nucleic acids, (g) and agent that binds to a complex of an MHC, preferably HLA, molecule and a fragment of an expression product of a NA Group 1 nucleic acid, (h) an agent that binds to a complex of an MHC, preferably HLA, molecule and a fragment of an expression product of a NA group 3 nucleic acid, and (i) an agent that binds to a complex of an MHC, preferably HLA, molecule and a fragment of an expression product of a NA Group 5 nucleic acid.

The disorder may be characterized by expression of a plurality of cancer associated antigen precursors. Thus the methods of diagnosis may include use of a plurality of agents, each of which is specific for a different human cancer associated antigen precursor (including at least one of the cancer associated antigen precursors disclosed herein), and wherein said plurality of agents is at least 2, at least 3, at least 4, at least 5, at least 6, at least 7, at least 8, at least 9 or at least 10 such agents.

In each of the above embodiments the agent may be specific for a human cancer associated antigen precursor, including the renal cancer associated antigen precursors disclosed herein.

In another aspect the invention is a method for determining regression, progression or onset of a condition characterized by expression of abnormal levels of a protein encoded by a nucleic acid molecule that is a NA Group 1 molecule. The method involves the steps of monitoring a sample, from a subject who has or is suspected of having the condition, for a parameter selected from the group consisting of (i) the protein, (ii) a peptide derived from the protein, (iii) an antibody which selectively binds the protein or peptide, and (iv) cytolytic T cells specific for a complex of the peptide derived from the protein and an MHC molecule, as a determination of regression, progression or onset of said condition. In one embodiment the sample is a body fluid, a body effusion or a tissue.

In another embodiment the step of monitoring comprises contacting the sample with a detectable agent selected from the group consisting of (a) an antibody which selectively binds the protein of (i), or the peptide of (ii), (b) a protein or peptide which binds the antibody of (iii), and (c) a cell which presents the complex of the peptide and MHC molecule of (iv). In a preferred embodiment the antibody, the protein, the peptide or the cell is labeled with a radioactive label or an enzyme. The sample in a preferred embodiment is assayed for the peptide.

According to another embodiment the nucleic acid molecule is one of the following: a NA Group 3 molecule or a NA Group 5 molecule. In yet another embodiment the protein is a plurality of proteins, the parameter is a plurality of parameters, each of the plurality of parameters being specific for a different of the plurality of proteins.

The invention in another aspect is a pharmaceutical preparation for a human subject. The pharmaceutical preparation includes an agent which when administered to the subject enriches selectively the presence of complexes of an HLA molecule and a human cancer associated antigen, and a pharmaceutically acceptable carrier, wherein the human cancer associated antigen is a fragment of a human cancer associated antigen precursor encoded by a nucleic acid molecule which comprises a NA Group 1 molecule. In one embodiment the nucleic acid molecule is a NA Group 3 nucleic acid molecule.

The agent in one embodiment comprises a plurality of agents, each of which enriches selectively in the subject complexes of an HLA molecule and a different human cancer associated antigen. Preferably the plurality is at least two, at least three, at least four or at least 5 different such agents.

In another embodiment the agent is selected from the group consisting of (1) an isolated polypeptide comprising the human cancer associated antigen, or a functional variant thereof, (2) an isolated nucleic acid operably linked to a promoter for expressing the isolated polypeptide, or functional variant thereof, (3) a host cell expressing the isolated polypeptide, or functional variant thereof, and (4) isolated complexes of the polypeptide, or functional variants thereof, and an HLA molecule.

The agent may be a cell expressing an isolated polypeptide. In one embodiment the agent is a cell expressing an isolated polypeptide comprising the human cancer associated antigen or a functional variant thereof. In another embodiment the agent is a cell expressing an isolated polypeptide comprising the human cancer associated antigen or a functional variant thereof, and wherein the cell expresses an HLA molecule that binds the polypeptide. The cell can express one or both of the polypeptide and HLA molecule recombinantly. In preferred embodiments the cell is nonproliferative. In yet another embodiment the agent is at least two, at least three, at least four or at least five different polypeptides, each representing a different human cancer associated antigen or functional variant thereof.

The agent in one embodiment is a PP Group 2 polypeptide. In other embodiments the agent is a PP Group 3 polypeptide or a PP Group 4 polypeptide.

In an embodiment each of the pharmaceutical preparations described herein also includes an adjuvant.

According to another aspect the invention, a composition is provided which includes an isolated agent that binds selectively a PP Group 1 polypeptide. In separate embodiments the agent binds selectively to a polypeptide selected from the following: a PP Group 2 polypeptide, a PP Group 3 polypeptide, a PP Group 4 polypeptide, and a PP Group 5 polypeptide. In other embodiments, the agent is a plurality of different agents that bind selectively at least two, at least three, at least four, or at least five different such polypeptides. In each of the above described embodiments the agent may be an antibody.

In another aspect the invention is a composition of matter composed of a conjugate of the agent of the above-described compositions of the invention and a therapeutic or diagnostic agent. Preferably the conjugate is of the agent and a therapeutic or diagnostic that is an antineoplastic.

The invention in another aspect is a pharmaceutical composition which includes an isolated nucleic acid molecule selected from the group consisting of: (1) NA Group 1 molecules, and (2) NA Group 2 molecules, and a pharmaceutically acceptable carrier. In one embodiment the isolated nucleic acid molecule comprises a NA Group 3 or NA Group 4 molecule. In another embodiment the isolated nucleic acid molecule comprises at least two isolated nucleic acid molecules coding for two different polypeptides, each polypeptide comprising a different cancer associated antigen.

Preferably the pharmaceutical composition also includes an expression vector with a promoter operably linked to the isolated nucleic acid molecule. In another embodiment the pharmaceutical composition also includes a host cell recombinantly expressing the isolated nucleic acid molecule.

According to another aspect of the invention a pharmaceutical composition is provided. The pharmaceutical composition includes an isolated polypeptide comprising a PP Group 1 or a PP Group 2 polypeptide, and a pharmaceutically acceptable carrier. In one embodiment the isolated polypeptide comprises a PP Group 3 or a PP Group 4 polypeptide.

In another embodiment the isolated polypeptide comprises at least two different polypeptides, each comprising a different cancer associated antigen at least one of which is encoded by a NA group 1 molecule as disclosed herein. In separate embodiments the isolated polypeptides are selected from the following: PP Group 3 polypeptides or HLA binding fragments thereof and PP Group 5 polypeptides or HLA binding fragments thereof.

In an embodiment each of the pharmaceutical compositions described herein also includes an adjuvant.

Another aspect the invention is an isolated nucleic acid molecule comprising a NA Group 3 molecule. Another aspect the invention is an isolated nucleic acid molecule comprising a NA Group 4 molecule.

The invention in another aspect is an isolated nucleic acid molecule selected from the group consisting of (a) a fragment of a nucleic acid selected from the group of nucleic acid molecules consisting of SEQ ID Nos numbered below and comprising all nucleic acid sequences among SEQ ID NOs 1–11 and 22–35, of sufficient length to represent a sequence unique within the human genome, and identifying a nucleic acid encoding a human cancer associated antigen precursor, (b) complements of (a), provided that the fragment includes a sequence of contiguous nucleotides which is not identical to any sequence selected from the sequence group consisting of (1) sequences having the GenBank accession numbers of Table 1, (2) complements of (1), and (3) fragments of (1) and (2).

In one embodiment the sequence of contiguous nucleotides is selected from the group consisting of: (1) at least two contiguous nucleotides nonidentical to the sequences in Table 1, (2) at least three contiguous nucleotides nonidentical to the sequences in Table 1, (3) at least four contiguous nucleotides nonidentical to the sequences in Table 1, (4) at least five contiguous nucleotides nonidentical to the sequences in Table 1, (5) at least six contiguous nucleotides nonidentical to the sequences in Table 1, or (6) at least seven contiguous nucleotides nonidentical to the sequences in Table 1.

In another embodiment the fragment has a size selected from the group consisting of at least: 8 nucleotides, 10 nucleotides, 12 nucleotides, 14 nucleotides, 16 nucleotides, 18 nucleotides, 20, nucleotides, 22 nucleotides, 24 nucleotides, 26 nucleotides, 28 nucleotides, 30 nucleotides, 50 nucleotides, 75 nucleotides, 100 nucleotides, 200 nucleotides, 1000 nucleotides a and every integer length therebetween.

In yet another embodiment the molecule encodes a polypeptide which, or a fragment of which, binds a human HLA receptor or a human antibody.

Another aspect t of the invention is an expression vector comprising an isolated nucleic ac id molecule of the invention described above operably linked to a promoter.

According to one aspect the invention is an expression vector comprising a nucleic acid operably linked to a promoter, wherein the nucleic acid is a NA Group 1 or Group 2 molecule. In another aspect the invention is an expression vector comprising a NA Group 1 or Group 2 molecule and a nucleic acid encoding an MHC, preferably HLA, molecule.

In yet another aspect the invention is a host cell transformed or transfected with an expression vector of the invention described above.

In another aspect the invention is a host cell transformed or transfected with an expression vector comprising an isolated nucleic acid molecule of the invention described above operably linked to a promoter, or an expression vector comprising a nucleic acid operably linked to a promoter, wherein the nucleic acid is a NA Group 1 or 2 molecule and further comprising a nucleic acid encoding HLA.

According to another aspect of the invention an isolated polypeptide encoded by the isolated nucleic acid molecules the invention, described above, is provided. These include PP Group 1–5 polypeptides. The invention also includes a fragment of the polypeptide which is immunogenic. In one embodiment the fragment, or a portion of the fragment, binds HLA or a human antibody.

The invention includes in another aspect an isolated fragment of a human cancer associated antigen precursor which, or portion of which, binds HLA or a human antibody, wherein the precursor is encoded by a nucleic acid molecule that is a NA Group 1 molecule. In one embodiment the fragment is part of a complex with HLA. In another embodiment the fragment is between 8 and 12 amino acids in length. In another embodiment the invention includes an isolated polypeptide comprising a fragment of the polypeptide of sufficient length to represent a sequence unique within the human genome and identifying a polypeptide that is a human cancer associated antigen precursor.

According to another aspect of the invention a kit for detecting the presence of the expression of a cancer associated antigen precursor is provided. The kit includes a pair of isolated nucleic acid molecules each of which consists essentially of a molecule selected from the group consisting of (a) a 12–32 nucleotide contiguous segment of the nucleotide sequence of any of the NA Group 1 molecules and (b) complements of ("a"), wherein the contiguous segments are nonoverlapping. In one embodiment the pair of isolated nucleic acid molecules is constructed and arranged to selectively amplify an isolated nucleic acid molecule that is a NA Group 3 molecule. Preferably, the pair amplifies a human NA Group 3 molecule.

According to another aspect of the invention a method for treating a subject with a disorder characterized by expression of a human cancer associated antigen precursor is provided. The method includes the step of administering to the subject an amount of an agent, which enriches selectively in the subject the presence of complexes of an HLA molecule and a human cancer associated antigen, effective to ameliorate the disorder, wherein the human cancer associated antigen is a fragment of a human cancer associated antigen precursor encoded by a nucleic acid molecule selected from the group consisting of (a) a nucleic acid molecule comprising NA group 1 nucleic acid molecules, (b) a nucleic acid molecule comprising NA group 3 nucleic acid molecules, (c) a nucleic acid molecule comprising NA group 5 nucleic acid molecules.

In one embodiment the disorder is characterized by expression of a plurality of human cancer associated antigen precursors and wherein the agent is a plurality of agents, each of which enriches selectively in the subject the presence of complexes of an HLA molecule and a different human cancer associated antigen. Preferably the plurality is at least 2, at least 3, at least 4, or at least 5 such agents.

In another embodiment the agent is an isolated polypeptide selected from the group consisting of PP Group 1, PP Group 2, PP Group 3, PP Group 4, and PP group 5 polypeptides.

In yet another embodiment the disorder is cancer.

According to another aspect the invention is a method for treating a subject having a condition characterized by expression of a cancer associated antigen precursor in cells of the subject. The method includes the steps of (i) removing an immunoreactive cell containing sample from the subject, (ii) contacting the immunoreactive cell containing sample to the host cell under conditions favoring production of cytolytic T cells against a human cancer associated antigen which is a fragment of the precursor, (iii) introducing the cytolytic T cells to the subject in an amount effective to lyse cells which express the human cancer associated antigen, wherein the host cell is transformed or transfected with an expression vector comprising an isolated nucleic acid molecule operably linked to a promoter, the isolated nucleic acid molecule being selected from the group of nucleic acid molecules consisting of NA Group 1, NA Group 2, NA Group 3, NA Group 4, NA Group 5.

In one embodiment the host cell recombinantly expresses an HLA molecule which binds the human cancer associated antigen. In another embodiment the host cell endogenously expresses an HLA molecule which binds the human cancer associated antigen.

The invention includes in another aspect a method for treating a subject having a condition characterized by expression of a cancer associated antigen precursor in cells of the subject. The method includes the steps of (i) identifying a nucleic acid molecule expressed by the cells associated with said condition, wherein said nucleic acid molecule is a NA Group 1 molecule (ii) transfecting a host cell with a nucleic acid selected from the group consisting of (a) the nucleic acid molecule identified, (b) a fragment of the nucleic acid identified which includes a segment coding for a cancer associated antigen, (c) deletions, substitutions or additions to (a) or (b), and (d) degenerates of (a), (b), or (c); (iii) culturing said transfected host cells to express the transfected nucleic acid molecule, and; (iv) introducing an amount of said host cells or an extract thereof to the subject effective to increase an immune response against the cells of the subject associated with the condition. Preferably, the antigen is a human antigen and the subject is a human.

In one embodiment the method also includes the step of (a) identifying an MHC molecule which presents a portion of an expression product of the nucleic acid molecule, wherein the host cell expresses the same MHC molecule as identified in (a) and wherein the host cell presents an MHC binding portion of the expression product of the nucleic acid molecule.

In another embodiment the method also includes the step of treating the host cells to render them non-proliferative.

In yet another embodiment the immune response comprises a B-cell response or a T cell response. Preferably the response is a T-cell response which comprises generation of cytolytic T-cells specific for the host cells presenting the portion of the expression product of the nucleic acid molecule or cells of the subject expressing the human cancer associated antigen.

In another embodiment the nucleic acid molecule is a NA Group 3 molecule.

Another aspect of the invention is a method for treating or diagnosing or monitoring a subject having a condition characterized by expression of an abnormal amount of a protein encoded by a nucleic acid molecule that is a NA Group 1 molecule. The method includes the step of administering to the subject an antibody which specifically binds to the protein or a peptide derived therefrom, the antibody being coupled to a therapeutically useful agent, in an amount effective to treat the condition.

In one embodiment the antibody is a monoclonal antibody. Preferably the monoclonal antibody is a chimeric antibody or a humanized antibody.

In another aspect the invention is a method for treating a condition characterized by expression in a subject of abnormal amounts of a protein encoded by a nucleic acid molecule that is a NA Group 1 nucleic acid molecule. The method involves the step of administering to a subject at least one of the pharmaceutical compositions of the invention described above in an amount effective to prevent, delay the onset of, or inhibit the condition in the subject. In one embodiment the condition is cancer. In another embodiment the method includes the step of first identifying that the subject expresses in a tissue abnormal amounts of the protein.

The invention in another aspect is a method for treating a subject having a condition characterized by expression of abnormal amounts of a protein encoded by a nucleic acid molecule that is a NA Group 1 nucleic acid molecule. The method includes the steps of (i) identifying cells from the subject which express abnormal amounts of the protein; (ii) isolating a sample of the cells; (iii) cultivating the cells, and (iv) introducing the cells to the subject in an amount effective to provoke an immune response against the cells.

In one embodiment the method includes the step of rendering the cells non-proliferative, prior to introducing them to the subject.

In another aspect the invention is a method for treating a pathological cell condition characterized by abnormal expression of a protein encoded by a nucleic acid molecule that is a NA Group 1 nucleic acid molecule. The method includes the step of administering to a subject in need thereof an effective amount of an agent which inhibits the expression or activity of the protein.

In one embodiment the agent is an inhibiting antibody which selectively binds to the protein and wherein the antibody is a monoclonal antibody, a chimeric antibody, a humanized antibody or a fragment thereof. In another embodiment the agent is an antisense nucleic acid molecule which selectively binds to the nucleic acid molecule which encodes the protein. In yet another important embodiment the nucleic acid molecule is a NA Group 3 nucleic acid molecule.

The invention includes in another aspect a composition of matter useful in stimulating an immune response to a plurality of proteins encoded by nucleic acid molecules that are NA Group 1 molecules. The composition is a plurality of peptides derived from the amino acid sequences of the proteins, wherein the peptides bind to one or more MHC molecules presented on the surface of the cells which express an abnormal amount of the protein.

In one embodiment at least a portion of the plurality of peptides bind to MHC molecules and elicit a cytolytic response thereto. In another embodiment the composition of matter includes an adjuvant. In another embodiment the adjuvant is a saponin, GM-CSF, or an interleukin. In still another embodiment, the compositions also includes at least one peptide useful in stimulating an immune response to at least one protein which is not encoded by nucleic acid molecules that are NA Group 1 molecules, wherein the at least one peptide binds to one or more MHC molecules.

According to another aspect the invention is an isolated antibody which selectively binds to a complex of: (i) a peptide derived from a protein encoded by a nucleic acid molecule that is a NA Group 1 molecule and (ii) and an MHC molecule to which binds the peptide to form the complex, wherein the isolated antibody does not bind to (i) or ( In one embodiment the antibody is a monoclonal antibody, a chimeric antibody, a humanized antibody or a fragment thereof.

The invention also involves the use of the genes, gene products, fragments thereof, agents which bind thereto, and so on in the preparation of medicaments. A particular medicament is for treating cancer and a more particular medicament is for treating breast cancer, lung cancer, renal cancer, colon cancer, prostate cancer or gastric cancer.

DETAILED DESCRIPTION OF THE INVENTION

In the above summary and in the ensuing description, lists of sequences are provided. The lists are meant to embrace each single sequence separately, two or more sequences together where they form a part of the same gene, any combination of two or more sequences which relate to different genes, including and up to the total number on the list, as if each and every combination were separately and specifically enumerated. Likewise, when mentioning fragment size, it is intended that a range embrace the smallest fragment mentioned to the full-length of the sequence (less one nucleotide or amino acid so that it is a fragment), each and every fragment length intended as if specifically enumerated. Thus, if a fragment could be between 10 and 15 in length, it is explicitly meant to mean 10, 11, 12, 13, 14, or 15 in length.

The summary and the claims mention antigen precursors and antigens. As used in the summary and in the claims, a precursor is substantially the full-length protein encoded by the coding region of the isolated DNA and the antigen is a peptide which complexes with MHC, preferably HLA, and which participates in the immune response as part of that complex. Such antigens are typically 9 amino acids long, although this may vary slightly.

As used herein, a subject is a human, non-human primate, cow, horse, pig, sheep, goat, dog, cat or rodent. In all embodiments human cancer antigens and human subjects are preferred.

The present invention in one aspect involves the cloning of cDNAs encoding human cancer associated antigen precursors using autologous antisera of subjects having renal cancer. The sequences of the clones representing genes identified according to the methods described herein are presented in the attached Sequence Listing. Of the foregoing, it can be seen that some of the clones are considered completely novel as no nucleotide or amino acid homologies to coding regions were found in the databases searched. Other clones are novel but have some homology to sequences deposited in databases (mainly EST sequences). Nevertheless, the entire gene sequence was not previously known. In some cases no function was suspected and in other cases, even if a function was suspected, it was not known that the gene was associated with cancer. In all cases, it was not known or suspected that the gene encoded a cancer antigen which reacted with antibody from autologous sera. Analysis of the clone sequences by comparison to nucleic acid and protein databases determined that still other of the clones surprisingly are closely related to other previously-cloned genes. The sequences of these related genes is also presented in the Sequence Listing. The nature of the foregoing genes as encoding antigens recognized by the immune systems of cancer patients is, of course, unexpected.

The invention thus involves in one aspect cancer associated antigen polypeptides, genes encoding those polypeptides, functional modifications and variants of the foregoing, useful fragments of the foregoing, as well as diagnostics and therapeutics relating thereto.

Homologs and alleles of the cancer associated antigen nucleic acids of the invention can be identified by conventional techniques. Thus, an aspect of the invention is those nucleic acid sequences which code for cancer associated antigen precursors. Because this application contains so many sequences, the following chart is provided to identify the various groups of sequences discussed in the claims and in the summary:

Nucleic Acid Sequences

NA Group 1.
(a) nucleic acid molecules which hybridize under stringent conditions to a molecule consisting of a nucleic acid sequence selected from the group consisting of nucleic acid sequences among SEQ ID NOs: 1–11 and 22–35 and which code for a cancer associated antigen precursor,
(b) deletions, additions and substitutions which code for a respective cancer associated antigen precursor,
(c) nucleic acid molecules that differ from the nucleic acid molecules of (a) or (b) in codon sequence due to the degeneracy of the genetic code, and
(d) complements of (a), (b) or (c).

NA Group 2. Fragments of NA Group 1, which codes for a polypeptide which, or a portion of which, binds an MHC molecule to form a complex recognized by a an autologous antibody or lymphocyte.

NA Group 3. The subset of NA Group 1 where the nucleotide sequence is selected from the group consisting of:
(a) previously unknown human nucleic acids coding for a human cancer associated antigen precursor (i.e. nucleic acid sequences among SEQ ID NOs: 1–11),
(b) deletions, additions and substitutions which code for a respective human cancer associated antigen precursor,
(c) nucleic acid molecules that differ from the nucleic acid molecules of (a) or (b) in codon sequence due to the degeneracy of the genetic code, and
(d) complements of (a), (b) or (c).

NA Group 4. Fragments of NA Group 3, which code for a polypeptide which, or a portion of which, binds to an MHC molecule to form a complex recognized by an autologous antibody or lymphocyte.

NA Group 5. A subset of NA Group 1, comprising human cancer associated antigens that react with allogeneic cancer antisera.

Polypeptide Sequences

PP Group 1. Polypeptides encoded by NA Group 1.
PP Group 2. Polypeptides encoded by NA Group 2
PP Group 3. Polypeptides encoded by NA Group 3.
PP Group 4. Polypeptides encoded by NA Group 4.
PP Group 5. Polypeptides encoded by NA Group 5.

The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York.

More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM NaH$_2$PO$_4$(pH7), 0.5% SDS, 2 mM EDTA). SSC is 0.15M sodium chloride/0.15M sodium citrate, pH7; SDS is sodium dodecyl sulphate; and EDTA is ethylenediaminetetracetic acid. After hybridization, the membrane upon which the DNA is transferred is washed, for example, in 2×SSC at room temperature and then at 0.1–0.5×SSC/0.1×SDS at temperatures up to 68° C.

There are other conditions, reagents, and so forth which can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of cancer associated antigen nucleic acids of the invention (e.g., by using lower stringency conditions). The skilled artisan also is familiar with the methodology for screening cells and libraries for expression of such molecules which then are routinely isolated, followed by isolation of the pertinent nucleic acid molecule and sequencing.

In general homologs and alleles typically will share at least 40% nucleotide identity and/or at least 50% amino acid identity to the sequences of cancer associated antigen nucleic acid and polypeptides, respectively, in some instances will share at least 50% nucleotide identity and/or at least 65% amino acid identity and in still other instances will share at least 60% nucleotide identity and/or at least 75% amino acid identity. The homology can be calculated using various, publicly available software tools developed by NCBI (Bethesda, Md.) that can be obtained through the internet. Exemplary tools include the BLAST system available at from NCBI. Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

In screening for cancer associated antigen genes, a Southern blot may be performed using the foregoing conditions, together with a radioactive probe. After washing the membrane to which the DNA is finally transferred, the membrane can be placed against X-ray film to detect the radioactive signal. In screening for the expression of cancer associated antigen nucleic acids, Northern blot hybridizations using the foregoing conditions (see also the Examples) can be performed on samples taken from breast cancer patients or subjects suspected of having a condition characterized by expression of breast cancer associated antigen genes. Amplification protocols such as polymerase chain reaction using primers which hybridize to the sequences presented also can be used for detection of the cancer associated antigen genes or expression thereof.

The renal cancer associated genes correspond to SEQ ID NOs. 1–11 and 22–35. The preferred breast cancer associated antigens for the methods of diagnosis disclosed herein are those which were found to react with allogeneic cancer antisera (i.e. NA Group 5). Encoded polypeptides (e.g., proteins), peptides and antisera thereto are also preferred for diagnosis.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating breast cancer associated antigen polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides isolated unique fragments of cancer associated antigen nucleic acid sequences or complements thereof. A unique fragment is one that is a 'signature' for the larger nucleic acid. It, for example, is long enough to assure that its precise sequence is not found in molecules within the human genome outside of the cancer associated antigen nucleic acids defined above (and human alleles). Those of ordinary skill in the art may apply no more than routine procedures to determine if a fragment is unique within the human genome. Unique fragments, however, exclude fragments completely composed of the nucleotide sequences of any of GenBank accession numbers listed in Table 1 or other previously published sequences as of the filing date of the priority documents for sequences listed in a respective priority document or the filing date of this application for sequences listed for the first time in this application which overlap the sequences of the invention.

A fragment which is completely composed of the sequence described in the foregoing GenBank deposits is one which does not include any of the nucleotides unique to the sequences of the invention. Thus, a unique fragment must contain a nucleotide sequence other than the exact sequence of those in GenBank or fragments thereof. The difference may be an addition, deletion or substitution with respect to the GenBank sequence or it may be a sequence wholly separate from the GenBank sequence.

Unique fragments can be used as probes in Southern and Northern blot assays to identify such nucleic acids, or can be used in amplification assays such as those employing PCR. As known to those skilled in the art, large probes such as 200, 250, 300 or more nucleotides are preferred for certain uses such as Southern and Northern blots, while smaller fragments will be preferred for uses such as PCR. Unique fragments also can be used to produce fusion proteins for generating antibodies or determining binding of the polypeptide fragments, or for generating immunoassay components. Likewise, unique fragments can be employed to produce nonfused fragments of the cancer associated antigen polypeptides, useful, for example, in the preparation of antibodies, and in immunoassays. Unique fragments further can be used as antisense molecules to inhibit the expression of cancer associated antigen nucleic acids and polypeptides, particularly for therapeutic purposes as described in greater detail below.

As will be recognized by those skilled in the art, the size of the unique fragment will depend upon its conservancy in the genetic code. Thus, some regions of cancer associated antigen sequences and complements thereof will require longer segments to be unique while others will require only short segments, typically between 12 and 32 nucleotides (e.g. 12, 13, 14, 15, 16, 17, 18, 19, 20, 21, 22, 23, 24, 25, 26, 27, 28, 29, 30, 31 and 32 or more bases long, up to the entire length of the disclosed sequence. As mentioned above, this disclosure intends to embrace each and every fragment of each sequence, beginning at the first nucleotide, the second nucleotide and so on, up to 8 nucleotides short of the end, and ending anywhere from nucleotide number 8, 9, 10 and so on for each sequence, up to the very last nucleotide (provided the sequence is unique as described above).

Virtually any segment of the polypeptide coding region of novel cancer associated antigen nucleic acids, or complements thereof, that is 18 or more nucleotides in length will be unique. Those skilled in the art are well versed in methods for selecting such sequences, typically on the basis of the ability of the unique fragment to selectively distinguish the sequence of interest from other sequences in the human genome of the fragment to those on known databases typically is all that is necessary, although in vitro confirmatory hybridization and sequencing analysis may be performed.

Especially preferred include nucleic acids encoding a series of epitopes, known as "polytopes". The epitopes can be arranged in sequential or overlapping fashion (see, e.g., Thomson et al., *Proc. Natl. Acad. Sci. USA* 92:5845–5849, 1995; Gilbert et al., *Nature Biotechnol.* 15:1280–1284, 1997), with or without the natural flanking sequences, and can be separated by unrelated linker sequences if desired. The polytope is processed to generated individual epitopes which are recognized by the immune system for generation of immune responses.

Thus, for example, peptides derived from a polypeptide having an amino acid sequence encoded by one of the nucleic acid disclosed herein, and which are presented by MHC molecules and recognized by CTL or T helper lymphocytes, can be combined with peptides from one or more other cancer associated antigens (e.g. by preparation of hybrid nucleic acids or polypeptides) to form "polytopes". The two or more peptides (or nucleic acids encoding the peptides) can be selected from those described herein, or they can include one or more peptides of previously known cancer associated antigens. Exemplary cancer associated peptide antigens that can be administered to induce or enhance an immune response are derived from tumor associated genes and encoded proteins including MAGE-1, MAGE-2, MAGE-3, MAGE-4, MAGE-5, MAGE-6, MAGE-7, MAGE-8, MAGE-9, MAGE-10, MAGE-11, MAGE-12, MAGE-13, GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-B2, MAGE-B3, MAGE-B4, tyrosinase, brain glycogen phosphorylase, Melan-A, MAGE-C1 MAGE-C2, NY-ESO-1, LAGE-1, SSX-1, SSX-2 (HOM-MEL-40) SSX-4, SSX-5, SCP-1 and CT-7. See, for example, PCT application publication no. WO96/10577. Other examples will be known to one of ordinary skill in the art (for example, see Coulie, *Stem Cells* 13:393–403, 1995), and can be used in the invention in a like manner as those disclosed herein. One of ordinary skill in the art can prepare polypeptides comprising one or more peptides and one or more of the foregoing cancer associated peptides, or nucleic acids encoding such polypeptides, according to standard procedures of molecular biology.

Thus polytopes are groups of two or more potentially immunogenic or immune response stimulating peptides which can be joined together in various arrangements (e.g. concatenated, overlapping). The polytope (or nucleic acid encoding the polytope) can be administered in a standard immunization protocol, e.g. to animals, to test the effectiveness of the polytope in stimulating, enhancing and/or provoking an immune response.

The peptides can be joined together directly or via the use of flanking sequences to form polytopes, and the use of polytopes as vaccines is well known in the art (see, e.g., Thomson et al., *Proc. Acad. Natl. Acad. Sci USA* 92(13):5845–5849, 1995; Gilbert et al., *Nature Biotechnol.* 15(12):1280–1284, 1997; Thomson et al., *J. Immunol.* 157 (2):822–826, 1996; Tam et al., *J. Exp. Med.* 171(1):299–306, 1990). For example, Tam showed that polytopes consisting of both MHC class I and class II binding epitopes successfully generated antibody and protective immunity in a mouse model. Tam also demonstrated that polytopes comprising "strings" of epitopes are processed to yield individual epitopes which are presented by MHC molecules and recognized by CTLs. Thus polytopes containing various numbers and combinations of epitopes can be prepared and tested for recognition by CTLs and for efficacy in increasing an immune response.

It is known that tumors express a set of tumor antigens, of which only certain subsets may be expressed in the tumor of any given patient. Polytopes can be prepared which correspond to the different combination of epitopes representing the subset of tumor rejection antigens expressed in a particular patient. Polytopes also can be prepared to reflect a broader spectrum of tumor rejection antigens known to be expressed by a tumor type. Polytopes can be introduced to a patient in need of such treatment as polypeptide structures, or via the use of nucleic acid delivery systems known in the art (see, e.g., Allsopp et al., *Eur. J. Immunol.* 26(8):1951–1959, 1996). Adenovirus, pox virus, Ty-virus like particles, adeno-associated virus, plasmids, bacteria, etc. can be used in such delivery. One can test the polytope delivery systems in mouse models to determine efficacy of the delivery system. The systems also can be tested in human clinical trials.

In instances in which a human HLA class I molecule presents tumor rejection antigens derived from cancer associated nucleic acids, the expression vector may also include a nucleic acid sequence coding for the HLA molecule that presents any particular tumor rejection antigen derived from these nucleic acids and polypeptides. Alternatively, the nucleic acid sequence coding for such a HLA molecule can be contained within a separate expression vector. In a situation where the vector contains both coding sequences, the single vector can be used to transfect a cell which does not normally express either one. Where the coding sequences for a cancer associated antigen precursor and the HLA molecule which presents it are contained on separate expression vectors, the expression vectors can be cotransfected. The cancer associated antigen precursor coding sequence may be used alone, when, e.g. the host cell already expresses a HLA molecule which presents a cancer associated antigen derived from precursor molecules. Of course, there is no limit on the particular host cell which can be used. As the vectors which contain the two coding sequences may be used in any antigen-presenting cells if desired, and the gene for cancer associated antigen precursor can be used in host cells which do not express a HLA molecule which presents a cancer associated antigen. Further, cell-free transcription systems may be used in lieu of cells.

As mentioned above, the invention embraces antisense oligonucleotides that selectively bind to a nucleic acid molecule encoding a cancer associated antigen polypeptide, to reduce the expression of cancer associated antigens. This is desirable in virtually any medical condition wherein a reduction of expression of cancer associated antigens is desirable, e.g., in the treatment of cancer. This is also useful for in vitro or in vivo testing of the effects of a reduction of expression of one or more cancer associated antigens.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon the sequences of nucleic acids encoding breast cancer associated antigen, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nature Biotechnol.* 14:840–844, 1996). Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439–457, 1994) and at which proteins are not expected to bind. Finally, although the listed sequences are cDNA sequences, one of ordinary skill in the art may easily derive the genomic DNA corresponding to the cDNA of a cancer associated antigen. Thus, the present invention also provides for antisense oligonucleotides which are complementary to the genomic DNA corresponding to nucleic acids encoding cancer associated antigens. Similarly, antisense to allelic or homologous cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acids encoding breast cancer associated antigen polypeptides, together with pharmaceutically acceptable carriers.

Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art, as further described below.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a breast cancer associated antigen polypeptide or fragment or variant thereof. That heterologous DNA (RNA) is placed under operable control of transcriptional elements to permit the expression of the heterologous DNA in the host cell.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr Virus (EBV) origin of replication, facilitating the maintenance of plasmid as a multicopy extrachromosomal element. Another expression vector is the pEF-BOS plasmid containing the promoter of polypeptide Elongation Factor 1 a, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710–4716, 1996). Still another preferred expression vector is an adenovirus, described by Stratford-Perricaudet, which is defective for E1 and E3 proteins (*J. Clin. Invest.* 90:626–630, 1992). The use of the adenovirus as an Adeno.P1A recombinant for the expression of an antigen is disclosed by Wamier et al., in intradermal injection in mice for immunization against P1A (*Int. J. Cancer*, 67:303–310, 1996). Additional vectors for delivery of nucleic acid are provided below.

The invention also embraces so-called expression kits, which allow the artisan to prepare a desired expression vector or vectors. Such expression kits include at least separate portions of a vector and one or more of the previously discussed cancer associated antigen nucleic acid molecules. Other components may be added, as desired, as long as the previously mentioned nucleic acid molecules, which are required, are included. The invention also includes kits for amplification of a cancer associated antigen nucleic acid, including at least one pair of amplification primers which hybridize to a cancer associated antigen nucleic acid. The primers preferably are 12–32 nucleotides in length and are non-overlapping to prevent formation of "primer-dimers". One of the primers will hybridize to one strand of the cancer associated antigen nucleic acid and the second primer will hybridize to the complementary strand of the cancer associated antigen nucleic acid, in an arrangement which permits amplification of the cancer associated antigen nucleic acid. Selection of appropriate primer pairs is standard in the art. For example, the selection can be made with assistance of a computer program designed for such a purpose, optionally followed by testing the primers for amplification specificity and efficiency.

The invention also permits the construction of cancer associated antigen gene "knock-outs" in cells and in animals, providing materials for studying certain aspects of cancer and immune system responses to cancer.

The invention also provides isolated polypeptides (including whole proteins and partial proteins) encoded by the foregoing cancer associated antigen nucleic acids. Such polypeptides are useful, for example, alone or as fusion proteins to generate antibodies, as components of an immunoassay or diagnostic assay or as therapeutics. Cancer associated antigen polypeptides can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Short polypeptides, including antigenic peptides (such as are presented by MHC molecules on the surface of a cell for immune recognition) also can be synthesized chemically using well-established methods of peptide synthesis.

A unique fragment of a cancer associated antigen polypeptide, in general, has the features and characteristics of unique fragments as discussed above in connection with nucleic acids. As will be recognized by those skilled in the art, the size of the unique fragment will depend upon factors such as whether the fragment constitutes a portion of a conserved protein domain. Thus, some regions of cancer associated antigens will require longer segments to be unique while others will require only short segments, typically between 5 and 12 amino acids (e.g. 5, 6, 7, 8, 9, 10, 11 or 12 or more amino acids including each integer up to the full length).

Unique fragments of a polypeptide preferably are those fragments which retain a distinct functional capability of the polypeptide. Functional capabilities which can be retained in a unique fragment of a polypeptide include interaction with antibodies, interaction with other polypeptides or fragments thereof, selective binding of nucleic acids or proteins, and enzymatic activity. One important activity is the ability to act as a signature for identifying the polypeptide. Another is the ability to complex with HLA and to provoke in a human an immune response. Those skilled in the art are well versed in methods for selecting unique amino acid sequences, typically on the basis of the ability of the unique fragment to selectively distinguish the sequence of interest from non-family members. A comparison of the sequence of the fragment to those on known databases typically is all that is necessary.

The invention embraces variants of the cancer associated antigen polypeptides described above. As used herein, a "variant" of a cancer associated antigen polypeptide is a polypeptide which contains one or more modifications to the primary amino acid sequence of a cancer associated antigen polypeptide. Modifications which create a cancer associated antigen variant can be made to a cancer associated antigen polypeptide 1) to reduce or eliminate an activity of a cancer associated antigen polypeptide; 2) to enhance a property of a cancer associated antigen polypeptide, such as protein stability in an expression system or the stability of protein-protein binding; 3) to provide a novel activity or property to a cancer associated antigen polypeptide, such as addition of an antigenic epitope or addition of a detectable moiety; or 4) to provide equivalent or better binding to an HLA molecule. Modifications to a cancer associated antigen polypeptide are typically made to the nucleic acid which encodes the cancer associated antigen polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the cancer associated antigen amino acid sequence. One of skill in the art will be familiar with methods for predicting the effect on protein conformation of a change in protein sequence, and can thus "design" a variant cancer associated antigen polypeptide according to known methods. One example of such a method is described by Dahiyat and Mayo in *Science* 278:82–87, 1997, whereby proteins can be designed de novo. The method can be applied to a known protein to vary a only a portion of the polypeptide sequence. By applying the computational methods of Dahiyat and Mayo, specific variants of a cancer associated antigen polypeptide can be proposed and tested to determine whether the variant retains a desired conformation.

In general, variants include cancer associated antigen polypeptides which are modified specifically to alter a feature of the polypeptide unrelated to its desired physiological activity. For example, cysteine residues can be substituted or deleted to prevent unwanted disulfide linkages. Similarly, certain amino acids can be changed to enhance expression of a breast cancer associated antigen polypeptide by eliminating proteolysis by proteases in an expression system (e.g., dibasic amino acid residues in yeast expression systems in which KEX2 protease activity is present).

Mutations of a nucleic acid which encode a cancer associated antigen polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant cancer associated antigen polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a cancer associated antigen gene or cDNA clone to enhance expression of the polypeptide. The activity of variants of cancer associated antigen polypeptides can be tested by cloning the gene encoding the variant cancer associated antigen polypeptide into a bacterial or mammalian expression vector, introducing the vector into an appropriate host cell, expressing the variant cancer associated antigen polypeptide, and testing for a functional capability of the cancer associated antigen polypeptides as disclosed herein. For example, the variant cancer associated antigen polypeptide can be tested for reaction with autologous or allogeneic sera as disclosed in the Examples. Preparation of other variant polypeptides may favor testing of other activities, as will be known to one of ordinary skill in the art.

The skilled artisan will also realize that conservative amino acid substitutions may be made in cancer associated antigen polypeptides to provide functionally equivalent variants of the foregoing polypeptides, i.e, the variants retain the functional capabilities of the cancer associated antigen polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, New York, 1989, or *Current Protocols in Molecular Biology*, F. M. Ausubel, et al., eds., John Wiley & Sons, Inc., New York. Exemplary functionally equivalent variants of the cancer associated antigen polypeptides include conservative amino acid substitutions of in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

For example, upon determining that a peptide derived from a cancer associated antigen polypeptide is presented by an MHC molecule and recognized by CTLs (e.g., as described in the Examples), one can make conservative amino acid substitutions to the amino acid sequence of the peptide, particularly at residues which are thought not to be direct contact points with the MHC molecule. For example, methods for identifying functional variants of HLA class II binding peptides are provided in a published PCT application of Strominger and Wucherpfennig (PCT/US96/03182). Peptides bearing one or more amino acid substitutions also can be tested for concordance with known HLA/MHC motifs prior to synthesis using, e.g. the computer program described by D'Amaro and Drijfhout (D'Amaro et al., *Human Immunol.* 43:13–18, 1995; Drijfhout et al., *Human Immunol.* 43:1–12, 1995). The substituted peptides can then be tested for binding to the MHC molecule and recognition by CTLs when bound to MHC. These variants can be tested for improved stability and are useful, inter alia, in vaccine compositions.

Conservative amino-acid substitutions in the amino acid sequence of cancer associated antigen polypeptides to produce functionally equivalent variants of cancer associated antigen polypeptides typically are made by alteration of a nucleic acid encoding a cancer associated antigen polypeptide. Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488–492, 1985), or by chemical synthesis of a gene encoding a cancer associated antigen polypeptide. Where amino acid substitutions are made to a small unique fragment of a cancer associated antigen polypeptide, such as an antigenic epitope recognized by autologous or allogeneic sera or cytolytic T lymphocytes, the substitutions can be made by directly synthesizing the peptide. The activity of functionally equivalent fragments of cancer associated antigen polypeptides can be tested by cloning the gene encoding the altered cancer associated antigen polypeptide into a bacterial or mammalian expression vector, introducing the vector into an appropriate host cell, expressing the altered cancer associated antigen polypeptide, and testing for a functional capability of the cancer associated antigen polypeptides as disclosed herein. Peptides which are chemically synthesized can be tested directly for function, e.g., for binding to antisera recognizing associated antigens.

The invention as described herein has a number of uses, some of which are described elsewhere herein. First, the invention permits isolation of the cancer associated antigen protein molecules. A variety of methodologies well-known to the skilled practitioner can be utilized to obtain isolated cancer associated antigen molecules. The polypeptide may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of mRNA in cell-free extracts such as the reticulocyte lysate system also may be used to produce polypeptide. Those skilled in the art also can readily follow known methods for isolating cancer associated antigen polypeptides. These include, but are not limited to, immunochromatography, HPLC, size-exclusion chromatography, ion-exchange chromatography and immune-affinity chromatography.

The isolation and identification of cancer associated antigen genes also makes it possible for the artisan to diagnose a disorder characterized by expression of cancer associated antigens. These methods involve determining expression of one or more cancer associated antigen nucleic acids, and/or encoded cancer associated antigen polypeptides and/or peptides derived therefrom. In the former situation, such determinations can be carried out via any standard nucleic acid determination assay, including the polymerase chain reaction, or assaying with labeled hybridization probes. In the latter situation, such determinations can be carried out by screening patient antisera for recognition of the polypeptide.

The invention also makes it possible isolate proteins which bind to cancer associated antigens as disclosed herein, including antibodies and cellular binding partners of the cancer associated antigens. Additional uses are described further herein.

The invention also provides, in certain embodiments, "dominant negative" polypeptides derived from cancer associated antigen polypeptides. A dominant negative polypeptide is an inactive variant of a protein, which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative catalytically-inactive kinase which interacts normally with target proteins but does not phosphorylate the target proteins can reduce phosphorylation of the target proteins in response to a cellular signal. Similarly, a dominant negative transcription factor which binds to a promoter site in the control region of a gene but does not increase gene transcription can reduce the effect of a normal transcription factor by occupying promoter binding sites without increasing transcription.

The end result of the expression of a dominant negative polypeptide in a cell is a reduction in function of active proteins. One of ordinary skill in the art can assess the potential for a dominant negative variant of a protein, and using standard mutagenesis techniques to create one or more dominant negative variant polypeptides. For example, given the teachings contained herein of renal cancer associated antigens, especially those which are similar to known proteins which have known activities, one of ordinary skill in the art can modify the sequence of the cancer associated antigens by site-specific mutagenesis, scanning mutagenesis, partial gene deletion or truncation, and the like. See, e.g., U.S. Pat. No. 5,580,723 and Sambrook et al., *Molecular Cloning: A Laboratory Manual*, Second Edition, Cold Spring Harbor Laboratory Press, 1989. The skilled artisan then can test the population of mutagenized polypeptides for diminution in a selected and/or for retention of such an activity. Other similar methods for creating and testing dominant negative variants of a protein will be apparent to one of ordinary skill in the art.

The invention also involves agents such as polypeptides which bind to cancer associated antigen polypeptides. Such binding agents can be used, for example, in screening assays to detect the presence or absence of cancer associated antigen polypeptides and complexes of cancer associated antigen polypeptides and their binding partners and in purification protocols to isolated cancer associated antigen polypeptides and complexes of cancer associated antigen polypeptides and their binding partners. Such agents also can be used to inhibit the native activity of the cancer associated antigen polypeptides, for example, by binding to such polypeptides.

The invention, therefore, embraces peptide binding agents which, for example, can be antibodies or fragments of antibodies having the ability to selectively bind to cancer associated antigen polypeptides. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to cancer associated antigen polypeptides, and complexes of both cancer associated antigen polypeptides and their binding partners. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. ml 3, fd, or lambda phage), displaying inserts from 4 to about 80 amino acid residues using conventional procedures. The inserts may represent, for example, a completely degenerate or biased array. One then can select phage-bearing inserts which bind to the cancer associated antigen polypeptide. This process can be repeated through several cycles of reselection of phage that bind to the cancer associated antigen polypeptide. Repeated rounds lead to enrichment of phage bearing particular sequences. DNA sequence analysis can be conducted to identify the sequences of the expressed polypeptides. The minimal linear portion of the sequence that binds to the cancer associated antigen polypeptide can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the cancer associated antigen polypeptides. Thus, the cancer associated antigen polypeptides of the invention, or a fragment thereof, can be used to screen peptide libraries, including phage display libraries, to identify and select peptide binding partners of the cancer associated antigen polypeptides of the invention. Such molecules can be used, as described, for screening assays, for purification protocols, for interfering directly with the functioning of cancer associated antigen and for other purposes that will be apparent to those of ordinary skill in the art.

As detailed herein, the foregoing antibodies and other binding molecules may be used for example to identify tissues expressing protein or to purify protein. Antibodies also may be coupled to specific diagnostic labeling agents for imaging of cells and tissues that express cancer associated antigens or to therapeutically useful agents according to standard coupling procedures. Diagnostic agents include, but are not limited to, barium sulfate, iocetamic acid, iopanoic acid, ipodate calcium, diatrizoate sodium, diatrizoate meglumine, metrizamide, tyropanoate sodium and radiodiagnostics including positron emitters such as fluorine-18 and carbon-11, gamma emitters such as iodine-123, technitium-99m, iodine-131 and indium-111, nuclides for nuclear magnetic resonance such as fluorine and gadolinium. Other diagnostic agents useful in the invention will be apparent to one of ordinary skill in the art. As used herein, "therapeutically useful agents" include any therapeutic molecule which desirably is targeted selectively to a cell expressing one of the cancer antigens disclosed herein, including antineoplastic agents, radioiodinated compounds, toxins, other cytostatic or cytolytic drugs, and so forth. Antineoplastic therapeutics are well known and include: aminoglutethimide, azathioprine, bleomycin sulfate, busulfan, carmustine, chlorambucil, cisplatin, cyclophosphamide, cyclosporine, cytarabidine, dacarbazine, dactinomycin, daunorubicin, doxorubicin, taxol, etoposide, fluorouracil, interferon-α, lomustine, mercaptopurine, methotrexate, mitotane, procarbazine HCl, thioguanine, vinblastine sulfate and vincristine sulfate. Additional antineoplastic agents include those disclosed in Chapter 52, Antineoplastic Agents (Paul Calabresi and Bruce A. Chabner), and the introduction thereto, 1202–1263, of Goodman and Gilman's "The Pharmacological Basis of Therapeutics", Eighth Edition, 1990, McGraw-Hill, Inc. (Health Professions Division). Toxins can be proteins such as, for example, pokeweed anti-viral protein, cholera toxin, pertussis toxin, ricin, gelonin, abrin, diphtheria exotoxin, or Pseudomonas exotoxin. Toxin moieties can also be high energy-emitting radionuclides such as cobalt-60.

In the foregoing methods, antibodies prepared according to the invention also preferably are specific for the renal cancer associated antigen/MHC complexes described herein.

When "disorder" is used herein, it refers to any pathological condition where the cancer associated antigens are expressed. An example of such a disorder is cancer, breast, colon, gastric, renal, prostate and lung cancers as particular examples.

Samples of tissue and/or cells for use in the various methods described herein can be obtained through standard methods such as tissue biopsy, including punch biopsy and cell scraping, and collection of blood or other bodily fluids by aspiration or other methods.

In certain embodiments of the invention, an immunoreactive cell sample is removed from a subject. By "immunoreactive cell" is meant a cell which can mature into an immune cell (such as a B cell, a helper T cell, or a cytolytic T cell) upon appropriate stimulation. Thus immunoreactive cells include CD34$^+$ hematopoietic stem cells, immature T cells and immature B cells. When it is desired to produce cytolytic T cells which recognize a cancer associated antigen, the immunoreactive cell is contacted with a cell which expresses a cancer associated antigen under conditions favoring production, differentiation and/or selection of cytolytic T cells; the differentiation of the T cell precursor into a cytolytic T cell upon exposure to antigen is similar to clonal selection of the immune system.

Some therapeutic approaches based upon the disclosure are premised on a response by a subject's immune system, leading to lysis of antigen presenting cells, such as breast cancer cells which present one or more cancer associated antigens. One such approach is the administration of autologous CTLs specific to a cancer associated antigen/MHC complex to a subject with abnormal cells of the phenotype at issue. It is within the ability of one of ordinary skill in the art to develop such CTLs in vitro. An example of a method for T cell differentiation is presented in International Application number PCT/US96/05607. Generally, a sample of cells taken from a subject, such as blood cells, are contacted with a cell presenting the complex and capable of provoking CTLs to proliferate. The target cell can be a transfectant, such as a COS cell. These transfectants present the desired complex of their surface and, when combined with a CTL of interest, stimulate its proliferation. COS cells are widely available, as are other suitable host cells. Specific production of CTL clones is well known in the art. The clonally expanded autologous CTLs then are administered to the subject.

Another method for selecting antigen-specific CTL clones has recently been described (Altman et al., *Science* 274:94–96, 1996; Dunbar et al., *Curr. Biol.* 8:413–416, 1998), in which fluorogenic tetramers of MHC class I molecule/peptide complexes are used to detect specific CTL clones. Briefly, soluble MHC class I molecules are folded in vitro in the presence of $\beta_2$-microglobulin and a peptide antigen which binds the class I molecule. After purification, the MHC/peptide complex is purified and labeled with biotin. Tetramers are formed by mixing the biotinylated peptide-MHC complex with labeled avidin (e.g. phycoerythrin) at a molar ratio or 4:1. Tetramers are then contacted with a source of CTLs such as peripheral blood or lymph node. The tetramers bind CTLs which recognize the peptide antigen/MHC class I complex. Cells bound by the tetramers can be sorted by fluorescence activated cell sorting to isolate the reactive CTLs. The isolated CTLs then can be expanded in vitro for use as described herein.

To detail a therapeutic methodology, referred to as adoptive transfer (Greenberg, *J. Immunol.* 136(5): 1917, 1986; Riddel et al., *Science* 257: 238, 1992; Lynch et al., *Eur. J. Immunol.* 21: 1403–1410,1991; Kast et al., *Cell* 59: 603–614, 1989), cells presenting the desired complex (e.g., dendritic cells) are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the relevant HLA/cancer associated antigen complex. This can be determined very easily, as the art is very familiar with methods for identifying cells which present a particular HLA molecule, as well as how to identify cells expressing DNA of the pertinent sequences, in this case a cancer associated antigen sequence. Once cells presenting the relevant complex are identified via the foregoing screening methodology, they can be combined with a sample from a patient, where the sample contains CTLs. If the complex presenting cells are lysed by the mixed CTL sample, then it can be assumed that a cancer associated antigen is being presented, and the subject is an appropriate candidate for the therapeutic approaches set forth supra.

Adoptive transfer is not the only form of therapy that is available in accordance with the invention. CTLs can also be provoked in vivo, using a number of approaches. One approach is the use of non-proliferative cells expressing the complex. The cells used in this approach may be those that normally express the complex, such as irradiated tumor cells or cells transfected with one or both of the genes necessary for presentation of the complex (i.e. the antigenic peptide and the presenting HLA molecule). Chen et al. (*Proc. Natl. Acad. Sci. USA* 88: 110–114,1991) exemplifies this approach, showing the use of transfected cells expressing HPVE7 peptides in a therapeutic regime. Various cell types may be used. Similarly, vectors carrying one or both of the genes of interest may be used. Viral or bacterial vectors are especially preferred. For example, nucleic acids which encode a cancer associated antigen polypeptide or peptide may be operably linked to promoter and enhancer sequences which direct expression of the cancer associated antigen polypeptide or peptide in certain tissues or cell types. The nucleic acid may be incorporated into an expression vector. Expression vectors may be unmodified extrachromosomal nucleic acids, plasmids or viral genomes constructed or modified to enable insertion of exogenous nucleic acids, such as those encoding cancer associated antigen, as described elsewhere herein. Nucleic acids encoding a cancer associated antigen also may be inserted into a retroviral genome, thereby facilitating integration of the nucleic acid into the genome of the target tissue or cell type. In these systems, the gene of interest is carried by a microorganism, e.g., a Vaccinia virus, pox virus, herpes simplex virus, retrovirus or adenovirus, and the materials de facto "infect" host cells. The cells which result present the complex of interest, and are recognized by autologous CTLs, which then proliferate.

A similar effect can be achieved by combining the cancer associated antigen or a stimulatory fragment thereof with an adjuvant to facilitate incorporation into antigen presenting cells in vivo. The cancer associated antigen polypeptide is processed to yield the peptide partner of the HLA molecule while a cancer associated antigen peptide may be presented without the need for further processing. Generally, subjects can receive an intradermal injection of an effective amount of the cancer associated antigen. Initial doses can be followed by booster doses, following immunization protocols standard in the art. Preferred cancer associated antigens include those found to react with allogeneic cancer antisera, shown in the examples below.

The invention involves the use of various materials disclosed herein to "immunize" subjects or as "vaccines". As used herein, "immunization" or "vaccination" means increasing or activating an immune response against an antigen. It does not require elimination or eradication of a condition but rather contemplates the clinically favorable enhancement of an immune response toward an antigen. Generally accepted animal models can be used for testing of immunization against cancer using a cancer associated antigen nucleic acid. For example, human cancer cells can be introduced into a mouse to create a tumor, and one or more cancer associated antigen nucleic acids can be delivered by the methods described herein. The effect on the cancer cells (e.g., reduction of tumor size) can be assessed as a measure of the effectiveness of the cancer associated antigen nucleic acid immunization. Of course, testing of the foregoing animal model using more conventional methods for immunization include the administration of one or more cancer associated antigen polypeptides or peptides derived therefrom, optionally combined with one or more adjuvants and/or cytokines to boost the immune response. Methods for immunization, including formulation of a vaccine composition and selection of doses, route of administration and the schedule of administration (e.g. primary and one or more booster doses), are well known in the art. The tests also can be performed in humans, where the end point is to test for the presence of enhanced levels of circulating CTLs against cells bearing the antigen, to test for levels of circulating antibodies against the antigen, to test for the presence of cells expressing the antigen and so forth.

As part of the immunization compositions, one or more cancer associated antigens or stimulatory fragments thereof are administered with one or more adjuvants to induce an immune response or to increase an immune response. An adjuvant is a substance incorporated into or administered with antigen which potentiates the immune response. Adjuvants may enhance the immunological response by providing a reservoir of antigen (extracellularly or within macrophages), activating macrophages and stimulating specific sets of lymphocytes. Adjuvants of many kinds are well known in the art. Specific examples of adjuvants include monophosphoryl lipid A (MPL, SmithKline Beecham), a congener obtained after purification and acid hydrolysis of *Salmonella Minnesota* Re 595 lipopolysaccharide; saponins including QS21 (SmithKline Beecham), a pure QA-21 saponin purified from *Quillja saponaria* extract; DQS21, described in PCT application WO96/33739 (SmithKline Beecham); QS-7, QS-17, QS-18, and QS-L1 (So et al., *Mol. Cells* 7:178–186, 1997); incomplete Freund's adjuvant; complete Freund's adjuvant; montanide; and various water-in-oil emulsions prepared from biodegradable oils such as squalene and/or tocopherol. Preferably, the peptides are administered mixed with a combination of DQS21/MPL. The ratio of DQS21 to MPL typically will be about 1:10 to 10:1, preferably about 1:5 to 5:1 and more preferably about 1:1. Typically for human administration, DQS21 and MPL will be present in a vaccine formulation in the range of about 1 $\mu$g to about 100 $\mu$g. Other adjuvants are known in the art and can be used in the invention (see, e.g. Goding, *Monoclonal Antibodies: Principles and Practice*, 2nd Ed., 1986). Methods for the preparation of mixtures or emulsions of peptide and adjuvant are well known to those of skill in the art of vaccination.

Other agents which stimulate the immune response of the subject can also be administered to the subject. For example, other cytokines are also useful in vaccination protocols as a result of their lymphocyte regulatory properties. Many other cytokines useful for such purposes will be known to one of ordinary skill in the art, including interleukin-12 (IL-12) which has been shown to enhance the protective effects of vaccines (see, e.g., *Science* 268: 1432–1434, 1995), GM-CSF and IL-18. Thus cytokines can be administered in conjunction with antigens and adjuvants to increase the immune response to the antigens.

There are a number of immune response potentiating compounds that can be used in vaccination protocols. These include costimulatory molecules provided in either protein or nucleic acid form. Such costimulatory molecules include the B7-1 and B7-2 (CD80 and CD86 respectively) molecules which are expressed on dendritic cells (DC) and interact with the CD28 molecule expressed on the T cell. This interaction provides costimulation (signal 2) to an antigen/MHC/TCR stimulated (signal 1) T cell, increasing T cell proliferation and effector function. B7 also interacts with CTLA4 (CD152) on T cells and studies involving CTLA4 and B7 ligands indicate that the B7-CTLA4 interaction can enhance antitumor immunity and CTL proliferation (Zheng P., et al. *Proc. Natl. Acad. Sci. USA* 95 (11):6284–6289 (1998)).

B7 typically is not expressed on tumor cells so they are not efficient antigen presenting cells (APCs) for T cells. Induction of B7 expression would enable the tumor cells to stimulate more efficiently CTL proliferation and effector function. A combination of B7/IL-6/IL-12 costimulation has been shown to induce IFN-gamma and a Th1 cytokine profile in the T cell population leading to further enhanced T cell activity (Gajewski et al., *J. Immunol*, 154:5637–5648 (1995)). Tumor cell transfection with B7 has ben discussed in relation to in vitro CTL expansion for adoptive transfer immunotherapy by Wang et al., (*J. Immunol.*, 19:1–8

(1986)). Other delivery mechanisms for the B7 molecule would include nucleic acid (naked DNA) immunization (Kim J., et al. *Nat Biotechnol.*, 15:7:641–646 (1997)) and recombinant viruses such as adeno and pox (Wendtner et al., *Gene Ther.*, 4:7:726–735 (1997)). These systems are all amenable to the construction and use of expression cassettes for the coexpression of B7 with other molecules of choice such as the antigens or fragment(s) of antigens discussed herein (including polytopes) or cytokines. These delivery systems can be used for induction of the appropriate molecules in vitro and for in vivo vaccination situations. The use of anti-CD28 antibodies to directly stimulate T cells in vitro and in vivo could also be considered.

Lymphocyte function associated antigen-3 (LFA-3) is expressed on APCs and some tumor cells and interacts with CD2 expressed on T cells. This interaction induces T cell IL-2 and IFN-gamma production and can thus complement but not substitute, the B7/CD28 costimulatory interaction (Parra et al., *J. Immunol.*, 158:637–642 (1997), Fenton et al., *J. Immunother.*, 21:2:95–108 (1998)).

Lymphocyte function associated antigen-1 (LFA-1) is expressed on leukocytes and interacts with ICAM-1 expressed on APCs and some tumor cells. This interaction induces T cell IL-2 and IFN-gamma production and can thus complement but not substitute, the B7/CD28 costimulatory interaction (Fenton et al., *J. Immunother.*, 21:2:95–108 (1998)). LFA-1 is thus a further example of a costimulatory molecule that could be provided in a vaccination protocol in the various ways discussed above for B7.

Complete CTL activation and effector function requires Th cell help through the interaction between the Th cell CD40L (CD40 ligand) molecule and the CD40 molecule expressed by DCs (Ridge et al., *Nature*, 393:474 (1998), Bennett et al., *Nature*, 393:478 (1998), Schoenberger et al., *Nature*, 393:480 (1998)). This mechanism of this costimulatory signal is likely to involve upregulation of B7 and associated IL-6/IL-12 production by the DC (APC). The CD40-CD40L interaction thus complements the signal 1 (antigen/MHC-TCR) and signal 2 (B7-CD28) interactions.

The use of anti-CD40 antibodies to stimulate DC cells directly, would be expected to enhance a response to tumor antigens which are normally encountered outside of a inflammatory context or are presented by non-professional APCs (tumor cells). In these situations Th help and B7 costimulation signals are not provided. This mechanism might be used in the context of antigen pulsed DC based therapies or in situations where Th epitopes have not been defined within known TRA precursors.

A cancer associated antigen polypeptide, or a fragment thereof, also can be used to isolate their native binding partners. Isolation of such binding partners may be performed according to well-known methods. For example, isolated cancer associated antigen polypeptides can be attached to a substrate (e.g., chromatographic media, such as polystyrene beads, or a filter), and then a solution suspected of containing the binding partner may be applied to the substrate. If a binding partner which can interact with cancer associated antigen polypeptides is present in the solution, then it will bind to the substrate-bound cancer associated antigen polypeptide. The binding partner then may be isolated.

It will also be recognized that the invention embraces the use of the cancer associated antigen cDNA sequences in expression vectors, as well as to transfect host cells and cell lines, be these prokaryotic (e.g., *E. coli*), or eukaryotic (e.g., dendritic cells, B cells, CHO cells, COS cells, yeast expression systems and recombinant baculovirus expression in insect cells). Especially useful are mammalian cells such as human, mouse, hamster, pig, goat, primate, etc. They may be of a wide variety of tissue types, and include primary cells and cell lines. Specific examples include keratinocytes, peripheral blood leukocytes, bone marrow stem cells and embryonic stem cells. The expression vectors require that the pertinent sequence, i.e., those nucleic acids described supra, be operably linked to a promoter.

The invention also contemplates delivery of nucleic acids, polypeptides or peptides for vaccination. Delivery of polypeptides and peptides can be accomplished according to standard vaccination protocols which are well known in the art. In another embodiment, the delivery of nucleic acid is accomplished by ex vivo methods, i.e. by removing a cell from a subject, genetically engineering the cell to include a breast cancer associated antigen, and reintroducing the engineered cell into the subject. One example of such a procedure is outlined in U.S. Pat. No. 5,399,346 and in exhibits submitted in the file history of that patent, all of which are publicly available documents. In general, it involves introduction in vitro of a functional copy of a gene into a cell(s) of a subject, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo nucleic acid delivery using vectors such as viruses and targeted liposomes also is contemplated according to the invention.

In preferred embodiments, a virus vector for delivering a nucleic acid encoding a cancer associated antigen is selected from the group consisting of adenoviruses, adeno-associated viruses, poxviruses including vaccinia viruses and attenuated poxviruses, Semliki Forest virus, Venezuelan equine encephalitis virus, retroviruses, Sindbis virus, and Ty virus-like particle. Examples of viruses and virus-like particles which have been used to deliver exogenous nucleic acids include: replication-defective adenoviruses (e.g., Xiang et al., *Virology* 219:220–227, 1996; Eloit et al., *J. Virol.* 7:5375–5381, 1997; Chengalvala et al., *Vaccine* 15:335–339, 1997), a modified retrovirus (Townsend et al., *J. Virol.* 71:3365–3374, 1997), a nonreplicating retrovirus (Irwin et al., *J. Virol.* 68:5036–5044, 1994), a replication defective Semliki Forest virus (Zhao et al., *Proc. Natl. Acad. Sci. USA* 92:3009–3013, 1995), canarypox virus and highly attenuated vaccinia virus derivative (Paoletti, *Proc. Natl. Acad. Sci. USA* 93:11349–11353, 1996), non-replicative vaccinia virus (Moss, *Proc. Natl. Acad. Sci. USA* 93:11341–11348, 1996), replicative vaccinia virus (Moss, *Dev. Biol. Stand.* 82:55–63, 1994), Venezuelan equine encephalitis virus (Davis et al., *J. Virol.* 70:3781–3787, 1996), Sindbis virus (Pugachev et al., *Virology* 212:587–594, 1995), and Ty virus-like particle (Allsopp et al., *Eur. J. Immunol* 26:1951–1959, 1996). In preferred embodiments, the virus vector is an adenovirus.

Another preferred virus for certain applications is the adeno-associated virus, a double-stranded DNA virus. The adeno-associated virus is capable of infecting a wide range of cell types and species and can be engineered to be replication-deficient. It further has advantages, such as heat and lipid solvent stability, high transduction frequencies in cells of diverse lineages, including hematopoietic cells, and lack of superinfection inhibition thus allowing multiple series of transductions. The adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In general, other preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Adenoviruses and retroviruses have been approved for human gene therapy trials. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W. H. Freeman Co., New York (1990) and Murry, E. J. Ed. "Methods in Molecular Biology," vol. 7, Humana Press, Inc., Cliffton, N.J. (1991).

Preferably the foregoing nucleic acid delivery vectors: (1) contain exogenous genetic material that can be transcribed and translated in a mammalian cell and that can induce an immune response in a host, and (2) contain on a surface a ligand that selectively binds to a receptor on the surface of a target cell, such as a mammalian cell, and thereby gains entry to the target cell.

Various techniques may be employed for introducing nucleic acids of the invention into cells, depending on whether the nucleic acids are introduced in vitro or in vivo in a host. Such techniques include transfection of nucleic acid-$CaPO_4$ precipitates, transfection of nucleic acids associated with DEAE, transfection or infection with the foregoing viruses including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. Preferred antibodies include antibodies which selectively bind a cancer associated antigen, alone or as a complex with a MHC molecule. Especially preferred are monoclonal antibodies. Where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

When administered, the therapeutic compositions of the present invention can be administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The therapeutics of the invention can be administered by any conventional route, including injection or by gradual infusion over time. The administration may, for example, be oral, intravenous, intraperitoneal, intramuscular, intracavity, subcutaneous, or transdermal. When antibodies are used therapeutically, a preferred route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences*, 18th edition, 1990, pp 1694–1712; incorporated by reference). Those of skill in the art can readily determine the various parameters and conditions for producing antibody aerosols without resort to undue experimentation. When using antisense preparations of the invention, slow intravenous administration is preferred.

The compositions of the invention are administered in effective amounts. An "effective amount" is that amount of a cancer associated antigen composition that alone, or together with further doses, produces the desired response, e.g. increases an immune response to the cancer associated antigen. In the case of treating a particular disease or condition characterized by expression of one or more cancer associated antigens, such as renal cancer, the desired response is inhibiting the progression of the disease. This may involve only slowing the progression of the disease temporarily, although more preferably, it involves halting the progression of the disease permanently. This can be monitored by routine methods or can be monitored according to diagnostic methods of the invention discussed herein. The desired response to treatment of the disease or condition also can be delaying the onset or even preventing the onset of the disease or condition.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The pharmaceutical compositions used in the foregoing methods preferably are sterile and contain an effective amount of cancer associated antigen or nucleic acid encoding cancer associated antigen for producing the desired response in a unit of weight or volume suitable for administration to a patient. The response can, for example, be measured by determining the immune response following administration of the cancer associated antigen composition via a reporter system by measuring downstream effects such as gene expression, or by measuring the physiological effects of the cancer associated antigen composition, such as regression of a tumor or decrease of disease symptoms. Other assays will be known to one of ordinary skill in the art and can be employed for measuring the level of the response.

The doses of cancer associated antigen compositions (e.g., polypeptide, peptide, antibody, cell or nucleic acid) administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

In general, for treatments for eliciting or increasing an immune response, doses of cancer associated antigen are formulated and administered in doses between 1 ng and 1 mg, and preferably between 10 ng and 100 μg, according to any standard procedure in the art. Where nucleic acids encoding cancer associated antigen of variants thereof are employed, doses of between 1 ng and 0.1 mg generally will be formulated and administered according to standard procedures. Other protocols for the administration of cancer associated antigen compositions will be known to one of ordinary skill in the art, in which the dose amount, schedule of injections, sites of injections, mode of administration (e.g., intra-tumoral) and the like vary from the foregoing. Administration of cancer associated antigen compositions to mammals other than humans, e.g. for testing purposes or veterinary therapeutic purposes, is carried out under substantially the same conditions as described above.

Where cancer associated antigen peptides are used for vaccination, modes of administration which effectively deliver the cancer associated antigen and adjuvant, such that an immune response to the antigen is increased, can be used. For administration of a cancer associated antigen peptide in adjuvant, preferred methods include intradermal, intravenous, intramuscular and subcutaneous administration. Although these are preferred embodiments, the invention is not limited by the particular modes of administration disclosed herein. Standard references in the art (e.g., *Remington's Pharmaceutical Sciences*, 18th edition, 1990) provide modes of administration and formulations for delivery of immunogens with adjuvant or in a non-adjuvant carrier.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

A renal cancer associated antigen composition may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise a sterile aqueous or non-aqueous preparation of breast cancer associated antigen polypeptides or nucleic acids, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or di-glycerides. In addition, fatty acids such as oleic acid may be used in the preparation of injectables. Carrier formulation suitable for oral, subcutaneous, intravenous, intramuscular, etc. administrations can be found in *Remington's Pharmaceutical Sciences*, Mack Publishing Co., Easton, Pa.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. An isolated nucleic acid as used herein is not a naturally occurring chromosome.

As used herein with respect to polypeptides, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may, but need not be, substantially pure. The term "substantially pure" means that the proteins or polypeptides are essentially free of other substances with which they may be found in nature or in vivo systems to an extent practical and appropriate for their intended use. Substantially pure polypeptides may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, i.e. isolated from other proteins.

EXAMPLES

Example 1

SEREX Screening of Renal Cancer Cell Line 1973/10.4

A standard cDNA library was prepared using 5 μg of poly A+ RNA derived from the cell line 1973/10.4. A primary (unamplified) cDNA library was immunoscreened (5×10$^5$ clones per library) by standard SEREX methodology, with absorbed autologous patient serum at 1:200 dilution [Sahin, U. et al., Proc Natl Acad Sci USA 92:11810–3 (1995); Chen, Y. T. et al. Proc Natl Acad Sci USA. 94:1914–8 (1997)]. Excluding false-positive clones encoding immunoglobulin gene fragments, clones were purified and sequence analyzed. Comparisons of the sequences showed that these clones represented cDNAs from 22 distinct genes, designated NY-REN-45 through NY-LU-66 (Table A and Sequence Listing (SEQ ID NOs:1–21)). A homology search through the GenBank/EMBO databases revealed that 14 of the 22 genes corresponded to previously known molecules, and 8 others were unknown genes, with sequence identity limited only to short segments of known genes or to expressed sequence tags (ESTs).

Analysis of Isolated Clones:

I. NY-REN clones which are known gene products

| Designation | Gene/Sequence Identity | Accession Number | SEQ ID NO |
|---|---|---|---|
| NY-REN-46 | lactate dehydrogenase B | Y00711 | 22 |
| NY-REN-47 | ERK tyrosine kinase | D31661 | 23 |
| NY-REN-48 | PINCH protein | U09284 | 24 |
| NY-REN-51 | BBP/53BP2 | U58334 | 25 |
| NY-REN-52 | steroid receptor coactivator | U59302 | 26 |
| NY-REN-53 | KIAA0336 mRNA tag | AB002334 | 27 |
| NY-REN-54 | E6 oncogenic protein-associated protein | X98033 | 28 |
| NY-REN-55 | murine NEK1 protein kinase homologue | S45828 | 29 |
| NY-REN-56 | 6-phospho-fructokinase | D49817 | 30 |
| NY-REN-59 | lactate dehydrogenase A | X02152 | 31 |
| NY-REN-61 | KIAA0081 mRNA tag | D42039 | 32 |
| NY-REN-63 | DDB p127-associated protein | AF035950 | 33 |
| NY-REN-65 | HREV107 protein | X92814 | 34 |
| NY-REN-66 | acidic ribosomal phosphoprotein 2 | M17887 | 35 |

TABLE A

Sequences of the Known Genes Identified Among Renal SEREX Clones

```
SEQ ID NO:22
CTTCTCCGCACGACTGTTACAGAGGTCTCCAGAGCCTTCTCTCTCCTGTGCAAAATGGCAACTCTTAAGG
AAAAACTCATTGCACCAGTTGCGGAAGAAGAGGCAACAGTTCCAAACAATAAGATCACTGTAGTGGGTGT
TGGACAAGTTGGTATGGCGTGTGCTATCAGCATTCTGGGAAAGTCTCTGGCTGATGAACTTGCTCTTGTG
GATGTTTTGGAAGATAAGCTTAAAGGAGAAATGATGGATCTGCAGCATGGGAGCTTATTTCTTCAGACAC
CTAAAATTGTGGCAGATAAAGATTATTCTGTGACCGCCAATTCTAAGATTGTAGTGGTAACTGCAGGAGT
CCGTCAGCAAGAAGGGGAGAGTCGGCTCAATCTGGTCAGAGAAATGTTAATGTCTTCAAATTCATTATT
CCTCAGATCGTCAAGTACAGTCCTGATTGCATCATAATTGTGGTTTCCAACCCAGTGGACATTCTTACGT
ATGTTACCTGGAAACTAAGTGGATTACCCAAACACCGCGTGATTGGAAGTGGATGTAATCTGGATTCTGC
TAGATTTCGCTACCTTATGGCTGAAAAACTTGGCATTCATCCCAGCAGCTGCCATGGATGGATTTTGGGG
GAACATGGCGACTCAAGTGTGGCTGTGTGGAGTGGTGTGAATGTGGCAGGTGTTTCTCTCCAGGAATTGA
ATCCAGAAATGGGAACTGACAATGATAGTGAAAATTGGAAGGAAGTGCATAAGATGGTGGTTGAAAGTGC
CTATGAAGTCATCAAGCTAAAAGGATATACCAACTGGGCTATTGGATTAAGTGTGGCTGATCTTATTGAA
TCCATGTTGAAAAATCTATCCAGGATTCATCCCGTGTCAACAATGGTAAAGGGGATGTATGGCATTGAGA
ATGAAGTCTTCCTGAGCCTTCCATGTATCCTCAATGCCCGGGGATTAACCAGCGTTATCAACCAGAAGCT
AAAGGATGATGAGGTTGCTCAGCTCAAGAAAAGTGCAGATACCCTGTGGGACATCCAGAAGGACCTAAAA
GACCTGTGACTAGTGAGCTCTAGGCTGTAGAAATTTAAAAACTACAATGTGATTAACTCGAGCCTTTAGT
TTTCATCCATGTACATGGATCACAGTTTGCTTTGATCTTCTTCAATATGTGAATTTGGGCTCACAGAATC
AAAGCCTATGCTTGGTTTAATGCTTGCAATCTGAGCTCTTGAACAAATAAAATTAACTATTGTAGTGTGA
```

TABLE A-continued

Sequences of the Known Genes Identified Among Renal SEREX Clones

SEQ ID NO:23
TAACACAGTTGTGAAAAGAGATGGATGTGGGTTCCAGTCCTAGCCCTGCCTGTGTGCACTTATGCAGAAA
CGCTAATGGACTCCACTACAGCGACTGCTGAGCTGGGCTGGATGGTGCATCCTCCATCAGGGTGGGAAGA
GGTGAGTGGCTACGATGAGAACATGAACACGATCCGCACGTACCAGGTGTGCAACGTGTTTGAGTCAAGC
CAGAACAACTGGCTACGGACCAAGTTTATCCGGCGCCGTGGCGCCCACCGCATCCACGTGGAGATGAAGT
TTTCGGTGCGTGACTGCAGCAGCATCCCCAGCGTGCCTGGCTCCTGCAAGGAGACCTTCAACCTCTATTA
CTATGAGGCTGACTTTGACTCGGCCACCAAGACCTTCCCCAACTGGATGGAGAATCCATGGGTGAAGGTG
GATACCATTGCAGCCGACGAGAGCTTCTCCCAGGTGGACCTGGGTGACCGCGTCATGAAAATCAACACCG
AGGTGCGGAGCTTCGGACCTGTGTCCCGCAGCGGCTTCTACCTGGCCTTCCAGGACTATGGCGGCTGCAT
GTCCCTCATCGCCGTGCGTGTCTTCTACCGCAAGTGCCCCGCATCATCCAGAATGGCGCCATCTTCCAG
GAAACCCTGTCGGGGGCTGAGAGCACATCGCTGGTGGCTGCCCGGGGCAGCTGCATCGCCAATGCGGAAG
AGGTGGATGTACCCATCAAGCTCTACTGTAACGGGGACGGCGAGTGGCTGGTGCCCATCGGGCGCTGCAT
GTGCAAAGCAGGCTTCGAGGCCGTTGAGAATGGCACCGTCTGCCGAGGTTGTCCATCTGGGACTTTCAAG
GCCAACCAAGGGGATGAGGCCTGTACCCACTGTCCCATCAACAGCCGGACCACTTCTGAAGGGGCCACCA
ACTGTGTCTGCCGCAATGGCTACTACAGAGCAGACCTGGACCCCCTGGACATGCCCTGCACAACCATCCC
CTCCGCGCCCCAGGCTGTGATTTCCAGTGTCAATGAGACCTCCCTCATGCTGGAGTGGACCCCTCCCCGC
GACTCCGGAGGCCGAGAGGACCTCGTCTACAACATCATCTGCAAGAGCTGTGGCTCGGGCCGGGGTGCCT
GCACCCGCTGCGGGGACAATGTACAGTACGCACCACGCCAGCTAGGCCTGACCGAGCCACGCATTTACAT
CAGTGACCTGCTGGCCCACACCCAGTACACCTTCGAGATCCAGGCTGTGAACGGCGTTACTGACCAGAGC
CCCTTCTCGCCTCAGTTCGCCTCTGTGAACATCACCACCAACCAGGCAGCTCCATCGGCAGTGTCCATCA
TGCATCAGGTGAGCCGCACCGTGGACAGCATTACCCTGTCGTGGTCCCAGCCAGACCAGCCCAATGGCGT
GATCCTGGACTATGAGCTGCAGTACTATGAGAAGCAGGAGCTCAGTGAGTACAACGCCACAGCCATAAAA
AGCCCCACCAACACGGTCACCGTGCAGGGCCTCAAAGCCGGCGCCATCTATGTCTTCCAGGTGCGGGCAC
GCACCGTGGCAGGCTACGGGCGCTACAGCGGCAAGATGTACTTCCAGACCATGACAGAAGCCGATTACCA
GACAAGCATCCAGGAGAAGTTGCCACTCATCATCGGCTCCTCGGCCGCTGGCCTGGTCTTCCTCATTGCT
GTGGTTGTCATCGCCATCGTGTGTAACAGACGGGGGTTTGAGCGTGCTGACTCGGAGTACACGGACAAGC
TGCAACACTACACCAGTGGCCACATGACCCCAGGCATGAAGATCTACATCGATCCTTTCACCTACGAGGA
CCCCAACGAGGCAGTGCGGGAGTTTGCCAAGGAAATTGACATCTCCTGTGTCAAAATTGAGCAGGTGATC
GGAGCAGGGGAGTTTGGCGAGGTCTGCAGTGGCCACCTGAAGCTGCCAGGCAAGAGAGAGATCTTTGTGG
CCATCAAGACGCTCAAGTCGGGCTACACGGAGAAGCAGCGCCGGGACTTCCTGAGCGAAGCCTCCATCAT
GGGCCAGTTCGACCATCCCAACGTCATCCACCTGGAGGGTGTCGTGACCAAGAGCACACCTGTGATGATC
ATCACCGAGTTCATGGAGAATGGCTCCCTGGACTCCTTTCTCCGGCAAAACGATGGGCAGTTCACAGTCA
TCCAGCTGGTGGGCATGCTTCGGGGCATCGCAGCTGGCATGAAGTACCTGGCAGACATGAACTATGTTCA
CCGTGACCTGGCTGCCCGCAACATCCTCGTCAACAGCAACCTGGTCTGCAAGGTGTCGGACTTTGGGCTC
TCACGCTTTCTAGAGGACGATACCTCAGACCCCACCTACACCAGTGCCCTGGGCGGAAAGATCCCCATCC
GCTGGACAGCCCCGGAAGCCATCCAGTACCGGAAGTTCACCTCGGCCAGTGATGTGTGGAGCTACGGCAT
TGTCATGTGGGAGGTGATGTCCTATGGGGAGCGGCCCTACTGGGACATGACCAACCAGGATGTAATCAAT
GCCATTGAGCAGGACTATCGGCTGCCACCGCCCATGGACTGCCCAGCTGCCCTGCACCAACTCATGCTGG
ACTGTTGGCAGAAGGACCGCAACCACCGGCCCAAGTTCGGCCAAATTGTCAACACGCTAGACAAGATGAT
CCGCAATCCCAACAGCCTCAAAGCCATGGCGCCCCTCTCCTCTGGCATCAACCTGCCGCTGCTGGACCGC
ACGATCCCCGACTACACCAGCTTTAACACGGTGGACGAGTGGCTGAAGGCCATCAAGATGGGGCAGTACA
AGGAGAGCTTCGCCAATGCCGGCTTCACCTCCTTTGACGTCGTGTCTCAGATGATGATGGAGGACATTCT
CCGGGTTGGGGTCACTTTGGCTGGCCACCAGAAAAAATCCTGAACAGTATCCAGGTGATGCGGGCGCAG
ATGAACCAGATTCAGTCTGTGGAGGTTTGACATTCACCTGCCTCGGCTCACCTCTTCCTCCAAGCCCCGC
CCCCTCTGCCCCACGTGCCGGCCCTCCTGGTGCTCATCCACTGCAGGGCCAGCCACTCGCCAGGAGGCC
ACGGGCACGGGAAGAACCAAGCGGTGCCAGCCACGAGACGTCACCAAGAAAACATGCAACTCAAACGACG
G

SEQ ID NO:24
TAGTTCAAGACAACAGAGACAAAGCTAAGATGAGGAAGTTCTGTACAGTTTAGGAAATAGAGGCTTTCAA
AGATAATTCGCAGTGATGTGAAACTGGCCTCCCAAGCCCTGATAACAACATGGCCAACGCCCTGGCCAGC
GCCACTTGCGAGCGCTGCAAGGGCGGCTTTGCGCCCGCTGAGAAGATCGTGAACAGTAATGGGGAGCTGT
ACCATGAGCAGTGTTTCGTGTGCGCTCAGTGCTTCCAGCAGTTCCCAGAAGGACTCTTCTATGAGTTTGA
AGGAAGAAAGTACTGTGAACATGACTTTCAGATGCTCTTTGCCCCCTTGCTGTCATCAGTGTGGTGAATTC
ATCATTGGCCGAGTTATCAAAGCCATGAATAACAGCTGGCATCCGGAGTGCTTCCGCTGTGACCTCTGCC
AGGAAGTTCTGGCAGATATCGGGTTTGTCAAGAATGCTGGGAGACACCTGTGTCGCCCCTGTCATAATCG
TGAGAAAGCCAGAGGCCTTGGGAAATACATCTGCCAGAAATGCCATGCTATCATCGATGAGCAGCCTCTG
ATATTCAAGAACGACCCCTACCATCCAGACCATTTCAACTGCGCCAACTGCGGGAAGGAGCTGACTGCCG
ATGCACGGGAGCTGAAAGGGGAGCTATACTGCCTCCCATGCCATGATAAAATGGGGGTCCCCATCTGTGG
TGCTTGCCGACGGCCCATCGAAGGGCGCGTGGTGAACGCTATGGGCAAGCAGTGGCATGTGGAGCATTTT
GTTTGTGCCAAGTGTGAGAAACCCTTTCTTGGACATCGCCATTATGAGAGGAAAGGCCTGGCATATTGTG
AAACTCACTATAACCAGCTATTTGGTGATGTTTGCTTCCACTGCAACTGTGTTATAGAAGGTGATGTGGT
CTCTGCTCTTAATAAGGCCTGGTGCGTGAACTGCTTTGCCTGTTCTACCTGCAACACTAAATTAACACTC
AAGAATAAGTTTGTGGAGTTTGACATGAAGCCAGTCTGTAAGAAGTGCTATGAGATTTCCATTGGAGCTG
AAGAAAAGACTTAAGAAACTAGCTGAGACCTTAGGAAGGAAATAAGTTCCTTTATTTTTTCTTTTCTATG
CAAGATAAGAGATTACCAACATTACTTGTCTTGATCTACCCATATTTAAAGCTATATCTCAAAGCAGTTG
AGAGAAGAGGACCTATATGAATGGTTTTATGTCATTTTTTTAAA

SEQ ID NO:25
GTCACGAGCGTCGAAGAGACAAAGCCGCGTCAGGGGGCCCGGCCGGGGCGGGGAGCCCGGGGCTTGTTG
GTGCCCCAGCCCGCGCGGAGGGCCCTTCGGACCCGCGCGCCGCCGCTGCCGCCGCCGCCGCCTCGCAACA
GGTCCGGGCGGCCTCGCTCTCCGCTCCCCTCCCCCGCATCCGCGACCCTCCGGGGCACCTCAGCTCGGCC
GGGGCCGCAGTCTGGCCACCCGCTTCCATGCGGTTCGGGTCCAAGATGATGCCGATGTTTCTTACCGTGT
ATCTCAGTAACAATGAGCAGCACTTCACAGAAGTTCCAGTTACTCCAGAAACAATATGCAGAGACGTGGT
GGATCTGTGCAAAGAACCCGGCGAGAGTGATTGCCATTTGGCTGAAGTGTGGTGTTGGCTCTGTAGAGATA
GAGTTTCATCATGTTGGCCAGGATGGTCTCGATCTCCTGACCTTGTGATCCGCCTGCCTCGGCCTCCCAA

TABLE A-continued

Sequences of the Known Genes Identified Among Renal SEREX Clones

AGTGCTGGATTACAGGTGTGAGCCACCACGATCAGCCTCTAGTGTTTAAAAAAGAACGTCCAGTTGCGGA
TAATGAGCGAATGTTTGATGTTCTTCAACGATTTGGAAGTCAGAGGAACGAAGTTCGCTTCTTCCTTCGT
CATGAACGCCCCCCTGGCAGGGACATTGTGAGTGGACCAAGATCTCAGGATCCAAGTTTAAAAAGAAATG
GTGTAAAAGTTCCTGGTGAATATCGAAGAAAGGAGAACGGTGTTAATAGTCCTAGGATGGATCTGACTCT
TGCTGAACTTCAGGAAATGGCATCTCGCCAGCAGCAACAGATTGAAGCCCGCCAACAATTGCTGGCAACT
AAGGAACAGCGCTTAAAGTTTTTGAAACAACAAGATCAGCGACAACAGCAACAAGTTGCTGAGCAGGAGA
AACTTAAAAGGCTAAAAGAAATAGCTGAGAATCAGGAAGCTAAGCTAAAAAAAGTGAGAGCACTTAAAGG
CCACGTGGAACAGAAGAGACTAAGCAATGGGAAACTTGTGGAGGAAATTGAACAGATGAATAATTTGTTC
CAGCAAAAACAGAGGGAGCTCGTCCTGGCTGTGTCAAAAGTAGAAGAACTGACCAGGCAGCTAGAGATGC
TCAAGAACGGCAGGATCGACAGCCACCATGACAATCAGTCTGCAGTGGCTGAGCTTGATCGCCTCTATAA
GGAGCTGCAGCTAAGAAACAAATTGAATCAAGAGCAGAATGCCAAGCTACAACAACAGAGGGAGTGTTTG
AATAAGCGTAATTCAGAAGTGGCAGTCATGGATAAGCGTGTTAATGAGCTGAGGGACCGGCTGTGGAAGA
AGAAGGCAGCTCTACAGCAAAAAGAAAATCTACCAGTTTCATCTGATGGAAATCTTCCCCAGCAAGCCGC
GTCAGCCCCAAGCCGTGTGGCTGCAGTAGGTCCCTATATCCAGTCATCTACTATGCCTCGGATGCCCTCA
AGGCCTGAATTGCTGGTGAAGCCAGCCCTGCCGGATGGTTCCTTGGTCATTCAGGCTTCAGAGGGGCCGA
TGAAAATACAGACACTGCCCAACATGAGATCTGGGGCTGCTTCACAAACTAAAGGCTCTAAAATCCATCC
AGTTGGCCCTGATTGGAGTCCTTCAAATGCAGATCTTTTCCCAAGCCAAGGCTCTGCTTCTGTACCTCAA
AGCACTGGGAATGCTCTGGATCAAGTTGATGATGGAGAGGTTCCGCTGAGGGAGAAAGAGAAGAAAGTGC
GTCCGTTCTCAATGTTTGATGCAGTAGACCAGTCCAATGCCCCACCTTCCTTTGGTACTCTGAGGAAGAA
CCAGAGCAGTGAAGATATCTTGCGGGATGCTCAGGTTGCAAATAAAAATGTGGCTAAAGTACCACCTCCT
GTTCCTACAAAACCAAAACAGATTAATTTGCCTTATTTTGGACAAACTAATCAGCCACCTTCAGACATTA
AGCCAGACGGAAGTTCTCAGCAGTTGTCAACAGTTGTTCCGTCCATGGGAACTAAACCAAAACCAGCAGG
GCAGCAGCCGAGAGTGCTGCTATCTCCCAGCATACCTTCGGTTGGCCAAGACCAGACCCTTTCTCCAGGT
TCTAAGCAAGAAAGTCCACCTGCTGCTGCCGTCCGGCCCTTTACTCCCCAGCCTTCCAAAGACACCTTAC
TTCCACCCTTCAGAAAACCCCAGACCGTGGCAGCAAGTTCAATATATTCCATGTATACGCAACAGCAGGC
GCCAGGAAAAAACTTCCAGCAGGCTGTGCAGAGCGCGTTGACCAAGACTCATACCAGAGGGCCACACTTT
TCAAGTGTATATGGTAAGCCTGTAATTGCTGCTGCCCAGAATCAACAGCAGCACCCAGAGAACATTTATT
CCAATAGCCAGGGCAAGCCTGGCAGTCCAGAACCTGAAACAGAGCCTGTTTCTTCAGTTCAGGAGAACCA
TGAAAACGAAAGAATTCCTCGGCCACTCAGCCCAACTAAATTACTGCCTTTCTTATCTAATCCTTACCGA
AACCAGAGTGATGCTGACCTAGAAGCCTTACGAAAGAAACTGTCTAACGCACCAAGGCCTCTAAAGAAAC
GTAGTTCTATTACAGAGCCAGAGGGTCCTAATGGGCCAAATATTCAGAAGCTTTTATATCAGAGGACCAC
CATAGCGGCCATGGAGACCATCTCTGTCCCATCATACCCATCCAAGTCAGCTTCTGTGACTGCCAGCTCA
GAAAGCCCAGTAGAAATCCAGAATCCATATTTACATGTGGAGCCCGAAAAGGAGGTGGTCTCTCTGGTTC
CTGAATCATTGTCCCCAGAGGATGTGGGGAATGCCAGTACAGAGAACAGTGAAGTGTGTAAGTTTTTGGTGGAGTCAG
GAGCCGCTGTGTTTGCCATGACCTACAGTGACATGCAGACTGCTGCAGATAAGTGCGAGGAAATGGAGGA
AGGCTACACTCAGTGCTCCCAATTTCTTTATGGAGTTCAGGAGAAGATGGGCATAATGAATAAAGGAGTC
ATTTATGCGCTTTGGGATTATGAACCTCAGAATGATGATGAGCTGCCCATGAAAGAAGGAGACTGCATGA
CAATCATCCACAGGGAAGACGAAGATGAAATCGAATGGTGGTGGGCGCGCCTTAATGATAAGGAGGGATA
TGTTCCACGTAACTTGCTGGGACTGTACCCAAGAATTAAACCAAGACAAAGGAGCTTGGCCTGAAACTTC
CACACAGAATTTTAGTCAATGAAGAATTAATCTCTGTTAAGAAGAAGTAATACGATTATTTTTGGCAAAA
ATTTCACAAGACTTATTTTAATGACAATGTAGCTTGAAAGCGATGAAGAATGTCTCTAGAAGAGAATGAA
GGATTGAAGAATTCACCATTAGAGGACATTTAGCGTGATGAAATAAAGCATCTACGTCAGCAGGCCATAC
TGTGTTGGGGCAAAGGTGTCCCGTGTAGCACTCAGATAAGTATACAGCGACAATCCTGTTTTCTACAAGA
ATCCTGTCTAGTAAATAGGATCATTTATTGGGCAGTTGGGAAATCAGCTCTCTGTCCTGTTGAGTGTTTT
CAGCAGCTGCTCCTAAACCAGTCCTCCTGCCAGAAAGGACCAGTGCCGTCACATCGCTGTCTCTGATTGT
CCCCGGCACCAGCAGGCCTTGGGGCTCACTGAAGGCTCGAAGGCACTGCACACCTTGTATATTGTCAGTG
AAGAACGTTAGTTGGTTGTCAGTGAACAATAACTTTATTATATGAGTTTTTGTAGCATCTTAAGAATTAT
ACATATGTTTGAAATATTGAAACTAAGCTACAGTACCAGTAATTAGATGTAGAATCTTGTTTGTAGGCTG
AATTTTAATCTGTATTTATTGTCTTTTGTATCTCAGAAATTAGAAACTTGCTACAGACTTACCCGTAATA
TTTGTCAAGATCATAGCTGACTTTAAAAACAGTTGTAATAAACTTTTTGATGCT

SEQ ID NO:26
GGGGCTTAGAAATTAACAGGTTGTTTATATAATTGGCCTTAAATGAGGTGAGAGTGAAGAGACTAGAGCC
ATCTCTGGAAAACATCATTATCCCATTCCCCGGGAAGCTACCCTCTGGAACTCAAGATTTGACCATATCT
GTTTTGAGGATTCATTATGAACAAAGAAGTCTCCCAGGTGTGAAGTTTTTCAACATGAGTGGCCTCGGGG
ACAGTTCATCCGACCCTGCTAACCCAGACTCACATAAGAGGAAAGGATCGCCATGTGACACACTGGCATC
AAGCACGGAAAAGAGGCGCAGGGAGCAAGAAAATAAATATTTAGAAGAACTAGCTGAGTTACTGTCTGCC
AACATTAGTGACATTGACAGCTTGAGTGTAAAACCAGACAAATGCAAGATTTTGAAGAAAACAGTCGATC
AGATACAGCTAATGAAGAGAATGGAACAAGAGAAATCAACAACTGATGACGATGTACAGAAATCAGACAT
CTCATCAAGTAGTCAAGGAGTGATAGAAAAGGAATCCTTGGGACCCCTTCTTTTGGAGGCTTTGGATGGA
TTTTTCTTTGTTGTGAACTGTGAAGGGAGAATTGTATTTGTGTCAGAGAATGTAACCAGCTACTTAGGTT
ACAATCAGGAGGAATTAATGAATACCAGCGTCTACAGCATACTGCACGTGGGGGATCATGCAGAATTTGT
GAAGAATCTGCTACCAAAATCACTAGTAAATGGAGTTCCTTGGCCTCAAGAGGCAACACGACGAAATAGC
CATACCTTTAACTGCAGGATGCTAATTCACCCTCCAGATGAGCCAGGGACCGAGAACCAAGAAGCTTGCC
AGCGTTATGAAGTAATGCAGTGTTTCACTGTGTCACAGCCAAATCAATTCAAGAGGATGGAGAAGATTT
CCAGTCATGTCTGATTTGTATTGCACGGCGATTACCTCCGCCTCCAGCTATTACGGGTGTAGAATCCTTT
ATGACCAAGCAAGATACTACAGGTAAAATCATCTCTATTGATACTAGTTCCCTGAGAGCTGCTGGCAGAA
CTGGTTGGGAAGATTTAGTGAGGAAGTGCATTTATGCTTTTTTCCAACCTCAGGGCAGAGAACCATCTTA
TGCCAGACAGCTGTTCCAAGAAGTGATGACTCGTGGCACTGCCTCCAGCCCCTCCTATAGATTCATATTG

TABLE A-continued

Sequences of the Known Genes Identified Among Renal SEREX Clones

```
AATGATGGGACAATGCTTAGCGCCCACACCAAGTGTAAACTTTGCTACCCTCAAAGTCCAGACATGCAAC
CTTTCATCATGGGAATTCATATCATCGACAGGGAGCACAGTGGGCTTTCTCCTCAAGATGACACTAATTC
TGGAATGTCAATTCCCCGAGTAAATCCCTCGGTCAATCCTAGTATCTCTCCAGCTCATGGTGTGGCTCGT
TCATCCACATTGCCACCATCCAACAGCAACATGGTATCCACCAGAATAAACCGCCAGCAGAGCTCAGACC
TTCATAGCAGCAGTCATAGTAATTCTAGCAACAGCCAAGGAAGTTTCGGATGCTCACCCGGAAGTCAGAT
TGTAGCCAATGTTGCCTTAAACCAAGGACAGGCCAGTTCACAGAGCAGTAATCCCTCTTTAAACCTCAAT
AATTCTCCTATGGAAGGTACAGGAATATCCCTAGCACAGTTCATGTCTCAAGGAGACAGGTTACTTCTG
GATTGGCAACAAGGCCCAGGATGCCAAACAATTCCTTTCCTCCTAATATTTCGACATTAAGCTCTCCCGT
TGGCATGACAAGTAGTGCCTGTAATAATAATAACCGATCTTATTCAAACATCCCAGTAACATCTTTACAG
GGTATGAATGAAGGACCCAATAACTCCGTTGGCTTCTCTGCCAGTTCTCCAGTCCTCAGGCAGATGAGCT
CACAGAATTCACCTAGCAGATTAAATATACAACCAGCAAAAGCTGAGTCAAAGATAACAAAGAGATTGC
CTCAATTTTAAATGAAATGATTCAATCTGACAACAGCTCTAGTGATGGCAAACCTCTGGATTCAGGGCTT
CTGCATAACAATGACAGACTTTCAGATGGAGACAGTAAATACTCTCAAACCAGTCACAAACTAGTGCAGC
TTTTGACAACAACTGCCGAACAGCAGTTACGGCATGCTGATATAGACACAAGCTGCAAAGATGTCCTGTC
TTGCACAGGCACTTCCAACTCTGCCTCTGCTAACTCTTCAGGAGGTTCTTGTCCCTCTTCTCATAGCTCA
TTGACAGAACGGCATAAAATTCTACACCGGCTCTTACAGGAGGGTAGCCCCTCAGATATCACCACTTTGT
CTGTCGAGCCTGATAAAAAGGACAGTGCATCTACTTCTGTGTCAGTGACTGGACAGGTACAAGGAAACTC
CAGTATAAAACTAGAACTGGATGCTTCAAAGAAAAAAGAATCAAAAGACCATCAGCTCCTACGCTATCTT
TTAGATAAAGATGAGAAAGATTTAAGATCAACTCCAAACCTGAGCCTGGATGATGTAAAGGTGAAAGTGG
AAAAGAAAGAACAGATGGATCCATGTAATACAAACCCAACCCCAATGACCAAACCCACTCCTGAGGAAAT
AAAACTGGAGGCCCAGAGCCAGTTTACAGCTGACCTTGACCAGTTTGATCAGTTACTGCCCACGCTGGAG
AAGGCAGCACAGTTGCCAGGCTTATGTGAGACAGACAGGATGGATGGTGCGGTCACCAGTGTAACCATCA
AATCGGAGATCCTGCCAGCTTCACTTCAGTCCGCCACTGCCAGACCCACTTCCAGGCTAAATAGATTACC
TGAGCTGGAATTGGAAGCAATTGATAACCAATTTGGACAACCAGGAACAGGCGATCAGATTCCATGGACA
AATAATACAGTGACAGCTATAAATCAGAGTAAATCAGAAGACCAGTGTATTAGCTCACAATTAGATGAGC
TTCTCTGTCCACCCACAACAGTAGAAGGGAGAAATGATGAGAAGGCTCTTCTTGAACAGCTGGTATCCTT
CCTTAGTGGCAAAGATGAAACTGAGCTAGCTGAACTAGACAGAGCTCTGGGAATTGACAAACTTGTTCAG
GGGGGTGGATTAGATGTATTATCAGAGAGATTTCCACCAACAAGCAACGCCACCTTTGATCATGGAAG
AAAGACCCAACCTTTATTCCCAGCCTTACTCTTCTCCTTCTCCTACTGCCAATCTCCCTAGCCCTTTCCA
AGGCATGGTCAGGCAAAAACCTTCACTGGGGACGATGCCTGTTCAAGTAACACCTCCCCGAGGTGCTTTT
TCACCTGGCATGGGCATGCAGCCCAGGCAAACTCTAAACAGACCTCCGGCTGCACCTAACCAGCTTCGAC
TTCAACTACAGCAGCGATTACAGGGACAACAGCAGTTGATACACCAAAATCGGCAAGCTATCTTAAACCA
GTTTGCAGCAACTGCTCCTGTTGGCATCAATATGAGATCAGGCATGCAACAGCAAATTACACCTCAGCCA
CCCCTGAATGCTCAAATGTTGGCACAACGTCAGCGGGAACTGTACAGTCAACAGCACCGACAGAGGCAGC
TAATACAGCAGCAAAGAGCCATGCTTATGAGGCAGCAAAGCTTTGGGAACAACCTCCCTCCCTCATCTGG
ACTACCAGTTCAAATGGGGAACCCCGTCTTCCTCAGGGTGCTCCACAGCAATTCCCTATCCACCAAAC
TATGGTACAAATCCAGGAACCCCACCTGCTTCTACCAGCCCGTTTTCACAACTAGCAGCAAATCCTGAAG
CATCCTTGGCCAACCGCAACAGCATGGTGAGCAGAGGCATGACAGGAAACATAGGAGGACAGTTTGGCAC
TGGAATCAATCCTCAGATGCAGCAGAATGTCTTCCAGTATCCAGGAGCAGGAATGGTTCCCCAAGGTGAG
GCCAACTTTGCTCCATCTCTAAGCCCTGGGAGCTCCATGGTGCCGATGCCAATCCCTCCTCCTCAGAGTT
CTCTGCTCCAGCAAACTCCACCTGCCTCCGGGTATCAGTCACCAGACATGAAGGCCTGGCAGCAAGGAGC
GATAGGAAACAACAATGTGTTCAGTCAAGCTGTCCAGAACCAGCCCAGCCCTGCACAGCCCAGGAGTATAC
AACAACATGAGCATCACCGTTTCCATGGCAGGTGGAAATACGAATGTTCAGAACATGAACCCAATGATGG
CCCAGATGCAGATGAGCTCTTTGCAGATGCCAGGAATGAACACTGTGTGCCCTGAGCAGATAAATGATCC
CGCACTGAGACACACAGGCCTCTACTGCAACCAGCTCTCATCCACTGACCTTCTCAAAACAGAAGCAGAT
GGAACCCAGGTGCAACAGGTTCAGGTGTTTGCTGACGTCCAGTGTACAGTGAATCTGGTAGGCGGGGACC
CTTACCTGAACCAGCCTGGTCCACTGGGAACTCAAAAGCCCACGTCAGGACCACAGACCCCCCAGGCCCA
GCAGAAGAGCCTCCTTCAGCAGCTACTGACTGAATAACCACTTTTAAAGGAATGTGAAATTTAAATAATA
GACATACAGAGATATACAAATATATTATATATTTTTCTGAGATTTTTGATATCTCAATCTGCAGCCATTC

SEQ ID NO:27
GCGGCTGGTTGCGGGCCGGCGGCGGGCTGGCGGAGATGGAGGATCTTGTTCAAGATGGGGTGGCTTCACC
AGCTACCCCTGGGACCGGGAAATCTAAGAATTGGAGAAAGAAATTGAAGAACTCAGATCAAAACCTGTTA
CTGAAGGAACTGGTGATATTATTAAGGCATTAACTGAACGTCTGGATGCTCTTCTTCTGGAAAAAGCAGA
GACTGAGCAACAGTGTCTTTCTCTGAAAAAGGAAAATATAAAAATGAAGCAAGAGGTTGAGGATTCTGTA
ACAAAGATGGGAGATGCACATAAGGAGTTGGAACAATCACATATAAACTATGTGAAAGAAATTGAAAATT
TGAAAAATGAGTTGATGGCAGTACGTTCCAAATACAGTGAAGACAAAGCTAACTTACAAAAGCAGCTGGA
AGAAGCAATGAATACGCAATTAGAACTTTCAGAACAACTTAAATTTCAGAACAACTCTGAAGATAATGTT
AAAAAACTACAAGAAGAGATTGAGAAAATTAGGCCAGGCTTTGAGGAGCAAATTTTATATCTGCAAAAGC
AATTAGACGCTACCACTGATGAAAAGAAGGAAACAGTTACTCAACTCCAAAATATCATTGAGGCTAATTC
TCAGCATTACCAAAAAATATTAATAGTTTGCAGGAAGAGCTTTTACAGTTGAAAGCTATACACCAAGAA
GAGGTGAAAGAGTTGATGTGCCAGATTGAAGCATCAGCTAAGGAACATGAAGCAGAGATAAATAAGTTGA
ACGAGCTAAAAGAGAACTTAGTAAAACAATGTGAGGCAAGTGAAAAGACATCCAGAAGAAATATGAATG
TGAGTTAGAAAATTTAAGGAAAGCCACCTCAAATGCAAACCAAGACAATCAGATATGTTCTATTCTCTTG
CAAGAAAATACATTTGTAGAACAAGTAGTAAATGAAAAGTCAAACACTTAGAAGATACCTTAAAAGAAC
TTGAATCTCAACACAGTATCTTAAAAGATGAGGTAACTTATATGAATAATCTTAAGTTAAAACTTGAAAT
GGATGCTCAACATATAAAGGATGAGTTTTTCATGAACGGGAAGCTTAGAGTTTAAAATTAATGAATTA
TTACTAGCTAAAGAAGAACAGGGCTGTGTAATTGAAAAATTAAAATCTGAGCTAGCAGGTTTAAATAAAC
AGTTTTGCTATACTGTAGAACAGCATAACAGAGAAGTACAGAGTCTTAAGGAACAACATCAAAAAGAAAT
ATCAGAACTAAATGAGACATTTTTGTCAGATTCAGAAAAAGAAAAATTAACATTAATGTTTGAAATACAG
GGTCTTAAGGAACAGTGTGAAAACCTACAGCAAGAAAAGCAAGAAGCAATTTTAAATTATGAGAGTTTAC
GAGAGATTATGGAAATTTTACAAACAGAACTGGGGGAATCTGCTGGAAAAATAAGTCAAGAGTTCGAATC
AATGAAGCAACAGCAAGCATCTGATGTTCATGAACTGCAGCAGAAGCTCAGAACTGCTTTTACTGAAAAA
GATGCCCTTCTCGAAACTGTGAATCGCCTCCAGGGAGAAATGAAAGTTACTATCTCAACAAGAATTGG
TACCAGAACTTGAAAATACCATAAAGAACCTTCAAGAAAAGAATGGAGTATACTTACTTAGTCTCAGTCA
AAGAGATACCATGTTAAAAGAATTAGAAGGAAAGATAAATTCTCTTACTGAGGAAAAAGATGATTTTATA
AATAAACTGAAAAATTCCCATGAAGAAATGGATAAATTTCCATAAGAAATGTGAAAGGGAAGAAAGATTGA
```

TABLE A-continued

Sequences of the Known Genes Identified Among Renal SEREX Clones

TTCTTGAACTTGGGAAGAAAGTAGAGCAAACAATCCAGTACAACAGTGAACTAGAACAAAAGGTAAATGA
ATTAACAGGAGGACTAGAGGAGACTTTAAAAGAAAAGGATCAAAATGACCAAAAACTAGAAAAACTTATG
GTTCAAATGAAAGTTCTCTCTGAAGACAAAGAAGTATTGTCAGCTGAAGTGAAGTCTCTTTATGAGGAAA
ACAATAAACTCAGTTCAGAAAAAAAACAGTTGAGTAGGGATTTGGAGGTTTTTTTGTCTCAAAAAGAAGA
TGTTATCCTTAAAGAACATATTACTCAATTAGAAAAGAAACTTCAGTTAATGGTTGAAGAGCAAGATAAT
TTAAATAAACTGCTTGAAAATGAGCAAGTTCAGAAGTTATTTGTTAAAACTCAGTTGTATGGTTTTCTTA
AAGAAATGGGATCAGAAGTTTCAGAAGACAGTGAAGAGAAAGATGTTGTTAATGTCCTACAGGCAGTCGG
TGAATCCTTGGCAAAAATAAATGAGGAAAAATGCAACCTGGCTTTTCAGCGTGATGAAAAAGTATTAGAG
TTAGAAAAAGAGATTAAGTGCCTTCAAGAAGAGAGTGTAGTTCAGTGTGAAGAACTTAAGTCTTTATTGA
GAGACTATGAGCAAGAGAAAGTTCTCTTAAGGAAAGAGTTAGAAGAAATACAGTCAGAAAAAGAGGCCCT
GCAGTCTGATCTTCTAGAAATGAAGAATGCTAATGAAAAACAAGGCTTGAAATCAGAATCTTTTAATT
CAAGTTGAAGAAGTATCTCAAACATGTAGCAAAAGTGAAATCCATAATGAAAAAGAAAAATGTTTTATAA
AGGAACATGAAAACCTAAAGCCACTACTAGAACAAAAAGAATTACGAGATAGGAGAGCAGAGTTGATACT
ATTAAAGGATTCCTTAGCAAAATCACCTTCTGTAAAAAATGATCCTCTGTCTTCAGTAAAAGAGTTGGAA
GAAAAAATAGAAAATCTGGAAAAAGAATGCAAAGAAAAGGAGGAGAAAATAAATAAGATAAAATTAGTTG
CCGTAAAGGCAAAGAAAGAACTAGATTCCAGCAGAAAAGAGACCCAGACTGTGAAGGAAGAACTTGAATC
TCTTCGATCAGAAAAGGACCAGTTATCTGCTTCCATGAGAGATCTCATTCAAGGAGCAGAAAGCTATAAG
AATCTTTTATTAGAATATGAAAAGCAGTCAGAGCAACTGGATGTGGAAAAAGAACGTGCTAATAATTTTG
AGCATCGTATTGAAGACCTTACAAGACAATTAAGAAATTCGACTTTGCAGTGTGAAACAATAAATTCTGA
TAATGAAGATCTCCTGGCTCGTATTGAGACATTACAGTCTAATGCCAAATTATTAGAAGTACAGATTTTA
GAAGTCCAGAGAGCCAAAGCAATGGTAGACAAAGAATTAGAAGCTACTGTAACCTCTGAATTCGAGAGCTACA
AAGGAACATGCCACTACTGTAAATGAACTTGAAGAACTTCAGGTACAACTTCAAAAGGAAAAGAAACA
GCTTCAGAAAACCATGCAAGAATTAGAGCTGGTTAAAAAGGATGCCCAACAAACCACATTGATGAATATG
GAAATAGCTGATTATGAACGTTTGATGAAAGAACTAAATCAAAAGTTAACTAATAAAACAACAAGATAG
AAGATTTGGAGCAAGAAATAAAAATTCAAAAACAGAAACAAGAAACCCTACAAGAAGAAATAACTTCATT
ACAGTCTTCAGTACAACAATATGAAGAAAAAAACACCAAAATCAAGCAATTGCTTGTGAAAACCAAAAAG
GAACTGGCAGATTCAAAGCAAGCAGAAACTGATCACTTAATACTTCAAGCATCTTTAAAAGGTGAGCTGG
AGGCAAGCCAGCAGCAAGTAGAAGTCTATAAAATACAGCTGGCTGAAATAACATCAGAGAAGCACAAAAT
CCACGAGCACCTGAAAACCTCTGCGGAACAGCACCAGCGTACGCTAAGTGCATACCAGCAGAGAGTGACA
GCACTACAGGAAGAGTGCCGTGCTGCCAAGGCAGAACAAGCTACTGTAACCTCTGAATTCGAGAGCTACA
AAGTCCGAGTTCATAATGTTCTAAAACAACAGAAAAATAAATCTATGTCTCAGGCTGAAACTGAGGGCGC
TAAACAAGAAAGGGAACATCTGGAAATGCTGATTGACCAGCTAAAAATCAAATTACAAGATAGCCAAAAT
AACTTACAGATTAATGTATCTGAACTTCAAACATTGCAGTCTGAACATGATACACTGCTAGAAAGGCACA
ACAAGATGCTGCAGGAAACTGTGTCCAAAGAGGCGGAACTCCGGGAAAATTGTGTTCAATACAGTCAGA
GAACATGATGATGAAATCTGAACATACACAGACTGTGAGTCAGCTAACATCCCAGAACGAGGTCCTTCGA
AATAGCTTCCGAGATCAAGTGCGACATTTGCAGGAAGAACACAGAAAGACAGTGGAGACATTACAGCAGC
AGCTCTCCAAGATGGAAGCACAGCTCTTCCAGCTTAAGAATGAACCGACCACAAGAAGCCCAGTTTCCTC
TCAACAATCTTTGAAGAACCTTCGAGAAAGGAGAAACACAGACCTCCCGCTTCTAGACATGCACACTGTA
ACCCGGGAAGAGGGAGAAGGCATGGAGACAACTGATACGGAGTCTGTGTCTTCCGCCAGCACATACACAC
AGTCTTTAGAGCAGCTGCTTAACTCTCCCGAAACTAAACTTGAGCCTCCATTATGGCATGCTGAATTTAC
CAAAGAAGAATTGGTTCAGAAGCTCAGTTCCACCACAAAAAGTGCAGATCACTTAAACGGCCTGCTTCGG
GAAACAGAAGCAACCAATGCAATTCTTATGGAGCAAATTAAGCTTCTCAAAAGTGAAATAAGAAGATTGG
AAAGGAATCAAGAGCGAGAGAAGTCTGCAGCTAACCTGGAATACTTGAAGAACGTCTTGCTGCAGTTCAT
TTTCTTGAAACCAGGTAGTGAAAGAGAGAGACTTCTTCCTGTTATAAATACGATGTTGCAGCTCAGCCCT
GAAGAAAAGGGAAAACTTGCTGCGGTTGCTCAAGGTGAGGAAGAAAATGCTTCCCGTTCTTCTGGATGGG
CATCCTATCTTCATAGTTGGTCTGGACTTCGATAGGTTGATGGAAGGAATATTTTTATTAACCAAATAGA
ATCTATTTACAAAAATGGTTCACGTATATTACCACAATTCTTTTGTCAAAAGTGTGTATATATGTTTGC
ATCTACATATATTTGTACATCTATATGACAGATGTATTTTAAAAGTTTCATCTTGAAGTAAAAGTACAAC
AGCTTGAAGTGTTGATAGCAGGCCACAGCCCTCTAACTCATGTGATTTCCCATGCATGCTGCCAGAATAA
AACCACCAGGAATGAATTCACTCCCCACTTCTCTGGAACCTCAGGACCCGCCCATTTCTCGGCAGTACTG
TGAATTTTGAAGTTAAACTAAATTTTGGTACCATACCAACTGGAATTCAGTCCTTTAAAAATAATGTTTCA
AGGCCAGGTGTGGTGATTCATGCCTGAAATCCCACTACTTTGGGAGGCTGAGGCTGGAGAATTGCTTGAG
GCTAGTGAGCTGTGACTCCCACTGCACTCCAGCTCGGGGAACAGAGCGAGACCTTGTCTCTAAAAATAAT
AGTAATAAAATAAAAATAACGTTTTATGACTATTTATTGCAAGGTCAGAGTTACAGATTGTTATAAATTG
TTGAGAAATTTTTGTGATTAGAATATGAAGGAAAAAGCTTTGGTAAAAGTGACATGTTAAGGGGCTA
TGAAGTAAATATGCTGCAGTTAATTGTGCTAAGTTAAAATACAGTTTAGTTATTTGCTTTAAAATAAACT
CTTCTTTTTTCTTTAAAGTATACTATCTCAAAACTCATTATGTTGTCAGAGCCCTAGAGCTGGCTAGTG
TAACACTGACTATGAGTAGGTGGGCCCACCACTTGAGTTGAGGTGATTTCATGGTGTCTTTCCAGGCTCT
TGATAGGGTGTCACTGCATGCAAGCCATGAATCTGTTTTGAGAATCCTCTCCATTTTCCCAAATAAAAAC
CTATCACAACAGTGACTATATCACTCAGCATTGGATCTAAATATAAAAGTGGTGCTTTCAGTGTTTTTGG
CAGATAGTGTTCCATAAGCTTTCCATCAGAAGGGATTTTAGACACCTTAGAGGTCCGTGCTACATCGTCA
CAGTTCCTCCGAATAACCTTAGGTGGTAGTGTTACTTGCCTTTGACACCTCTGCATATGTTTTAATGACT
AGATCCAAACTGTGTTGTTCTTAAATCAAAAATTGGATAATTTGTAATATTTATGTGTTAATCACACAGT
ATGCTCTCTGAAGTTCTCTTAAGCCTTCAGTTTATACTCTTAATTTAATTTTCTTTCTGAGCTGGAAAT
TGGCTTTGCACTTTGGTTACACAGAACATTGGTTTCCAATTCAGTTTAACTGAAATTTGCTGCTGATATG
TTGAGTTTGTTCTTTAAAAAATAGCTCATATATCTCATCTTTCCTCCTGTCTTAGAAGAACAGACCTAAC
TAGTGAATGTATTAATGAAAATGCATCTATTTCAGAGCTGACATGAAGATGTTAGTTTTTTTACTTTATA
AACTGTGAATATGAGTATGCCAGCTGCATACGATGTAACTAATCATATTTAAATATATTTCACTTTCTCT
TTGACTTTAGACCTTTTGAAGTCTGTATAAACTTGTTTTGAAATATAGTCTCTGCTTACGAATGTCATAA
CAAAATAATTTTTTGCATGATAAAAAATTACTTTGATTACAAAAGGCGTATTCTTTCATGGTTTCTGCAA
TGAGAGGAAGTGTAATGATTATTTTAATATTTCTATTAAATATGTTTAACTGT

SEQ ID NO:28
ATGGCCACAGCTTGTAAAAGATCAGGAGAACCTCAGTCTGACGACATTGAAGCTAGCCGAATGAAGCGAG
CAGCTGCAAAGCATCTAATAGAACGCTACTACCACCAGTTAACTGAGGGCTGTGGAAATGAAGCCTGCAC
GAATGAGTTTTGTGCTTCCTGTCCAACTTTTCTTCGTATGGATAATAATGCAGCAGCTATTAAAGCCCTC
GAGCTTTATAAGATTAATGCAAAACTCTGTGATCCTCATCCCTCCAAGAAAGGAGCAAGCTCAGCTTACC

TABLE A-continued

Sequences of the Known Genes Identified Among Renal SEREX Clones

TTGAGAACTCGAAAGGTGCCCCCAACAACTCCTGCTCTGAGATAAAAATGAACAAGAAAGGCGCTAGAAT
TGATTTTAAAGATGTGACTTACTTAACAGAAGAGAAGGTATATGAAATTCTTGAATTATGTAGAGAAAGA
GAGGATTATTCCCCTTTAATCCGTGTTATTGGAAGAGTTTTTTCTAGTGCTGAGGCATTGGTACAGAGCT
TCCGGAAAGTTAAACAACACACCAAGGAAGAACTGAAATCTCTTCAAGCAAAAGATGAAGACAAAGATGA
AGATGAAAAGGAAAAAGCTGCATGTTCTGCTGCTGCTATGGAAGAAGACTCAGAAGGCATCTTCCTCAAGG
ATAGGTGATAGCTCACAGGGAGACAACAATTTGCAAAAATTAGGCCCTGATGATGTGTCTGTGGATATTG
ATGCCATTAGAAGGGTCTACACCAGATTGCTCTCTAATGAAAAAATTGAAACTGCCTTTCTCAATGCACT
TGTATATTTGTCACCTAACGTGGAATGTGACTTGACGTATCACAATGTATACTCTCGAGATCCTAATTAT
CTGAATTTGTTCATTATCGGAATGGAGAATAGAAATCTCCACAGTCCTGAATATCTGGAAATGGCTTTGC
CATTATTTTGCAAAGCGATGAGCAAGCTACCCCTTGCAGCCCAAGGAAAACTGATCAGACTGTGGTCTAA
ATACAATGCAGACCAGATTCGGAGAATGATGGAGACATTTCAGCAACTTATTACTTATAAAGTCATAAGC
AATGAATTTAACAGTCGAAATCTAGTGAATGATGATGATGCCATTGTTGCTGCTTCGAAGTGCTTGAAAA
TGGTTTACTATGCAAATGTAGTGGGAGGGGAAGTGGACACAAATCACAATGAAGAAGATGATGAAGAGCC
CATCCCTGAGTCCAGCGAGCTGACACTTCAGGAACTTTTGGGAGAAGAAAGAAGAAACAAGAAAGGTCCT
CGAGTGGACCCCCTGGAAACTGAACTTGGTGTTAAAACCCTGGATTGTCGAAAACCACTTATCCCTTTTG
AAGAGTTTATTAATGAACCACTGAATGAGGTTCTAGAAATGGATAAAGATTATACTTTTTTCAAAGTAGA
AACAGAGAACAAATTCTCTTTTATGACATGTCCCTTTATATTGAATGCTGTCACAAAGAATTTGGGATTA
TATTATGACAATAGAATTCGCATGTACAGTGAACGAAGAATCACTGTTCTCTACAGCTTAGTTCAAGGAC
AGCAGTTGAATCCATATTTGAGACTCAAAGTTAGACGTGACCATATCATAGATGATGCACTTGTCCGGCT
AGAGATGATCGCTATGGAAAATCCTGCAGACTTGAAGAAGCAGTTGTATGTGGAATTTGAAGGAGAACAA
GGAGTTGATGAGGGAGGTGTTTCCAAAGAATTTTTTCAGCTGGTTGTGGAGGAAATCTTCAATCCAGATA
TTGGTATGTTCACATACGATGAATCTACAAAATTGTTTTGGTTTAATCCATCTTCTTTTGAAACTGAGGG
TCAGTTTACTCTGATTGGCATAGTACTGGGTCTGGCTATTTACAATAACTGTATACTGGATGTACATTTT
CCCATGGTTGTCTACAGGAAGCTAATGGGG#GGAACTTTTCGTGACTTGGGAGACTCTCACCCAG
TTCTATATCAGAGTTTAAAAGATTTATTGGAGTATGAAGGGAATGTGGAAGATGACATGATGATCACTTT
CCAGATATCACAGACAGATCTTTTTGGTAACCCAATGATGTATGATCTAAAGGAAAATGGTGATAAAATT
CCAATTACAAATGAAAACAGGAAGGAATTTGTCAATCTTTATTCTGACTACATTCTCAATAAATCAGTAG
AAAAACAGTTCAAGGCTTTTCGGAGAGGTTTTCATATGGTGACCAATGAATCTCCCTTAAAGTACTTATT
CAGACCAGAAGAAATTGAATTGCTTATATGTGGAAGCCGGAATCTAGATTTCCAAGCACTAGAAGAAACT
ACAGAAATATGACGGTGGCTATACCAGGGACTCTGTTCTGATTAGGGAGTTCTGGGAAATCGTTCATTCAT
TTACAGATGAACAGAAAAGACTCTTCTTGCAGTTTACAACGGGCACAGACAGAGCACCTGTGGGAGGACT
AGGAAAATTAAAGATGATTATAGCCAAAAATGGCCCAGACACAGAAAGGTTACCTACATCTCATACTTGC
TTTAATGTGCTTTTACTTCCGGAATACTCAAGCAAAGAAAAACTTAAAGAGAGATTGTTGAAGGCCATCA
CGTATGCCAAAGGATTTGGCATGCTGTAA

SEQ ID NO:29
GGCCGTTCCCCTCTCCTCAGCAGTAGCTCTATGGTTTCAGGGCGGCAACGTGCAGCGTCCTTACCTTGAG
CCTGTGCAGTTGCCCTCACCCCGGAATCCATAGTCACTGTGACGAGGCGGGAGGACTTGGGCGACAGGTA
GCCTCCCAGTCCCACACGCTGCGGGTCCGCGCCTGGCCAAGCCACCTCGACCTGTGAAGTTGGGGGCGGT
ACCCAGCAACTCCCCCTGTGCAGCCGCCGTTTCCAAGGGGTCAGGAACCGCTGTGTTTGTTTCGTCCGCG
TAGCCAGGGCGGGTCGCGGAGTACTGTGCCTGACCCGACGGTGGCAAGTCTGACGCGTCAGCCAGAGACC
GGTGCCCGGTGTAGGAGTCGCAGCCTGGGCTGTGAGCGGCTGCTGGGTAGACAGACTTGCTTTCTCTTAC
AGCATGTCATTTCCAAAATGCATCGTGGTGCTTCTGCCTTAAGTCCTATAGGAAGACACTGCCGCCACTA
GACCGGTGCTTATGGTCGCCACTGTTATTCTGACTCAGGTCCCGTGTCATTGAGCATATGTATGAAAATG
CCTTAGGAGGGAACCATGGAGAAGTATGTGAGACTGCAGAAGATTGGAGAAGGTTCATTTGGAAAAGCTG
TTCTTGTTAAATCGACAGAGGATGGCAGACATTATGTCATCAAGGAAATTAACATCTCAAGAATGTCTGA
TAAAGAAAGGCAAGAATCAAGGAGAGAAGTTGCTGTATTGGCAAACATGGACATCCAAATATTGTCCAA
TATAAAGAATCATTTGAAGAAAATGGCTCTCTCTACATAGTAATGGATTACTGTGAAGGAGGTGATTTGT
TTAAACGAATAAATGCTCAGAAAGGCGCTCTGTTTCAAGAAGACCAGATTTTGGACTGGTTTGTGCAGAT
ATGTTTGGCTCTGAAGCATGTACATGATAGAAAAATTCTTCACCGAGACATAAAGTCACAGAACATATTT
CTAACCAAAGATGGGACAGTGCAGCTTGGAGATTTTGGAATTGCTCGAGTTCTTAATAGTACTGTAGAGC
TGGCTCGAACTTGCATAGGCACTCCATACTACTTGTCACCTGAAATCTGTGAAAACAAGCCTTATAACAA
TAAAAGTGACATTTGGGCTTTGGGCTGTGTCCTTTATGAGTTGTGTACACTTAAACATGCATTTGAAGCT
GGAAACATGAAAAACCTGGTACTGAAGATAATCTCCGGATCCTTTCCTCCAGTGTCTCCACATTACTCCT
ATGATCTCCGCAGCTTGCTGTCTCAGTTATTTAAAAGAAATCCTAGGGATAGACCATCAGTCAACTCCAT
ATTGGAGAAAGGTTTTATAGCTAAACGAATCGAAAAGTTTCTCTCCCCTCAGCTTATTGCAGAAGAATTT
TGTCTAAAAACACTTTCAAAGTTTGGACCACAGCCTCTCCCAGGTAAAAGACCAGCATCAGGACAAGGTG
TCAGTTCTTTTGTCCCTGCTCAGAAAATCACAAAGCCTGCTGCTAAATACGGAGTGCCTTTAACATATAA
GAAGTATGGAGATAAAAAGTTACTTGAGAAAAAAACCACCCCCAAAACATAAACAGGCCCATCAAATTCCC
GTGAAGAAAATGAATTCTGGAGAAGAAAGGAAGAAAATGTCTGAGGAAGCAGCAAAAAAAAGAAGGTTGG
AATTTATTGAGAAAGAAAAGAAGCAAAAGGATCAGATTAGGTTCCTGAAGGCTGAGCAGATGAAGCGGCA
AGAGAAGCAGCCGGTTGGAGAGGATAAATAGGGCCAGGGAACAAGGATGGAGGAATGTTTAAGGGCTGGT
GGAAGCGGTGAAGTAAAGGCTTCCTTTTTTGGCATTGGAGGGGCTGTCTCTCCATCACCGTGTTCTCCTC
GAGGCCAGTATGAACATTACCATGCCATTTTTGACCAAATGCAGCGGCTAAGAGCAGAAGATAATGAAGC
AAGATGGAAGGGGAATCTATGGTCGATGGCTCCCAGAAAGGCAAAAGGACACTTAGCTGTAGAGAGA
GCCAACCAAGTGGAAGAATTCCTACAGCGTAAACGAGAAGCTATGCAGAATAAAGCCCGAGCCGAAGGAC
ACGTGGTTTATTTGGCAAGACTGAGGCAAATAAGACTACAAAATTTTAATGAGCGCCAACAGATTAAAGC
CAAACTTCGTGGTGAGAATAAAGAAGCTGATGGTACCAAAGGACAAGAAGCAACTGAAGAGACTGACATG
AGGCTCAAAAAGATGGAGTCACTTAAGGCGCAAACAAATGCACGTGCTGCTGTACTAAAAGAACAGCTGG
AGCGAAAAAGAAAGGAAGCTTATGAAAGAAAAGAAAGTATGGGAAGAACATTTGGTGGCGAGGGTAAA
AAGCTCAGATGTTCCTCTGCCTTTGGAACTTCTTGAAACAGGTGGTTCTCCATCAAAGCAGCAGGTGAAG
CCTGTCATTTCTGTGACTTCAGCTTTGAAAGAAGTGGGCCTGGATGGAAGTTTAACTGATGATACCCAGGAAG
AAGAAATGGAAAAGAGTAACAGTGCTATTTCAAGTAAGCGAGAAATCCTGCGTAGGCTAAATGAAAATCT
TAAAGCTCAAGAGGATGAAAAGGAAAAGCAGCATCACTCAGGTTCTTGTGAGACCGTTGGTCACAAAGAT
GAGAGAGAGTATGAGACAGAAAATGCCATTTCCTCTGATCGCAAGAAGTGGGAGATGGGAGGTCAGCTTG
TGATTCCTCTCGATGCAGTGACACTGGATACATCCTTCTCTGCAACCGAAAACATACTGTGGGAGAGGT
TATTAAATTAGATTCTAATGGCTCTCCAAGAAAAGTCTGGGGGAAAAACCCTACAGATTCTGTGCTGAAG

TABLE A-continued

Sequences of the Known Genes Identified Among Renal SEREX Clones

```
ATACTTGGAGAAGCTGAATTACAGCTATAGACAGAACTACTAGAAAACACATCTTTTAAAAGTGAGGTTT
ATGCTGAAGAGGAGAACTACAAACCCTTACTTACTGAAGAAGAGAATCTGCAGTGCATTTCAAAAGAAAT
AAATCCATCAGCTACTGTTGATTCTACTGAAACGAAAAGTCCAAAGTTTACTGAGGTGTCTCCACAAATG
TCAGAAGGAAATGTGGAAGAACCTGATGATTTGGAAACAGAAGTTCTACAAGAGCCAAGTAGCACACACA
CAGATGGGAGTTTGCCACCTGTTCTTAATGATGTGTGGACTAGAGGAAGGAAGCAGCTAAGGAAACTGA
GTTGGAAGATAAGGTTGCTGTGCAGCAGAGTGAAGTTTGTGAAGATAGAATTCCAGGGAACGTGGACCAA
TCCTGTAAGGATCAGAGAGATCCTGCAGTAGACGATTCTCCGCAGTCTGGCTGTGATGTAGAGAAGTCAG
TACAGCCAGAATCGATTTTCCAGAAAGTGGTTCATTCTAAGGACTTGAACTTAGTTCAGGCAGTTCATTG
CTCACCAGAAGAACCAATTCCAATTCGATCTCACTCTGATTCTCCACCAAAAACTAAGAGCAAGAATTCC
TTACTGATTGGACTTTCAACTGGTCTGTTTGATGCAAACAATCCAAAGATGCTGAGGACCTGCTCACTTC
CAGATCTTTCCAAGCTGTTCAGAACCCTAATGGACGTTCCCACTGTGGGGACGTTCATCAAGACAGTCT
TGAAATCGATGAGCTGGAAGATGAACCAATTAAAGAAGGGCCTTCTGATTCCGAAGCACTGTATTTGAA
GAAACTGACACAGATTTACAAGAGCTTCAGGCCTCAATGGACAGCTGCTTAGGGAGCAACCAGGTGACG
AATACAGTGAGGAGGAAGAGTCTGTTTTAAAAAGCAGCGATGTGGAGCAGACAGCAAGAGGGACAGATGC
CCCAGACGAGGAGGACAACCCCAGCAGCGAAAGCCCCTGAACGAGGAATGGCACTCAGATAATAGTGACG
CTGAGACCACTAGTGAATGTGAATATGACAGTGTCTTTAACCATTTAGAGGAACTAAGACTTCACTTGGA
GCAAGAAATGGGCTTTGAAAAGTTCTTTGAGGTTTATGAGAAAGTAAAGGCTATTCATGAGGATGAAGAT
GAAAATATTGAAATTTGTTCAACAATAGTTGAGAATATTTTGGGCAATGAGCACCAGCATCTCTATGCCA
AGATTCTGCATTTAGTCATGGCAGATGGAGCCTATCAGGAAGATAATGATGAATAATCCTCAGGACATTC
TTTAATAGTCAACTGTAAGAACACATTTGAACTTGGCTCATAATACAAGCTTCCTGGGAAATA

SEQ ID NO:30
TCGGGCGCAGCCGCGAAGATGCCGTTGGAACTGACGCAGAGCCGAGTGCAGAAGATCTGGGTGCCCGTGG
ACCACAGGCCCTCGTTGCCCAGATCCTGTGGGCCAAAGCTGACCAACTCCCCCACCGTCATCGTCATGGT
GGGCCTCCCCGCCCGGGGCAAGACCTACATCTCCAAGAAGCTGACTCGCTACCTCAACTGGATTGGCGTC
CCCACAAAAGTGTTCAACGTCGGGGAGTATCGCCGGGAGGCTGTGAAGCAGTACAGCTCCTACAACTTCT
TCCGCCCCGACAATGAGGAAGCCATGAAAGTCCGGAAGCAATGTGCCTTAGCTGCCTTGAGAGATGTCAA
AAGCTACCTGGCGAAAGAAGGGGGACAAATTGCGGTTTTCGATGCCACCAATACTACTAGAGAGAGGAGA
CACATGATCCTTCATTTTGCCAAAGAAAATGACTTTAAAGCGTTTTTCATCGAGTCGGTGTGCGACGACC
CTACAGTTGTGGCCTCCAATATCATGGAAGTTAAAATCTCAGCCCGGATTACAAAGACTGCAACTCGGC
AGAAGCCATGGACGACTTCATGAAGAGGATCAGTTGCTATGAAGCCAGCTACCAGCCCCTCGACCCCGAC
AAATGCGACAGGGACTTGTCGCTGATCAAGGTGATTGACGTGGGCCGGAGGTTCCTGGTGAACCGGGTGC
AGGACCACATCCAGAGCCGCATCGTGTACTACCTGATGAACATCCACGTGCAGCCGCGTACCATCTACCT
GTGCCGGCACGGCGAGAACGAGCACAAACCTCCAGGGCCGCATCGGGGGCGACTCAGGCCTGCTCCAGCCGG
GGCAAGAAGTTTGCCAGTGCTCTGAGCAAGTTCGTGGAGGAGCAGAACCTGAAGGACCTGCGCGTGTGGA
CCAGCCAGCTGAAGAGCACCATCCAGACGGCCGAGGCGCTGCGGCTGCCCTACGAGCAGTGGAAGGCGCT
CAATGAGATCGACGCGGGCGTCTGTGAGGAGCTGACCTACGAGGAGATCAGGGACACCTACCCTGAGGAG
TATGCGCTGCGGGAGCAGGACAAGTACTATTACCGCTACCCCACCGGGGAGTCCTACCAGGACCTGGTCC
AGCGCTTGGAGCCAGTGATCATGGAGCTGGAGCGGCAGGAGAATGTGCTGGTCATCTGCCACCAGGCCGT
CCTGCGCTGCCTGCTTGCCTACTTCCTGGATAAGAGTGCAGAGGAGATGCCCTACCTGAAATGCCCTCTT
CACACCGTCCTGAAACTGACGCCTGTCGCTTATGGCTGCCGTGTGGAATCCATCTACCTGAACGTGGAGT
CCGTCTGCACACACCGGGAGAGGTCAGAGGATGCAAAGAAGGGACCTAACCCGCTCATGAGACGCAATAG
TGTCACCCCGCTAGCCAGCCCCGAACCCACCAAAAAGCCTCGCATCAACAGCTTTGAGGAGCATGTGGCC
TCCACCTCGGCCGCCCTGCCCAGCTGCCTGCCCCGGAGGTGCCCACGCAGCTGCCTGGACAAAACATGA
AAGGCTCCCGGAGCAGCGCTGACTCCTCCAGGAAACACTGAGGCAGACGTGTCGGTTCCATTCCATTTCC
ATTTCTGCAGCTTAGCTTGTGTCCTGCCCTCCGCCCGAGGCAAAACGTATCCTGAGGACTTCTTCCGGAG
AGGGTGGGGTGGAGCAGCGGGGAGCCTTGGCCGAAGAGAACCATGCTTGGCACCGTCTGTGTCCCCTCG
GCCGCT

SEQ ID NO:31
TGCTGCAGCCGCTGCCGCCGATTCCGGATCTCATTGCCACGCGCCCCCGACGACCGCCCGACGTGCATTC
CCGATTCCTTTTGGTTCCAAGTCCAATATGGCAACTCTAAAGGATCAGCTGATTTATAATCTTCTAAAGG
AAGAACAGACCCCCCAGAATAAGATTACAGTTGTTGGGGTTGGTGCTGTTGGCATGGCCTGTGCCATCAG
TATCTTAATGAAGGACTTGGCAGATGAACTTGCTCTTGTTGATGTCATCGAAGACAAATTGAAGGGAGAG
ATGATGGATCTCCAACATGGCAGCCTTTTCCTTAGAACACCAAAGATTGTCTCTGGCAAAGACTATAATG
TAACTGCAAACTCCAAGCTGGTCATTATCACGGCTGGGGCACGTCAGCAAGAGGGAGAAAGCCGTCTTAA
TTTGGTCCAGCGTAACGTGAACATATTTAAATTCATCATTCCTAATGTTGTAAAATACAGCCCGAACTGC
AAGTTGCTTATTGTTTCAAATCCAGTGGATATCTTGACCTACGTGGCTTGGAAGATAAGTGGTTTTCCCA
```

II. Novel gene products

| Clone | SEQ ID NO: | Size | Tissue mRNA expression |
|---|---|---|---|
| NY-REN-45 | 1 | 4.0 kb | Ubiquitous |
| NY-REN-49 | 2 | 1.1 kb | Ubiquitous |
| NY-REN-50 | 3 | 1.8 kb | Ubiquitous |
| NY-REN-57 | 4, 5 | 2.9 kb | Ubiquitous |
| NY-REN-58 | 6 | 1.9 kb | Ubiquitous |
| NY-REN-60 | 7 | 4.0 kb | Ubiquitous |
| NY-REN-62 | 8, 9 | 2.7 kb | Ubiquitous |
| NY-REN-64 | 10, 11 | 3.0 kb | Ubiquitous |

III. Clones which react with autologous sera only:
  NY-REN-47 (SED ID NO:23)
  NY-REN-49 (SED ID NO:2)
  NY-REN-50 (SED ID NO:3)

IV. Clones which react with sera from normal control donors

|  | Frequency of sera reactivity | |
| --- | --- | --- |
| Clone | normal | cancer patient |
| NY-REN-46 | 4/4 | 6/14 |
| NY-REN-48 | 14/14 | 17/17 |
| NY-REN-51 | 1/12 | 3/17 |
| NY-REN-52 | 4/12 | 7/17 |
| NY-REN-53 | 4/19 | 10/31 |
| NY-REN-54 | 5/8 | 7/7 |
| NY-REN-55 | 3/19 | 6/31 |
| NY-REN-56 | 3/19 | 7/31 |
| NY-REN-57 (SEQ ID NOS: 4, 5) | 1/19 | 3/31 |
| NY-REN-58 | 1/12 | 2/17 |
| NY-REN-59 | 1/19 | 4/31 |
| NY-REN-61 | 3/19 | 5/31 |
| NY-REN-62 | 1/19 | 4/31 |
| NY-REN-63 | 2/19 | 12/31 |
| NY-REN-64 (SEQ ID NOS: 10, 11) | 3/19 | 6/31 |
| NY-REN-65 | 2/19 | 2/31 |

V. Clones which react with sera from cancer patients only (failed to react with 19 normal patient serum samples). These clones are preferred for therapeutic and diagnostic applications.

|  | Frequency of reactivity |
| --- | --- |
| NY-REN-32 | 3/31 |
| NY-REN-45 (SEQ ID NO: 1) | 3/31 |
| NY-REN-57 (SEQ ID NOS: 4, 5) | 2/31 |
| NY-REN-60 (SEQ ID NO: 7) | 5/31 |
| NY-REN-66 (SEQ ID NO: 35) | 2/31 |

VI. Additional allogeneic screening of NY-REN renal SEREX clones

Renal SEREX clones were tested for reactivity with wsera from the normal and various cancer patients listed below.

|  | Sera | | | | |
| --- | --- | --- | --- | --- | --- |
| Clone | normal | colon | renal | lung | breast |
| NY-REN-3 | 0/26 | 7/37 | 8/32 | 0/23 | 1/26 |
| NY-REN-12 | 0/19 | 0/16 | 3/32 | 0/15 | 0/16 |
| NY-REN-19 | 0/19 | 0/16 | 2/32 | 0/15 | 0/16 |
| NY-REN-21 | 0/16 | 3/16 | 3/32 | 1/15 | 0/16 |
| NY-REN-25 | 0/15 | 0/16 | 5/32 | 0/15 | 0/16 |
| NY-REN-31 | 0/14 | 0/16 | 5/32 | 0/15 | 0/16 |
| NY-REN-32 | 0/14 | 2/16 | 3/32 | 0/15 | 0/16 |
| NY-REN-37 | 0/15 | 0/16 | 2/32 | 0/15 | 0/16 |
| NY-REN-45 (SEQ ID NO: 1) | 0/14 | 0/16 | 3/32 | 1/15 | 0/16 |
| NY-REN-57 (SEQ ID NOS: 4, 5) | 0/19 | 0/16 | 2/32 | 0/15 | 0/16 |
| NY-REN-60 (SEQ ID NO: 7) | 0/19 | 0/16 | 7/32 | 0/15 | 0/16 |
| NY-REN-66 (SEQ ID NO: 35) | 0/19 | 0/16 | 2/32 | 0/15 | 0/16 |

Example 2

Preparation of Recombinant Cancer Associated Antigens

To facilitate screening of patients' sera for antibodies reactive with cancer associated antigens, for example by ELISA, recombinant proteins are prepared according to standard procedures. In one method, the clones encoding cancer associated antigens are subcloned into a baculovirus expression vector, and the recombinant expression vectors are introduced into appropriate insect cells. Baculovirus/insect cloning systems are preferred because post-translational modifications are carried out in the insect cells. Another preferred eukaryotic system is the Drosophila Expression System from Invitrogen. Clones which express high amounts of the recombinant protein are selected and used to produce the recombinant proteins. The recombinant proteins are tested for antibody recognition using serum from the patient which was used to isolated the particular clone, or in the case of cancer associated antigens recognized by allogeneic sera, e.g. certain breast cancer and gastric cancer associated antigens, by the sera from any of the patients used to isolate the clones or sera which recognize the clones' gene products.

Alternatively, the cancer associated antigen clones are inserted into a prokaryotic expression vector for production of recombinant proteins in bacteria. Other systems, including yeast expression systems and mammalian cell culture systems also can be used.

Example 3

Preparation of Antibodies to Cancer Associated Antigens

The recombinant cancer associated antigens produced as in Example 12 above are used to generate polyclonal antisera and monoclonal antibodies according to standard procedures. The antisera and antibodies so produced are tested for correct recognition of the cancer associated antigens by using the antisera/antibodies in assays of cell extracts of patients known to express the particular cancer associated antigen (e.g. an ELISA assay). These antibodies can be used for experimental purposes (e.g. localization of the cancer associated antigens, immunoprecipitations, Western blots, etc.) as well as diagnostic purposes (e.g., testing extracts of tissue biopsies, testing for the presence of cancer associated antigens).

Example 4

Expression of Renal Cancer Associated Antigens in Cancers of Similar and Different Origin The expression of one or more of the renal cancer associated antigens is tested in a range of tumor samples to determine which, if any, other malignancies should be diagnosed and/or treated by the methods described herein. Tumor cell lines and tumor samples are tested for cancer associated antigen expression, preferably by RT-PCR according to standard procedures. Northern blots also are used to test the expression of the cancer associated antigens. Antibody based assays, such as ELISA and western blot, also can be used to determine protein expression. A preferred method of testing expression of cancer associated antigens (in other cancers and in additional same type cancer patients) is allogeneic serotyping using a modified SEREX protocol (as described above for gastric clones).

In all of the foregoing, extracts from the tumors of patients who provided sera for the initial isolation of the cancer associated antigens are used as positive controls. The cells containing recombinant expression vectors described in the Examples above also can be used as positive controls.

The results generated from the foregoing experiments provide panels of multiple cancer associated nucleic acids and/or polypeptides for use in diagnostic (e.g. determining

Example 5

HLA typing of Patients Positive for Renal Cancer Associated Antigen

To determine which HLA molecules present peptides derived from the renal cancer associated antigens, cells of the patients which express the renal cancer associated antigens are HLA typed. Peripheral blood lymphocytes are taken from the patient and typed for HLA class I or class II, as well as for the particular subtype of class I or class II. Tumor biopsy samples also can be used for typing. HLA typing can be carried out by any of the standard methods in the art of clinical immunology, such as by recognition by specific monoclonal antibodies, or by HLA allele-specific PCR (e.g. as described in WO97/31126).

Example 6

Characterization of Renal Cancer Associated Antigen Peptides Presented by MHC Class I and Class II Molecules Antigens which provoke an antibody response in a subject may also provoke a cell-mediated immune response. Cells process proteins into peptides for presentation on MHC class I or class II molecules on the cell surface for immune surveillance. Peptides presented by certain MHC/HLA molecules generally conform to motifs. These motifs are known in some cases, and can be used to screen the renal cancer associated antigens for the presence of potential class I and/or class II peptides. Summaries of class I and class II motifs have been published (e.g., Rammensee et al., *Immunogenetics* 41:178–228, 1995). Based on the results of experiments such as those described above, the HLA types which present the individual breast cancer associated antigens are known. Motifs of peptides presented by these HLA molecules thus are preferentially searched.

One also can search for class I and class II motifs using computer algorithms. For example, computer programs for predicting potential CTL epitopes based on known class I motifs has been described (see, e.g., Parker et al., *J. Immunol.* 152:163, 1994; D'Amaro et al., *Human Immunol.* 43:13–18, 1995; Drijfhout et al., *Human Immunol.* 43:1–12, 1995). HLA binding predictions can conveniently be made using an algorithm available via the Internet on the National Institutes of Health World Wide Web site at URL http://bimas.dcrt.nih.gov. Methods for determining HLA class II peptides and making substitutions thereto are also known (e.g. Strominger and Wucherpfennig (PCT/US96/03182)).

Example 7

Identification of the Portion of a Cancer Associated Polypeptide Encoding an Antigen To determine if the cancer associated antigens isolated as described above can provoke a cytolytic T lymphocyte response, the following method is performed. CTL clones are generated by stimulating the peripheral blood lymphocytes (PBLs) of a patient with autologous normal cells transfected with one of the clones encoding a cancer associated antigen polypeptide or with irradiated PBLs loaded with synthetic peptides corresponding to the putative protein and matching the consensus for the appropriate HLA class I molecule (as described above) to localize an antigenic peptide within the cancer associated antigen clone (see, e.g., Knuth et al., *Proc. Natl. Acad. Sci. USA* 81:3511–3515, 1984; van der Bruggen et al., *Eur. J. Immunol.* 24:3038–3043, 1994). These CTL clones are screened for specificity against COS cells transfected with the cancer associated antigen clone and autologous HLA alleles as described by Brichard et al. (*Eur. J. Immunol.* 26:224–230, 1996). CTL recognition of a cancer associated antigen is determined by measuring release of TNF from the cytolytic T lymphocyte or by $^{51}$Cr release assay (Herin et al., *Int. J. Cancer* 39:390–396, 1987). If a CTL clone specifically recognizes a transfected COS cell, then shorter fragments of the cancer associated antigen clone transfected in that COS cell are tested to identify the region of the gene that encodes the peptide. Fragments of the cancer associated antigen clone are prepared by exonuclease III digestion or other standard molecular biology methods. Synthetic peptides are prepared to confirm the exact sequence of the antigen.

Optionally, shorter fragments of cancer associated antigen cDNAs are generated by PCR. Shorter fragments are used to provoke TNF release or $^{51}$Cr release as above.

Synthetic peptides corresponding to portions of the shortest fragment of the cancer associated antigen clone which provokes TNF release are prepared. Progressively shorter peptides are synthesized to determine the optimal cancer associated antigen tumor rejection antigen peptides for a given HLA molecule.

A similar method is performed to determine if the cancer associated antigen contains one or more HLA class II peptides recognized by T cells. One can search the sequence of the cancer associated antigen polypeptides for HLA class II motifs as described above. In contrast to class I peptides, class II peptides are presented by a limited number of cell types. Thus for these experiments, dendritic cells or B cell clones which express HLA class II molecules preferably are used.

TABLE 1

Sequence homologies

SEQ ID NO: 1
AB002794, U46118RNU46118U19482AF026216AB002739, AB002730, AB002728,
AF058796, AB002777, AF020187, AF009411, AB015609, AF006627, M95076, U43527,
AB002741, U25846, AF006628, AF019043, D83352, U10355, M9957S, U48288,
AF090440, AB007504, U82480, Y15794, AJ005572, AF029349, L10111, S80963,
U38894, L41731, AF022733, AJ225108, Y11879, AF001688, U33214, Z97178,
AF009413, AF019907, AF016371, X71980, AF001522, M77169, AF023132, D83476,
AJ009675, U90554, AF069324, AF048691, Z34799, AF004947, U60149, AF022732,
AF019887, L02937, U55848, AF011331, AF045770, AF043533, X69524, M32882,
U08214, U50847, AF017364, U35364, Y14339, AJ005969, U90S55, U44430, U74296,

TABLE 1-continued

Sequence homologies

AF001501, AJ223316, D78609, U41060, Z54362, AF034387, U62398, AB005545,
AB002533, Y13865, AF009959, L02938, U10555, AL010246, AC003041, U37699,
S75970, AFO71010, Z81311, AB003681, X16353, AB002731, X53081, D63450,
D10911, D90115, X97065, Z82275, AB016891, Y09455, X77990, , W58357, W07820,
AA188593, W81046, AA858164, A1018124, AI139112, AW769634, W00437, D80849,
AA448160, N98650, T31293, H15307, H51146, N29314, AA770301, AA187822,
AA978299, T31823, AA936410, AA993194, N41386, W45601, W81099, C05691,
D60153, AA780119, AA929004, R68608, Z43271, N37024, AA974718, AA928663,
T30120, AA936583, H51109, N20251, W92917, T36035, AA480197, Z24908, N79450,
AA872019, AA902275, N59810, R13443, AA740162, AA937759, N72168, AA970708,
T36257, AA433833, H15700, D5118S, AA249138, R37356, W93028, Z28641,
AA371494, N72757, AA719126, N56164, T31790, D57384, Z41959, NS8984,
AA847848, AA587009, Z39343, AA654834, AA505490, Z38243, D20344, AA252395,
AA025593, H70133, R09101, AA159862, AI032981, Z28355, C75020, AI139642,
D82421, AI126922, C75170, AI016032, C18748, C75478, AI129334, C75472,
AA310765, D63057, C059S2, AA357303, C16591, D82132, L48852, D82799, C75176,
AI124552, AA669404, U30155, C75118, AA374918, C75108, C05853, U30151,
D57346, AI127548, AA918527, AA317816, AA573490, R21699, AA917928, R36311,
AA361522, AA701252, AI085492, H44387, AA156256, AA587935, AA976510,
AA515269, W73374, T27986, N34493, AA737770, N32609, N32612, H64420,
AA415243, AA413717, AA117350, AA242502, AA117343, AA545256, AA7956S1,
AA106372, U31322, AA681967, AA221922, AA600546, AA050610, AU018628, C80932,
AA920654, AA863834, AI099036, AA183239, AI115182, AA590910, W65628,
AA162291, , AA109440, AI052952, AA999324, AI105714, AI026280, AI072678,
AA964820, AA754198, AA944557, AI045710, C94989, AA471630, AA933231,
AA509077, AA257557, AA509328, AA109365, AA963207, AA435473, AA999306,
AA406684, AI105662, AA509174, AI108597, AA109374, AA925182, AA471671,
AA088161, AA752812, AA626989, AA406924, AA840999, AA509033, C94899,
AA406875, AA842672, AA123619, AA072471, AA509339, AA933108, AI110259,
AA842135, N99262, AA661430, AA842512, AA180648, AI066048, AA559515,
AA406761, AA109423, AF074736, AA257676, D87312, AA257488, AA114390,
AI087701, W06665, W32852, AA123649, AA842505, AA509330, AA908025, AA257279,
AI105717, AA406673, AA627018, AA406850, AA161668, AA114453, AA109372,
AA257572, AA803997, AA406943, AA257495, AA841368, AA257572, AI082949,
AA842888, W06539, AA118223, AA406986, AA471717, AI096212, AA257707,
AA257649, AI053126, AA508950, AA713366, W69049, AA965381, AA208680,
AI057997, AA161707, AI058071, AA675858, AA257513, AI083337, AA406908,
AI083256, AA659956, AA842532, AA754036, AA753165, W18199, AI109620,
AI058022, AA064026, AA471431, AA032116, AA754544, AI108146, C42045,
AA843025, AI109103, AA509237, AA161620, AA257665, AA471605, W84932,
AA841358, AA843040, AA471695, AA003471, AA840977, AA509267, AA841711,
AA471488, AA257699, N98079, AA454318, W04102, AA842874, N99754, AA509307,
AA751845, AA661358, AA508954, AA406746, AA842720, W23363, AA508951,
AI068913, AA417420, AI108220, AA508946, AA471497, AA842911, AA842501,
AA123614, AA509218, AA547812, AA752986, AA752003, AA406839, AAS08993,
AA161747, AA509008, AA180623, AA508986, AA842627, AA753129, AA509214,
AA406733, AI105737, N74818, AA753300, AA430818, AA417415, AA114426, R46936,
AA979824, AA246112, AA753138, AI058077, AA842464, AA966639, AA842265,
AA509025, AA601853, W15128, AA660039, AA842275, AA454424, AA180651,
AA842423, AA257507, AI063375, AA180692, AA051990, W15094, AA180620, W00308,
AA406729, AA257712, AA257445, AA433148, C48534, AA495533, C08939, AA406845,
AA933362, AA509242, AA842023, W29144, AI087490, AA842237, AA601823, W06538,
AI087739, AI087524, AA842164, AA842642, AA471553, AA842419, AI113700,
AA675813, AI083003, AI021727, AI083274, AI083309, W32823, AA253962,
AA114520, AA430792, C47230, AA842674, AI053174, D75937, AA843034, W68979,
AI105681, W91819, AA756971, AA509104, AA111828, AI109720, AI110161,
AA933311, AA180602, AA842093, R86419, AI058057, AA186285, AA406891,
AI10572S, AA406888, AA649397, N94700, W51718, AA547916, AA840646, U74116,
AA257756, AI082996, W91818, N74830, AA123585, AA118224, AA454446, AA841367,
AA509109, AA842387, AI052833, AA751998, AA123634, AA257327, AA803962,
AA842493, AA471448, AA406716, AA841361, AA840661, AA713447, AA406754,
AA257695, AA841403, AA751834, AA406947, AI096182, AI105734, W15132, W59918,
AA089352, AA180566, AA257427, AA257522, AA180706, AA471469, AA509264,
AA509032, AA749469, AA752028, AA754167, AA754646, AA842335, AA842574,
AI065957, AI065970, A1096289, AA109379, AA109472, AA114484, AA161689,
AA430830, AA406948, AA433246, AA454371, AA471492, AA471703, AA752086,
AA842624, AI096185, R47079, R86415, AA161711, AA161655, AA180S49, AA257424,
AA257437, AA257749, AA433393, AA471419, AA471602, AA430922, AA661401,
AA752034, AA752066, AA842384, AI082936, AI083329, AI105677, Z33912,
AA109362, AA109417, AA051807, AA430797, AA406799, AA430806, AA495548,
AA661116, AI082951, AI105685, AI114069, R47062, W59884, AA109292, AA751829,
AA754172, AA842257, AI082934, AI082958, AA180706, AA471516, AA508692,
AA751563, AA751816, AA753137, AA753167, AA840972, AA842079, AA874756,
AI105522, AI108824, AA180588, AA406676, AA471392, AA509142, AA840909,
AA842175, AI066854, R47172, AA161565, AA257643, AA753161, AA471447,
AA680450, AA752897, AA753237, AA842230, AA842544, AA161635, AA454428,
AA508933, AA509309, C41215, AA842585, D73786, D75990, D75808, AA627049,

TABLE 1-continued

Sequence homologies

N74809, AA257682, AA257517, AA257668, AA471470, AA509251, AA509051,
AA990913, C39627, C41200, C42101, C46071, C48450, AA840970, AA842156,
AA430902, AA842216, AA007706, AA406765, AA180574, AA842310, AI067585,
AI077003, AA756933, AA114501, AA406690, AA454440, AA661371, AA056797,
AA114372, AA180676, AI082955, AA406735, AA752005, W29142,
AA109261, AA842401, AA842602, AA246079, AI043420, AA626993, AA123655,
AA257716, AA406931, AA791379, AI105668, AA842538, R47669, AA088150,
AA109308, AA738555, AA123638, AA180582, AA123597, AA471535, AA180728,
AA161741, AA186201, AA430817, AA433170, AA454407, AA471686, AA161596,
AA509110, AA675874, AA471540, Z26577, AA753093, AI066829, D37716, AA627017,
N99292, AA508936, AA257656, AA406768, AA471587, H39287, AA842431, AA161715,
AA509204, AA979935,

SEQ ID NO.: 2, AF086243, AE001154, X62889, , W67765, W67764, AA947751,
AI141491, W76469, AA906091, AA872676, AA349825, H77545, H91001, W72232,
AA948309, AA361403, R57582, AA337188, AA215714, AA481093, T75310, AA976452,
AI120744, AA462558, AI158491, AA014020, AA285990, AA051044, AA473453,
AA896862, W56907, AA218305, AA020167, W85164, AA017810, W30604, AA541978,
W20894, AA023164, AA760425, AA024084, AA840044, , AA231755, T20644, C4S833,
T24185, C68940, D37618, AA964657, AI011924

SEQ ID NO.: 3, L08501, Z97205, Z48950, AF010400, AC005162, L08502, D50608,
, AA707653, AA861639, AA292496, AA702524, AI097367, AI138504, AI147933,
AI141836, AI075247, N63868, W88668, AA703146, AA625621, AA292247, AI032848,
AA005331, AA699781, AA427941, D31111, D31113, N92013, AA884207, AA044752,
R70900, R16693, AA906542, R35112, AA481286, D80100, AA235512, AA060995,
AA867982, D59403, W88874, AA558590, R10048, AA719917, H43573, R49500,
AA744780, AA047136, AA789101, AA906332, AA747301, AA830606, AA434559,
AA236698, AA328889, N98469, W17299, W46605, AA258082, AI078045, R11930,
W74577, AA703312, AI082727, R45189, N76461, AA010500, W63646, W38891,
AA490651, AA558805, W87891, AA160849, AA618177, AA776126, AA161281,
AA822308, AA499768, AA028780, AA183100, AA276783, AA120227, AA200285,
AA212541, AA116265, AA821616, AA265629, AA108594, W61565, AA030311, W42275,
AA419903, AA268027, AA028211, AA518504, AA125394, , C92235, C92002, C29917,
AI145662, C65317, AA901847, AI137443, Z14719, D35515, R90625, H76970, ,

SEQ ID NO.: 4, AL031178, Y11905, AF031904, M34309, M29366, L33953, L33952,
L33956, L33954, L33957, U41289, X13369, AL022072, AJ223074, AF078695,
AC004683, X17267, AF025526, AF071798, AC005274, AB004537, X68248, AF035537,
AF056116, AB009052, AL023286, AF0S8701, L20725, AF001308, U22438,
AA211485, AA579574, Ai078750, AA568661, AA604128, H49462, AA767424, H97012,
AA565823, H49463, AA827171, T87152, F22114, AA748475, T31504, Z42997,
T89930, R02581, H75949, T87057, AA322268, R02700, AA00S034, AA576177,
AI014302, AA348159, T83607, AA322497, AA211532, AA019517, R27657, AA026869,
N67589, T83782, AA129383, Z39829, AA814308, AA425564, H67997, AA004420,
AA644513, AA007691, T62593, AA333601, H75334, AI057250, T62521, N73865,
AA004558, AA004484, AA007690, AA910241, AA456251, AA004568, AA341266,
T28757, AA132360, AA781316, AA456942, AA782765, AA662593, AA461351,
AA885220, N33840, AA843737, T62232, AA608559, AA643270, R44662, AI074863,
AI051088, N63305, W249S5, AA085886, W31918, AA047466, AA178965, AA369890,
AA515015, N79466, AA768162, AA864694, AA811390, AA834531, AA293263,
AA768335, AA749083, T57520, AA292001, AI085512, AA969032, AI027062,
AA595663, AA827242, AA744475, , AA472485, AA097011, AA959170, AA647546,
AA986669, AI006628, W12604, AI122356, AA571721, AA433697, AA880171,
AA015463, AA116290, C87721, AA437983, AA990395, AA265925, W14785, W89262,
AA059703, AA413613, AI020231, AA667024, AA407526, AA221491, AA222523,
C76436, AA409700, W35766, , AA859485, H33704, T46512, C25899, T41882,
C26586, C92302, AA660448, C94493, C25527, D3S045, D33727, F14543, D37473,
T45969, AA040979, D68274, T38420, AA228607, AA660541, T38283, AA842575,
C71889, T38745, D68465, T46732, AA598393, C23775, C64798, AA042714, F19972,
C65873, N97974, AA114425, AA900456

SEQ ID NO.: 5, U29344, S80437, M76767, X62889, M84761, J03514, X62888,
X13415, X13135, U05714, AC004013, U58675, S47635, Z81533, ACOO52SO,
AC003661, AB008567, Y13444, X96401, AF026487, AF026488, , AA781445,
AI037943, AI129371, C15883, AI073336, AA904077, AA569042, AI039428,
AA568701, AA058907, AA911112, AA234022, N95359, AA565390, AA082427,
AA588430, D60358, AA045488, AA084417, N72089, Ai143390, R51974, AA081439,
AA635907, T47621, AA579930, AA995057, AA827039, AA872490, AA588319,
AA069032, AA062768, AA534011, W96404, H06082, AA938900, AA971262, AA836547,
AA251544, AA250742, AA830405, AA906492, AA102653, R38286, AA258075, H83302,
H38522, R61787, R33742, R24094, AI052406, AA9314S2, R23634, R39640,
AA974568, AI028383, AA312451, AA148800, AI138982, R36172, AA926921,
AA472563, AA914598, AA423256, AA476186, AA041992, W84938, AA797706,
AA709956, AA544361, AI006075, AA717202, AA008602, AA033399, AA472306,
AI037430, AI152943, AA475582, AA471742, AA530292, AA277496, AA718588,
AA823112, AA822771, AA710973, AA981780, AA718846, AA797557, AA510746,

TABLE 1-continued

Sequence homologies

AI036049, AA543891, AA606513, AA9817S8, AA822268, AA413161, AA472201,
AA646527, AA213036, AA168254, AA718549, AA458342, AA119418, AA879925,
AA050917, AA718814, AA793638, AA177849, AA575627, AA537367, AI121788,
AA203946, AA413157, AA517432, AA867736, AI037420, W30436, , Z71851,
AA957415, AI112847, AA955881, AA963915, AI043663, C95061, AI009894,
AA957229, AI044678

SEQ ID NO.: 6, AC002426, AC004674, AC004675, AC004006, L12157, U20839,
U46028, U20835, AC004058, X67115, X76266, M25485, U59759, AC005172, U70848,
AF042274, X14724, L31840, L41679, , W52480, AA863014, W56770, AA286755,
AA164604, W52777, AA814246, AA765427, AA873647, AA360577, AI139274,
AA770312, AA732557, AA568651, AA164603, W56724, AA194905, AA865009, R16884,
R08110, F07672, AA577790, T11467, AA502489, AA366688, AA480628, AA516318,
AA090005, AA081908, F01265, AA780686, , AA466811, AA465808, AA197646,
AI157174, AA153086, AA197667, AA066612, AA058086, AA024186, AA110104,
AA880419, AA870161, AA153880, AA072995, , AI031052, AI043934, AA849320,
D15181, U95093, AI096188, T09655, C62926, AA996434, AA925202, AA817271,
AA901051, R03660, AA948980, AA658709, AA899446, AA957150, AA800160, T76196,
AA891787

SEQ ID NO.: 7, X63547, X63546, AF017306, U44839, U20657, AF017305,
AJ001589, L21998, D21270, Z48245, U63834, Z68006, L04573, D63819, AC005266,
AF025468, M94131, , AI056961, C15588, AA373847, AA887911, N87070, R39133,
AA226825, AA353972, AA325352, R88378, AA490675, AA456219, AA701415,
AA046611, AA456224, , AA065652, AA221447, AA710221, AA717401, AA254049,
AA041745, AA510261, AA170745, AA656404, AA572506, AA174539, AA217630,
AI134284, C58457, C11202, AA413362, AA728532

SE ID NO.: 8, AB016886, Z92811, AL021481, U52078, L46702, U23515, AC005555,
Z84814, Z93016, D21138, X57513, L07144, M28488, U15974, U52513,
AF026939, L19120, J05258, Z13985, Z70691, U59227, , AA190526, AA764854,
AI014655, H88220, AA622877, N32046, H89609, AA682362, AA464420, AA375477,
AA284905, AA257109, N80276, H89373, N92393, AA884334, AA778708, AA766209,
AA535677, W46414, AA770266, AA983635, AA721113, H88219, R87349, AA628091,
AI116513, AA183589, AI035517, AA209952, AA184622, AI097904, AA016440,
AA162370, AA939521, AA162376, AA718152, AA048154, AA253815, AA795350,
AA996981, C44448, C41783, C44695, C44039, C62421, C47063, C45014, D36613,
C60872, C50136, C69177, AI055708, D27648, C65648, AI114022, AI064663,
AI107213, AA395461, AA800126, AA891487, T01611, C27943, AI113482, C83830

SEQ ID NO.: 9, L43510, U71249, L11275, X73541, Z28317, AB008270, X7S652,
U05987, U85262, U24189, Z46676, X70823, AC004981, D11079, X56121, M58053,
U33636, Z92773, U23168, D31662, , R15557, F01629, N71722, AA252548,
AA806751, T59557, AA612671, AA329585, AA295675, AA166990, AA128100, H46363,
AA125810, , AA396888, AA408999, AA270873, AA144722, AA863954, W10303,
C38016, N96746, Z37622, AA395862, C38756, F15295, N99294, W68877, C44749,
C24349, F15569, AA113611, AA689147, N96676, C73598, F15564, L46559, W06235,
T09718, H77154, T14151, AI082914, AA650815, AA728021, AA072559, C92112,
T46743, C61743, AA550223, C12798, AA275531, AA681003, T75878, AI100047,
T75882, AA848187, T44109, AA542686, H21339

SEQ ID NO.: 10, ZB1595, U41372, U01317, AE000696, AC002057, X66250, L11665,
D13438, U29377, Z50028, U40953, AA114228, AI025080, R80188, W28745,
AA381819, AA381991, Z44165, H75915, AI124743, H08139, AA375957, AA381750,
AA166751, R42511, T26985, , AA471592, AA661387, AA606231, D35147

SEQ ID NO.: 11, X76498, Z97632, AC004232, AC005184, AC002545, AC003991.

EQUIVALENTS

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

We claim:

1. A method of diagnosing a disorder characterized by expression of a human cancer associated antigen precursor coded for by a nucleic acid molecule, comprising:

contacting a biological sample isolated from a subject with an agent that specifically binds to the nucleic acid molecule, an expression product thereof, or a fragment of an expression product thereof complexed with a human leukocyte antigen (HLA) molecule, wherein the nucleic acid molecule is a NA Group 1 nucleic acid molecule that hybridizes under stringent conditions to a nucleic acid molecule selected from the group consisting of SEQ ID NOs: 1, 4, 5, 7, 10, 11, and 35, and determining the interaction between the agent and the nucleic acid molecule or the expression product as a determination of the disorder, wherein said stringent conditions comprise hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA) and wherein SSC is 0.15M sodium chloride/0.15M sodium citrate, pH7; SDS is sodium dodecyl sulphate; and EDTA is ethylenediaminetetracetic acid.

2. The method of claim 1, wherein the agent is selected from the group consisting of
   (a) a nucleic acid molecule consisting of a nucleotide sequence selected from the group consisting of SEQ ID NOs: 1, 4, 5, 7, 10, 11, and 35, or a fragment thereof,
   (b) an antibody that binds to an expression product of a nucleic acid molecule consisting of a nucleotide sequence selected from the group consisting of SEQ ID NOs: 1, 4, 5, 7, 10, 11, and 35, and
   (c) an agent that binds to a complex of an HLA molecule and a fragment of an expression product of a nucleic acid molecule consisting of a nucleotide sequence selected from the group consisting of SEQ ID NOs: 1, 4, 5, 7, 10, 11, and 35.

3. The method of claim 1, wherein the disorder is characterized by expression of a plurality of human cancer associated antigen precursors and wherein the agent is a plurality of agents, each of which is specific for a different human cancer associated antigen precursor, and wherein said plurality of agents is at least 2, at least 3, at least 4, at least 5, at least 6, at least 7, at leas at least 9 or at least 10 such agents.

4. The method of any of claims 1, 2, or 3, wherein the agent is specific for a human cancer associated antigen precursor that is a renal cancer associated antigen precursor.

5. A method for determining regression, progression or onset of a condition characterized by expression of abnormal levels of a protein encoded by a nucleic acid molecule that is a NA Group 1 molecule, comprising monitoring a sample, from a patient who has or is suspected of having the condition, for a parameter selected from the group consisting of
   (i) the protein
   (ii) a peptide derived from the protein
   (iii) an antibody which selectively binds the protein or peptide, and
   (iv) cytolytic T cells specific for a complex of the peptide derived from the protein and an MHC molecule, as a determination of regression, progression or onset of said condition, wherein the NA group 1 molecule hybridizes under stringent conditions to a nucleic acid molecule selected from the group consisting of SEQ ID NOs: 1, 4, 5, 7, 10, 11, and 35, wherein said stringent condition comprise hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$ (pH7), 0.5% SDS, 2 mM EDTA) and wherein SSC is 0.15M sodium chloride/0.15M sodium citrate, pH7; SDS is sodium dodecyl sulphate; and EDTA is ethylenediaminetetracetic acid.

6. The method of claim 5, wherein the sample is a body fluid, a body effusion or a tissue.

7. The method of claim 5, wherein the step of monitoring comprises contacting the sample with a detectable agent selected from the group consisting of (a) an antibody which selectively binds the protein of (i), or the peptide of (ii), (b) a protein or peptide which binds the antibody of (iii), and (c) a cell which presents the complex of the peptide and MHC molecule of (iv).

8. The method of claim 7, wherein the antibody, the protein, the peptide or the cell is labeled with a radioactive label or an enzyme.

9. The method of claim 5, comprising assaying the sample for the peptide.

10. The method of claim 5, wherein the nucleic acid molecule is selected from the group consisting of SEQ ID NOs: 1, 4, 7, 10, and 11, or a fragment thereof.

11. The method of claim 5, wherein the nucleic acid molecule is selected from the group consisting of SEQ ID NOs: 1, 4, 5, 7, 10, 11, and 35, or a fragment thereof that reacts with allogenoic cancer antisera.

12. The method of claim 5, wherein the protein is a plurality of proteins, the parameter is a plurality of parameters, each of the plurality of parameters being specific for a different of the plurality of proteins, at least one of which is a cancer associated protein encoded by a NA Group 1 molecule.

* * * * *

UNITED STATES PATENT AND TRADEMARK OFFICE
CERTIFICATE OF CORRECTION

PATENT NO. : 6,440,663 B1
DATED : August 27, 2002
INVENTOR(S) : Scanlan et al.

It is certified that error appears in the above-identified patent and that said Letters Patent is hereby corrected as shown below:

Column 132,
Line 43, delete "at leas" and insert -- at least 8, --.
Line 67, delete "condition" and insert -- conditions --.

Column 134,
Line 8, delete "4,7" and insert -- 4, 5, 7 --.
Line 11, allogenoic" and insert -- allogeneic --.

Signed and Sealed this

Twenty-second Day of April, 2003

JAMES E. ROGAN
*Director of the United States Patent and Trademark Office*